(12) United States Patent
Navia

(10) Patent No.: US 11,173,029 B2
(45) Date of Patent: Nov. 16, 2021

(54) APPARATUS AND METHOD FOR TREATING A REGURGITANT HEART VALVE

(71) Applicant: THE CLEVELAND CLINIC FOUNDATION, Cleveland, OH (US)

(72) Inventor: Jose L. Navia, Shaker Hts., OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 193 days.

(21) Appl. No.: 16/258,843

(22) Filed: Jan. 28, 2019

(65) Prior Publication Data

US 2019/0151088 A1 May 23, 2019

Related U.S. Application Data

(62) Division of application No. 14/502,000, filed on Sep. 30, 2014, now abandoned.

(60) Provisional application No. 61/884,406, filed on Sep. 30, 2013.

(51) Int. Cl.
*A61F 2/24* (2006.01)

(52) U.S. Cl.
CPC .......... *A61F 2/2454* (2013.01); *A61F 2/2445* (2013.01); *A61F 2/2457* (2013.01); *A61F 2220/0075* (2013.01); *A61F 2230/0013* (2013.01); *A61F 2230/0034* (2013.01);
(Continued)

(58) Field of Classification Search
CPC .......................................... A61F 2/2454–2457
See application file for complete search history.

(56) References Cited

U.S. PATENT DOCUMENTS

| 4,506,394 A | 3/1985 | Bedard |
| 2003/0083742 A1 | 5/2003 | Spence et al. |
| 2006/0149368 A1 | 7/2006 | Spence |

(Continued)

FOREIGN PATENT DOCUMENTS

| WO | 2007/131513 A1 | 11/2007 |
| WO | 2009/067519 A2 | 5/2009 |

(Continued)

OTHER PUBLICATIONS

PCT International Search Report and Written Opinion for corresponding PCT Application Serial No. PCT/US2014/058300, dated Jan. 27, 2015, pp. 1-11.

*Primary Examiner* — Rebecca S Preston
(74) *Attorney, Agent, or Firm* — Tarolli, Sundheim, Covell & Tummino LLP

(57) ABSTRACT

A method for treating regurgitation of blood flow through a diseased heart valve is provided. The diseased heart valve including an annulus, an anterior valve leaflet, a posterior valve leaflet and a subvalvular apparatus. The method includes providing an apparatus comprising a substantially annular support member, at least one infra-annular support member securely connected thereto, and at least one anchoring element associated with the at least one infra-annular support member. The method further includes attaching the substantially annular support member to the annulus of the diseased heart valve and attaching proximal and distal ends of a prosthetic chordae tendineae to the at least one anchoring element and a papillary muscle, respectively, so that the papillary muscle is caused to move medially.

7 Claims, 48 Drawing Sheets

(52) U.S. Cl.
CPC ............... *A61F 2230/0095* (2013.01); *A61F 2250/0067* (2013.01); *A61F 2250/0098* (2013.01)

(56) References Cited

U.S. PATENT DOCUMENTS

| | | |
|---|---|---|
| 2006/0206203 A1 | 9/2006 | Yang et al. |
| 2011/0071626 A1* | 3/2011 | Wright ............. A61B 17/00234 623/2.37 |
| 2012/0179247 A1 | 7/2012 | Navia |

FOREIGN PATENT DOCUMENTS

| | | |
|---|---|---|
| WO | 2011/148374 A2 | 12/2011 |
| WO | 2012/094406 A1 | 7/2012 |

\* cited by examiner

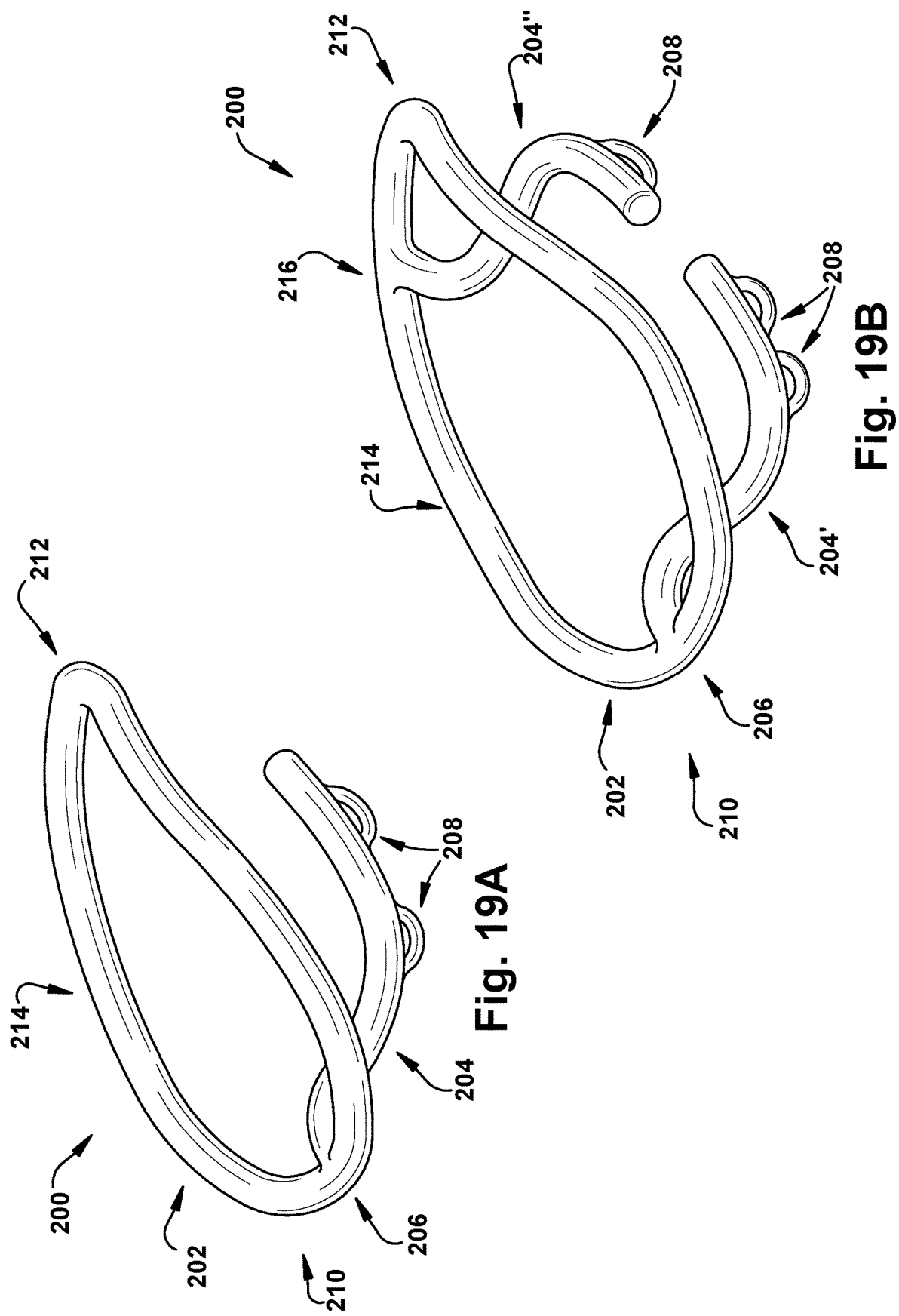

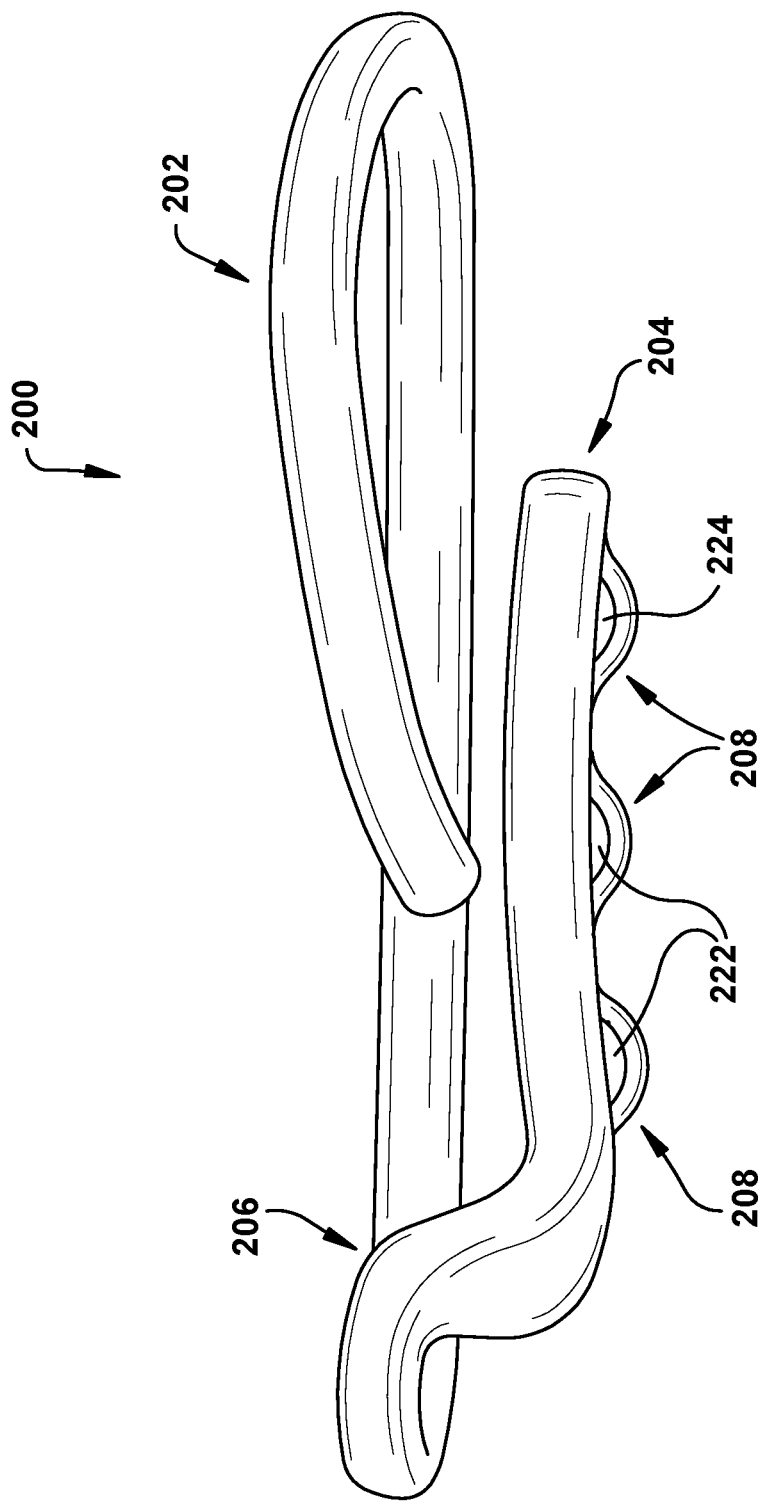

APPARATUS AND METHOD FOR TREATING A REGURGITANT HEART VALVE

RELATED APPLICATIONS

This application is a divisional of U.S. patent application Ser. No. 14/502,000, filed on Sep. 30, 2014, which claims the benefit of U.S. Provisional Patent Application Ser. No. 61/884,406, filed Sep. 30, 2013. The entirety of both applications is hereby incorporated by reference for all purposes.

TECHNICAL FIELD

The present disclosure relates generally to apparatus and methods for treating dysfunctional heart valves, and more particularly to apparatus and related methods that provide sub-valvular leaflet support, as well as sub-valvular apparatus support to passively assist in preventing or mitigating heart valve regurgitation.

BACKGROUND

The opening and closing of heart valves occur primarily as a result of pressure differences. For example, the opening and closing of the mitral valve occurs as a result of the pressure differences between the left atrium and the left ventricle. During ventricular diastole, the venous return of blood from the pulmonary veins into the left atrium causes the pressure in the atrium to exceed that in the left ventricle. As a result, the mitral valve opens and allows blood to enter the left ventricle. As the left ventricle contracts during ventricular systole, the intraventricular pressure rises above the pressure in the atrium and pushes the mitral valve shut.

When the high pressure produced by contraction of the left ventricle pushes the valve leaflets too much, the leaflets become everted and prolapse results. This is normally prevented by contraction of the papillary muscles within the left ventricle, which are connected to the mitral valve leaflets by the chordae tendineae (chords). Contraction of the papillary muscles is simultaneous with the contraction of the left ventricle and serves to keep healthy mitral valve leaflets tightly shut at peak contraction pressures.

Mitral valve malfunction can stem from a variety of etiologies. For example, the causes of mitral regurgitation can range from intrinsic disease of the leaflets (e.g., mainly due to degenerative disease in patients with mitral valve prolapse), to functional mitral regurgitation (FMR), in which the valve is anatomically normal but stretched due to tethering and annular dilatation. Although mitral regurgitation in intrinsic disease occurs initially as leaflet disease, secondary annular dilatation occurs in the large majority of patients by the time they present for treatment. The larger proportion of patients with mitral regurgitation includes those without intrinsic disease of the leaflets, i.e., FMR.

Surgical correction of FMR is based upon overcorrection of concomitant annular dilatation using an undersized, complete, and rigid annuloplasty ring that is intended to reduce the diameter of the mitral annulus and allow for leaflet coaptation. Although complete correction of mitral regurgitation has been surgically demonstrated, an important recurrence of mitral regurgitation after annuloplasty valve repair is common (25%) because the left ventricle continues to dilate or remodel, thereby causing further tethering of the mitral leaflets.

SUMMARY

According to one aspect of the present disclosure, an apparatus is provided for treating regurgitation of blood flow through a diseased heart valve. The diseased heart valve includes an annulus, an anterior valve leaflet, and a posterior valve leaflet. The apparatus includes a substantially annular support member, at least one infra-annular support member securely connected thereto, and at least one anchoring element associated with the at least one infra-annular support member. The at least one anchoring element is configured to securely receive a prosthetic chordae tendineae for attachment to a papillary muscle. The substantially annular support member has at least a first intermediate portion, a second intermediate portion, and a posterior end portion extending between the first and second intermediate portions. The posterior end portion is dimensioned for attachment to a posterior portion of the annulus of the diseased heart valve. The at least one infra-annular support member is securely connected to the substantially annular support member at a first location. The at least one infra-annular support member is dimensioned to extend below the posterior and anterior valve leaflets and across or behind at least one subvalvular structure.

According to another aspect of the present disclosure, an apparatus is provided for treating regurgitation of blood flow through a diseased heart valve. The diseased heart valve includes an annulus, an anterior valve leaflet, and a posterior valve leaflet. The apparatus includes a substantially annular support member, a first infra-annular support member, a second infra-annular support member, and at least one anchoring element associated with at least one of the first and second infra-annular support members. The at least one anchoring element is configured to securely receive a prosthetic chordae tendineae for attachment to a papillary muscle. The substantially annular support member has at least a first intermediate portion, a second intermediate portion, and a posterior end portion extending between the first and second intermediate portions. The posterior end portion is dimensioned for attachment to a posterior portion of the annulus of the diseased heart valve. The first infra-annular support member is securely connected to the substantially annular support member at a first location. The second infra-annular support member is securely connected to the substantially annular support member at a second location. The first and second infra-annular support members are dimensioned to extend below at least one of the posterior and anterior valve leaflets and across or behind at least one subvalvular structure.

According to another aspect of the present disclosure, a method is provided for treating regurgitation of blood flow through a diseased heart valve. The diseased heart valve includes an annulus, an anterior valve leaflet and a posterior valve leaflet. One step of the method includes providing an apparatus comprising a substantially annular support member, at least one infra-annular support member that is securely connected thereto, and at least one anchoring element associated with the at least one infra-annular support member. The substantially annular support member includes at least a first intermediate portion, a second intermediate portion, and a posterior end portion extending between the first and second intermediate portions. Next, the substantially annular support member is attached to the annulus of the diseased heart valve so that the at least one infra-annular support member extends below at least one of the posterior and anterior valve leaflets and across or behind at least one subvalvular structure to prevent or substantially reduce regurgitation of blood flow through the diseased heart valve. The proximal and distal ends of the prosthetic chordae tendineae are then attached to the at least one anchoring element and a papillary muscle, respectively, so that the papillary muscle is caused to move medially and improve cardiac functioning by creating a reverse remodeling of a posterior left ventricular wall, improving valve leaflet coaptation, and reducing tension across the native chordae.

According to another aspect, a method for treating regurgitation of blood flow through a diseased heart valve is provided. The diseased heart valve including an annulus, an anterior valve leaflet, a posterior valve leaflet and a subvalvular apparatus. The method comprises providing an apparatus comprising a substantially annular support member, at least one infra-annular support member securely connected thereto, and at least one anchoring element associated with the at least one infra-annular support member. The substantially annular support member has at least a first intermediate portion, a second intermediate portion and a posterior end portion extending between the first and second intermediate portions. The method further comprises attaching the substantially annular support member to the annulus of the diseased heart valve. The method further includes attaching proximal and distal ends of a prosthetic chordae tendineae to the at least one anchoring element and a papillary muscle, respectively, so that the papillary muscle is caused to move medially. The substantially annular support member is attached so that the at least one infra-annular support member extends below at least one of the posterior and anterior valve leaflets and across or behind at least one subvalvular structure to prevent or substantially reduce regurgitation of blood flow through the diseased heart valve.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIGS. 19A-B are a schematic illustration showing an alternative configuration of the apparatus in FIGS. 1A-18C;

FIG. 20 is a side view of the apparatus shown in FIG. 19A;

DETAILED DESCRIPTION

The present disclosure relates generally to apparatus and methods for treating dysfunctional heart valves, and more particularly to apparatus and related methods that provide sub-valvular leaflet support, as well as sub-valvular apparatus support to passively assist in preventing or mitigating heart valve regurgitation. The present disclosure generally provides an annuloplasty ring system having an infra-annular, free-edge leaflet and subvalvular apparatus supporting mechanism that prevents valve leaflet tethering and regurgitation during systole. Advantageously, the present disclosure provides simultaneous annular and sub-annular levels of cardiac remodeling of a cardiac valve (mitral and tricuspid) to correct and normalize the level and angle of leaflet coaptation, prevent valve leaflet tethering, and resolve recurrent valve regurgitation over time. Consequently, the present disclosure provides treatment for not only regurgitation (e.g., functional mitral regurgitation), but also regurgitation caused by dilated and ischemic cardiomyopathy.

Figure 1A:
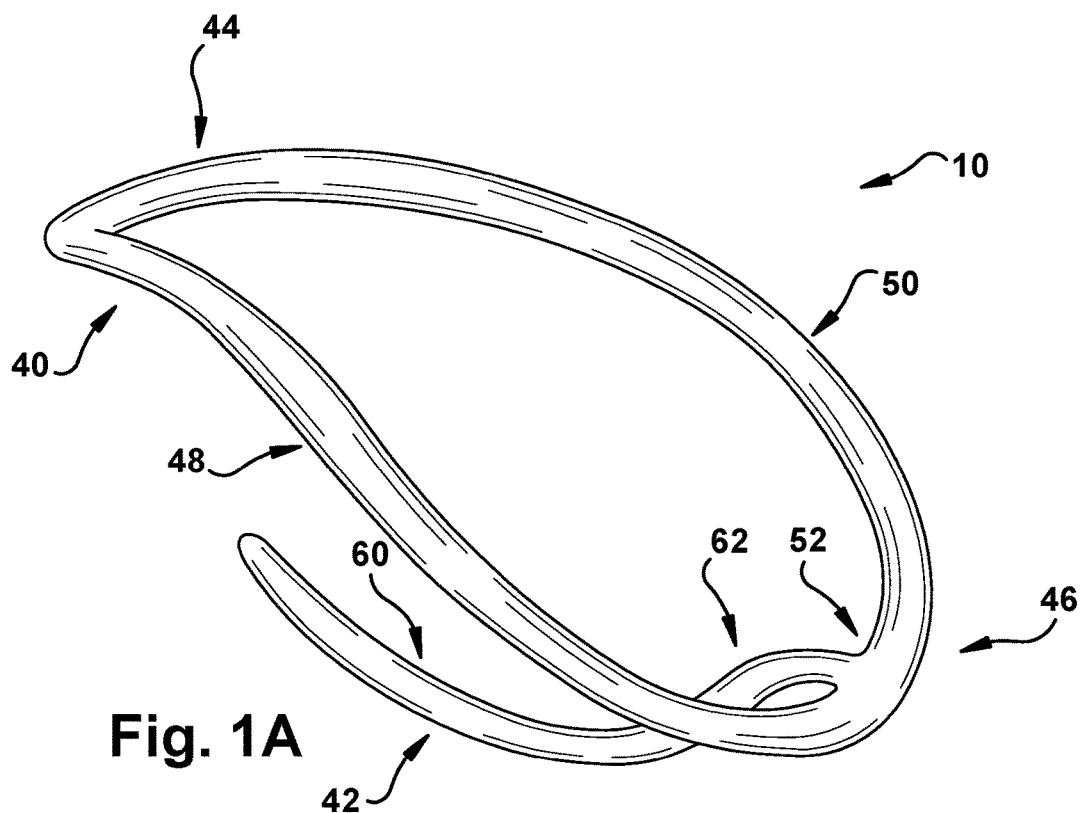
FIG. 1A is a perspective view of an apparatus for treating regurgitation of blood flow through a mitral valve constructed in accordance with one aspect of the present disclosure.
Figure 1B:
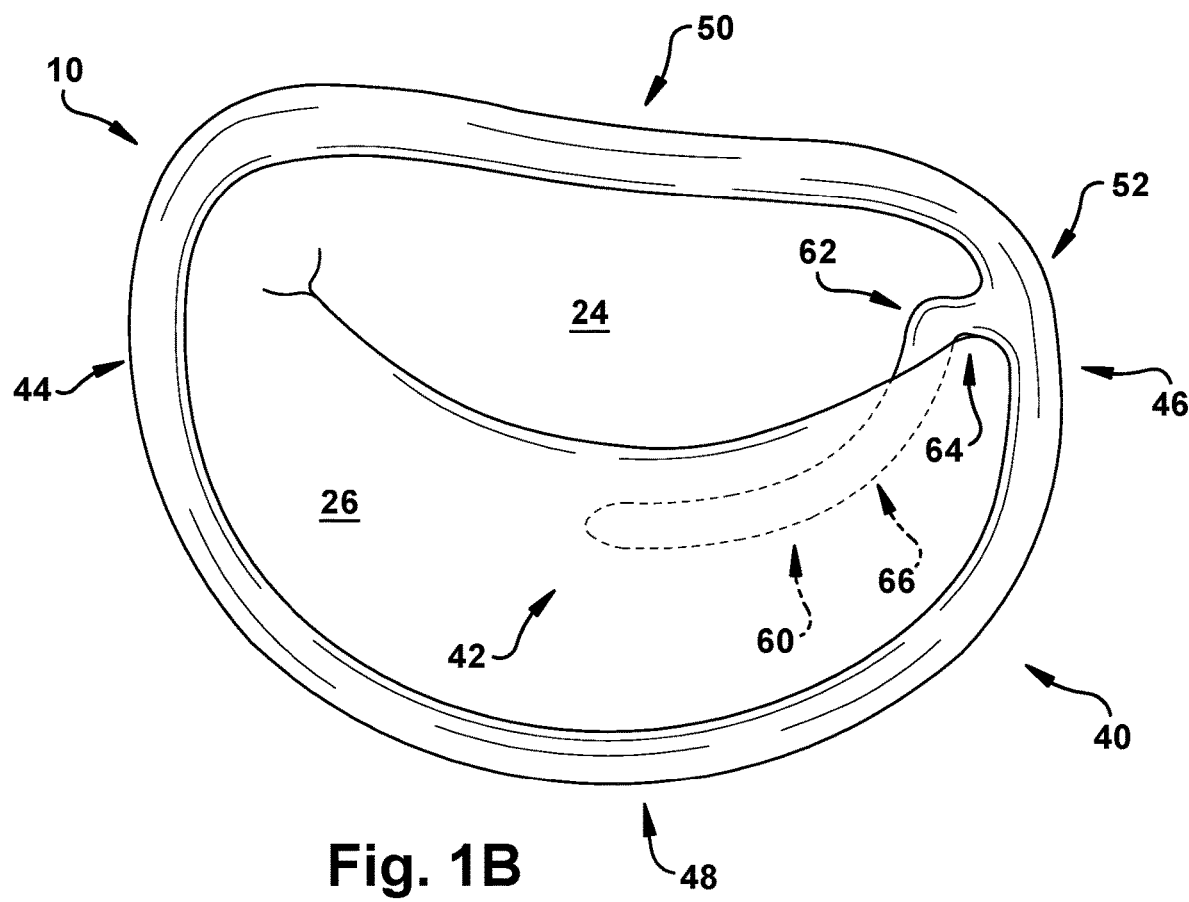
FIG. 1B is a top view of the apparatus in FIG. 1A implanted about a diseased mitral valve.
Figure 1C:
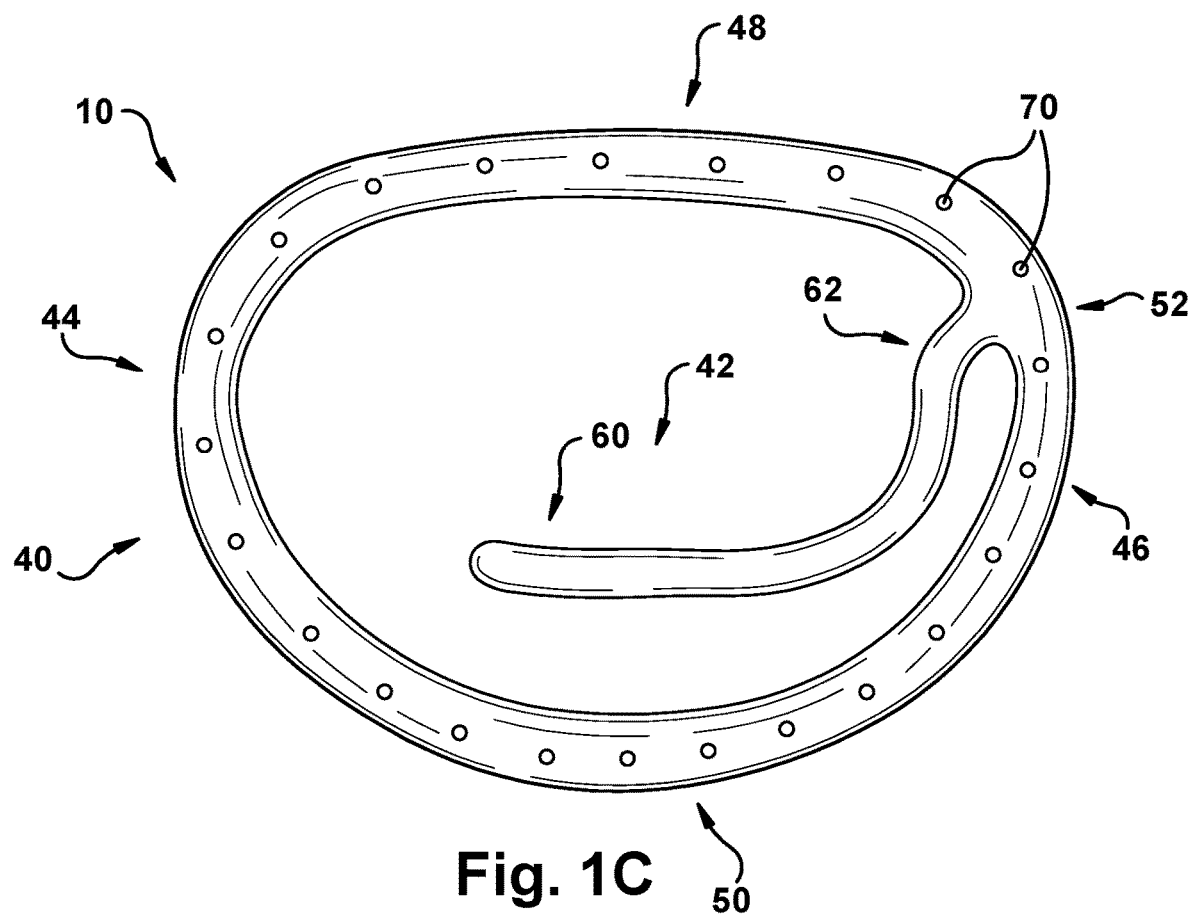
FIG. 1C is a top view of the apparatus in FIG. 1A showing markers to facilitate attachment of the apparatus 10 to the mitral annulus.
Figure 1D:
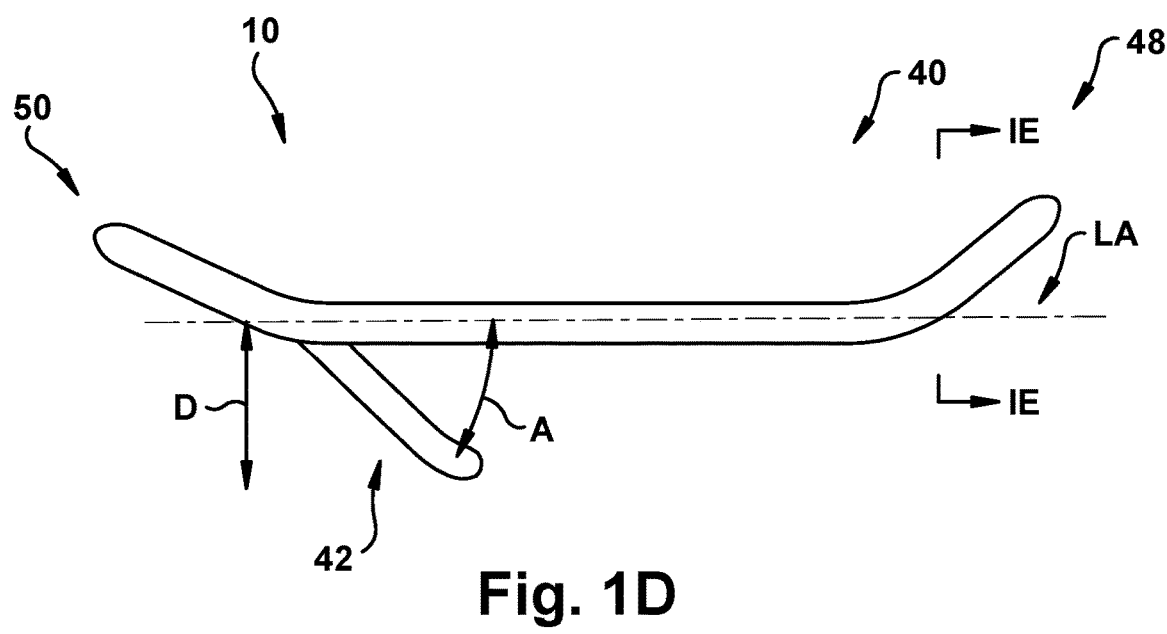
FIG. 1D is a side view of the apparatus in FIG. 1A.
Figure 1E:
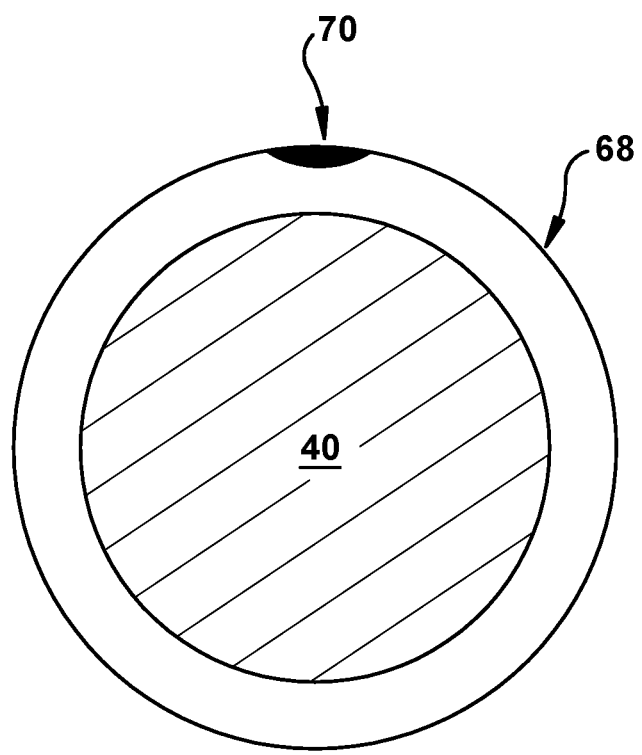
FIG. 1E is a cross-sectional view taken along Line 1E-1E in FIG. 1D.
Figure 2:
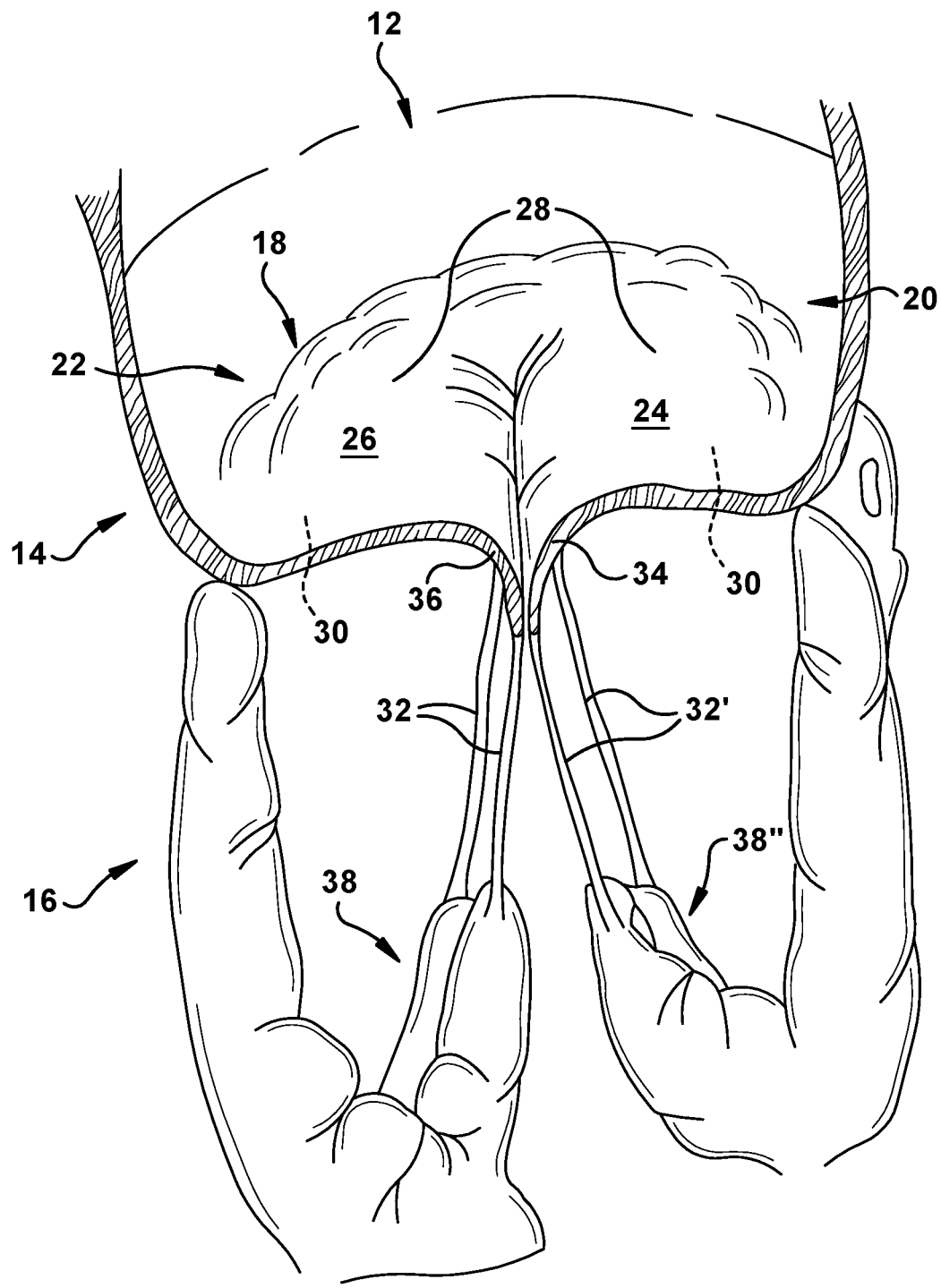
FIG. 2 is a cross-sectional view showing the left side of a human heart.

As representative of one aspect of the present disclosure, FIGS. 1A-E illustrate an apparatus 10 for treating regurgitation of blood flow through a diseased heart valve, such as a mitral valve 12 (FIG. 2). As shown in FIG. 2, the mitral valve 12 is located between the left atrium 14 and the left ventricle 16, and functions to prevent the backflow of blood from the left ventricle into the left atrium during contraction. The mitral valve 12 has a D-shaped annulus 18 that defines the opening between the left atrium 14 and the left ventricle 16, and includes oppositely disposed anterior and posterior portions 20 and 22. The mitral valve 12 is formed by two leaflets; namely, the anterior leaflet 24 and the posterior leaflet 26, each of which includes oppositely disposed superior and inferior surfaces 28 and 30. The anterior leaflet 24 extends along the generally planar base of the D-shaped valve annulus 18 between two fibrous trigones (not shown). The posterior leaflet 26 extends arcuately around the curved portion of the D-shaped annulus 18 of the mitral valve 12. Chordae tendineae 32 and 32' respectively extend between the inferior free edge 34 of the anterior mitral leaflet 24 and the inferior free edge 36 of the posterior mitral leaflet 26 to the papillary muscles 38 and 38' in the left ventricle 16.

Referring to FIGS. 1A-E, the apparatus 10 comprises a substantially annular support member 40 and at least one infra-annular support member, such as an infra-annular posterior support member 42 securely connected thereto. The apparatus 10 has a three-dimensional (3D) shape that corresponds to the saddle-like shape of the mitral annulus 18. The 3D shape allows the apparatus 10 to complement the 3D shape of the mitral valve 12 during the complex physiological motion associated with the cardiac cycle. This removes the need for leaflet resection and/or annulus plication because the apparatus 10, when implanted about the mitral valve 12 (e.g., within or on the annulus 18), passively assists in providing leaflet support without becoming deformed during the cardiac cycle.

The substantially annular support member 40 comprises at least a first intermediate portion 44, a second intermediate portion 46, and a posterior end portion 48 that extends between the first and second intermediate portions. As used herein, the term "substantially annular" can be used to describe an annular support member 40 having a circular or semi-circular configuration. Thus, the term "substantially annular" can refer to an annular support member 40 that is fully annular, fully circular, oval, partially circular, C-shaped, D-shaped, U-shaped, etc. As used herein, the term "substantially" can refer to the complete or nearly complete extent or degree of an action, characteristic, property, state, structure, item or result. For example, an annular support member 40 that is "substantially" annular would mean that the support member is either completely annular or nearly completely annular. The exact allowable degree of deviation from absolute annularity may in some cases depend on the specific context. Generally speaking, however, the nearness of annularity will be so as to have the same overall result as if absolute and total annularity were obtained.

As shown in FIGS. 1A-C, the substantially annular support member 40 can be entirely annular and comprise a first intermediate portion 44, a second intermediate portion 46, a posterior end portion 48 extending between the first and second intermediate portions, and an anterior end portion 50 that extends between the first and second intermediate portions and is oppositely disposed from the posterior end portion. Alternatively, as shown in FIGS. 1F-G, the substantially annular support member 40 can be partly annular and comprise a first intermediate portion 44, a second intermediate portion 46, and a posterior end portion 48 extending between the first and second intermediate portions.

The anterior end portion 50 and the posterior end portion 48 are dimensioned for attachment to the anterior and posterior portions 20 and 22 of the mitral annulus 18, respectively. For example, the posterior end portion 48, the first intermediate portion 44, and the second intermediate portion 46 form a continuous arc so that the posterior end portion has a concave shape relative to the anterior end portion 50. Similarly, the anterior end portion 50, the first intermediate portion 44, and the second intermediate portion 46 form a continuous arc so that the anterior end portion has a convex shape relative to the posterior end portion 48. As shown in FIG. 1D, the substantially annular support member 40 also includes a longitudinal axis LA. The substantially annular support member 40 can have a rigid or semi-rigid configuration.

The apparatus 10 also includes at least one infra-annular posterior support member 42 that is securely and directly connected to the substantially annular support member at a first location 52. As shown in FIGS. 1A-3B, for example, the apparatus 10 includes only one infra-annular posterior support member 42. The infra-annular posterior support member 42 is dimensioned, shaped, and configured to extend below the posterior mitral leaflet 26 and across or behind at least one subvalvular structure when the apparatus 10 is implanted on or about the mitral annulus 18. A subvalvular structure associated with the mitral valve 12 can include, but is not limited to: an inferior aspect of the posterior leaflet 26, such as an inferior free edge 36 of the posterior leaflet; an inferior aspect of the anterior leaflet 24, such as an inferior free edge 34 of the anterior leaflet; chordae tendineae 32 associated with the posterior leaflet; chordae tendineae 32' associated with the anterior leaflet; one or more papillary muscles 38 associated with the tendineae chordae of the posterior leaflet; one or more papillary muscles 38' associated with the chordae tendineae of the anterior leaflet; and combinations thereof.

The infra-annular posterior support member 42 can be shaped, configured, and dimensioned to extend across or behind an entire single subvalvular structure, the entirety of two or more subvalvular structures, a portion of a single subvalvular structure, or a portion of two or more subvalvular structures. For example, the infra-annular posterior support member 42 can be configured to extend below the posterior mitral leaflet 26 and across or behind a portion of the inferior free edge 36 of the posterior mitral leaflet or, alternatively, across or behind a portion of only the inferior free edge of the posterior mitral leaflet. Additionally, the infra-annular posterior support member 42 can be configured to extend below the posterior mitral leaflet 26 and across or behind the entire chordae tendineae 32 and/or papillary muscle(s) 38 associated with the posterior mitral leaflet or, alternatively, a portion of the chordae tendineae of the posterior mitral leaflet. In either or both of these cases, the shape of the infra-annular posterior support member 42 mirrors the 3D shape of the posterior mitral leaflet 26, and in particular the inferior free edge 26 thereof, to prevent or mitigate the restricted motion of the posterior mitral leaflet and, in turn, prevent or mitigate regurgitation of blood flow through the mitral valve 12.

As shown in FIG. 1D, infra-annular posterior support member 42 extends at an angle A and at a distance D below the longitudinal axis LA of the substantially annular support member 40. The angle A of the infra-annular posterior support member 42 is such that the infra-annular posterior support member facilitates optimal leaflet coaptation. In one example of the present disclosure, the angle A can be between about 10° and about 60° (e.g., about 30°). Similarly, the distance D is such that the infra-annular posterior support member 42 extends below the posterior mitral leaflet 26 to enable the infra-annular posterior support member to facilitate optimal leaflet coaptation.

The infra-annular posterior support member 42 can have a rigid or semi-rigid configuration. Where the infra-annular posterior support member 42 has a semi-rigid configuration, for example, the infra-annular posterior support member can be bendable or adjustable to various positions. The infra-annular posterior support member 42 can additionally or optionally include an adjustment mechanism 54 (FIGS. 1H-K) for selectively adjusting the position thereof relative to the longitudinal axis LA. As shown in FIG. 1I, the adjustment mechanism 54 permits the angle A and/or distance D and/or lateral position LP of the infra-annular posterior support member 42 to be selectively adjusted prior to, during, and/or following implantation of the apparatus 10.

To optimize leaflet coaptation, the angle A and/or distance D and/or lateral position LP of the infra-annular posterior support member 42 can be selectively adjusted depending upon the anatomic leaflet configuration, the subvalvular apparatus configuration (e.g., the chordae tendineae 32 and 32' and the papillary muscles 38 and 38'), and/or the free-edge leaflet coaptation angle. The lateral position LP refers to the position of the infra-annular posterior support member 42 relative to the posterior end portion 48 of substantially annular support member 40 and along an axis that is parallel (or substantially parallel) to the longitudinal axis LA. As shown in FIG. 1J, the adjustment mechanism 54 can be operated to adjust the lateral position LP of the infra-annular posterior support member 42 into a pre-set position (indicated by arrow and dashed lines). For example, the apparatus 10 can include three pre-set positions (indicated by "1", "2" and "3"). It will be appreciated that the adjustment mechanism 54 can also be operated to adjust the angle A and/or distance D of the infra-annular posterior support member 42 into a pre-set position.

In one example of the present disclosure, the adjustment mechanism 54 can include an actuation member 56 (FIGS. 1H and 1J), such as a screw (e.g., a ratchet-like mechanism) that is at least partially disposed within the substantially annular support member 40 and operably connected to the infra-annular posterior support member 42. The actuation member 56 can be selectively manipulated (e.g., turned, pushed, pulled, etc.) to adjust (e.g., increase or decrease) the angle A and/or the distance D and/or the lateral position LP of the infra-annular posterior support member 42.

Figure 1F:
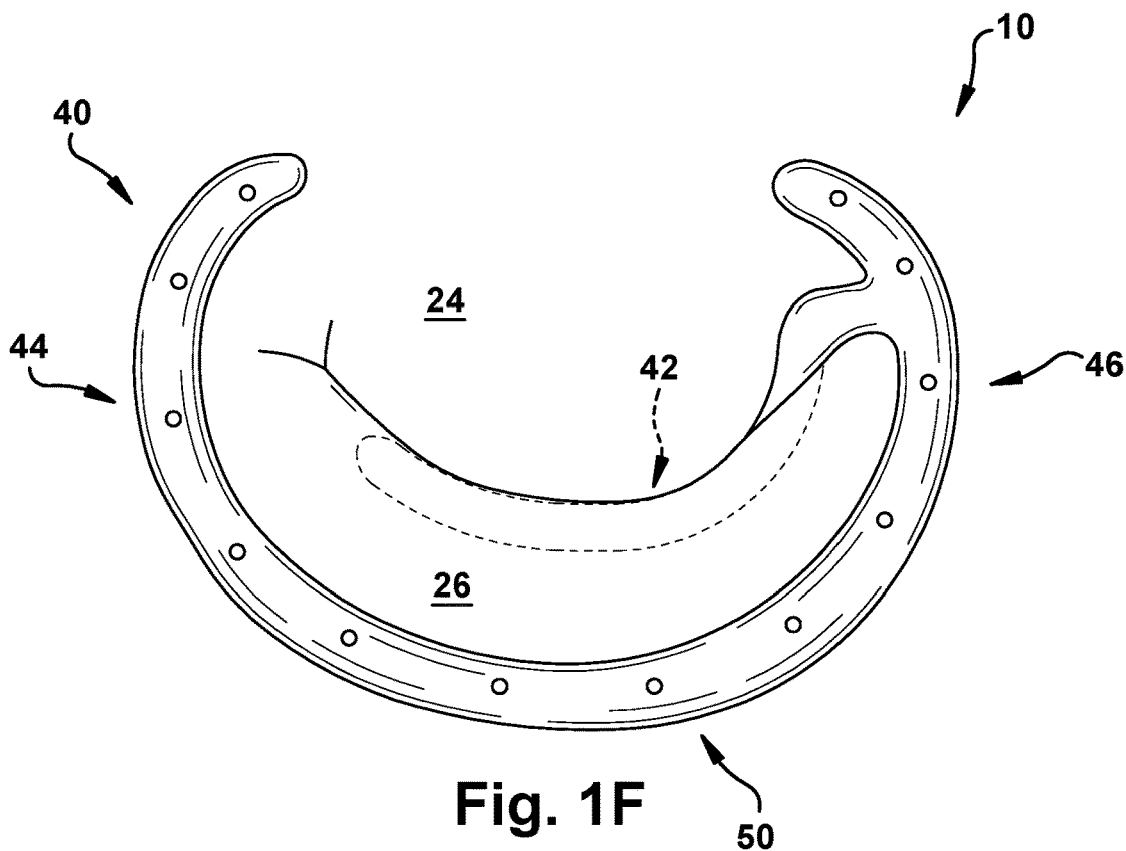
FIG. 1F is a top view showing an alternative configuration of the apparatus in FIG. 1B.
Figure 1G:
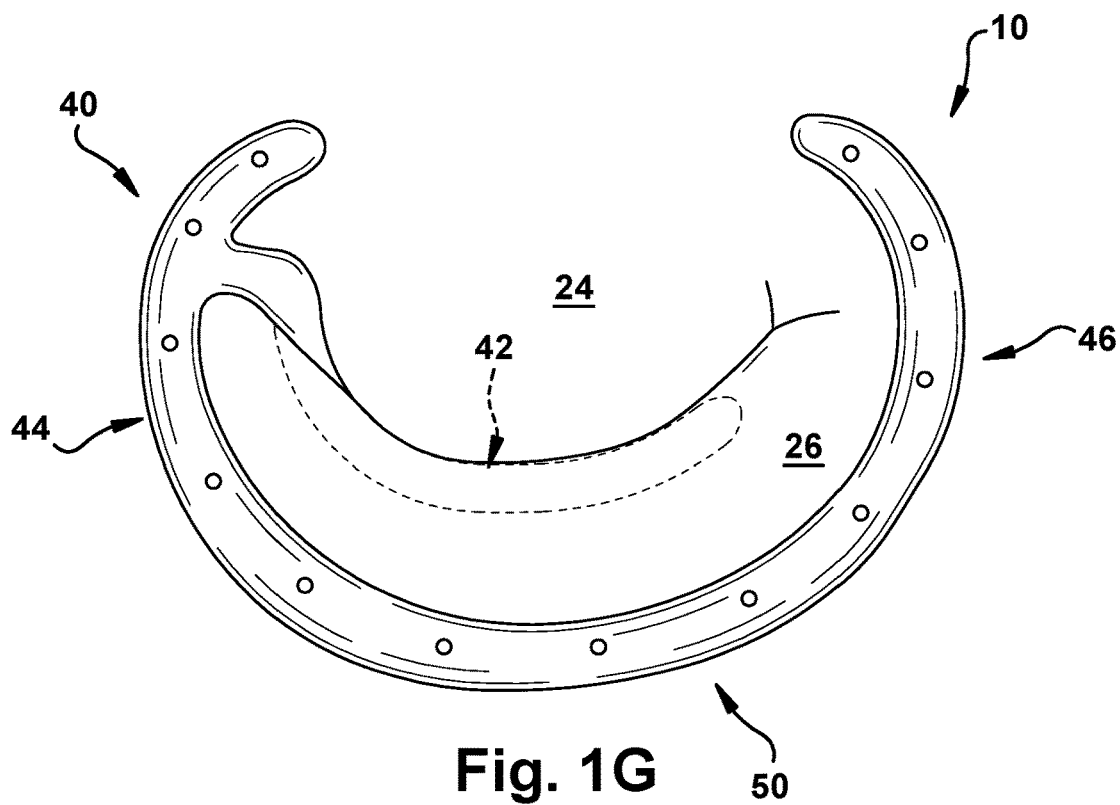
FIG. 1G is a top view showing an alternative configuration of the apparatus in FIG. 1F.
Figure 1H:
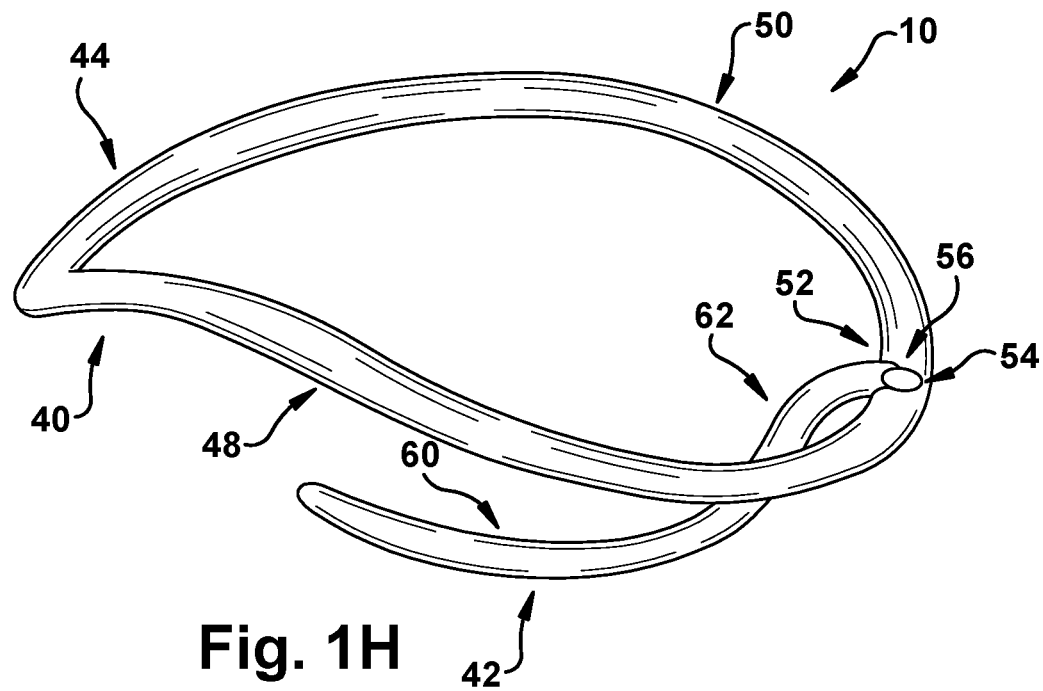
FIG. 1H is a perspective view showing an adjustment mechanism included as part of the apparatus in FIG. 1A.
Figure 1I:
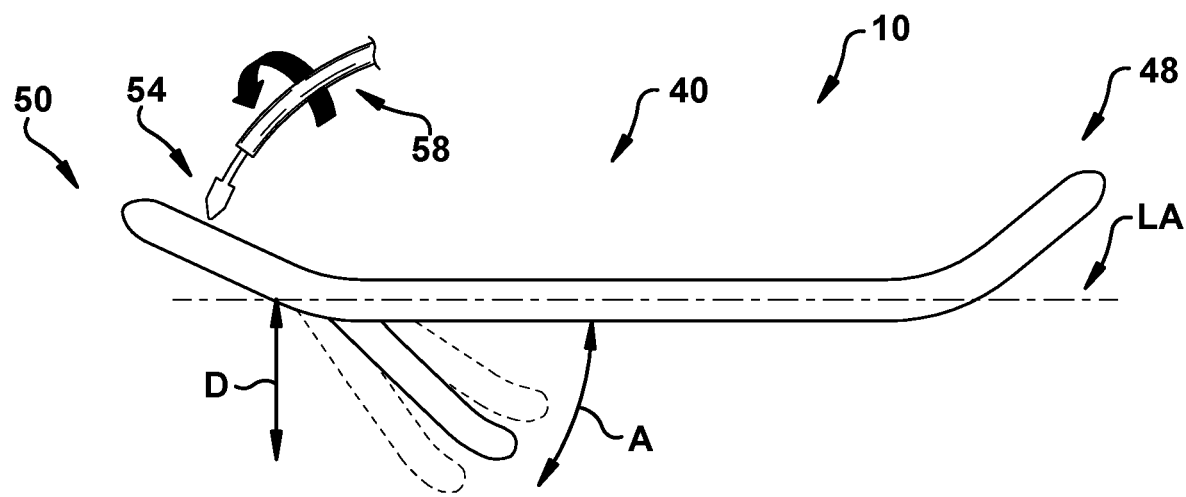
FIG. 1I is a side view of the apparatus in FIG. 1H showing manipulation of the adjustment mechanism in FIG. 1H.
Figure 1J:
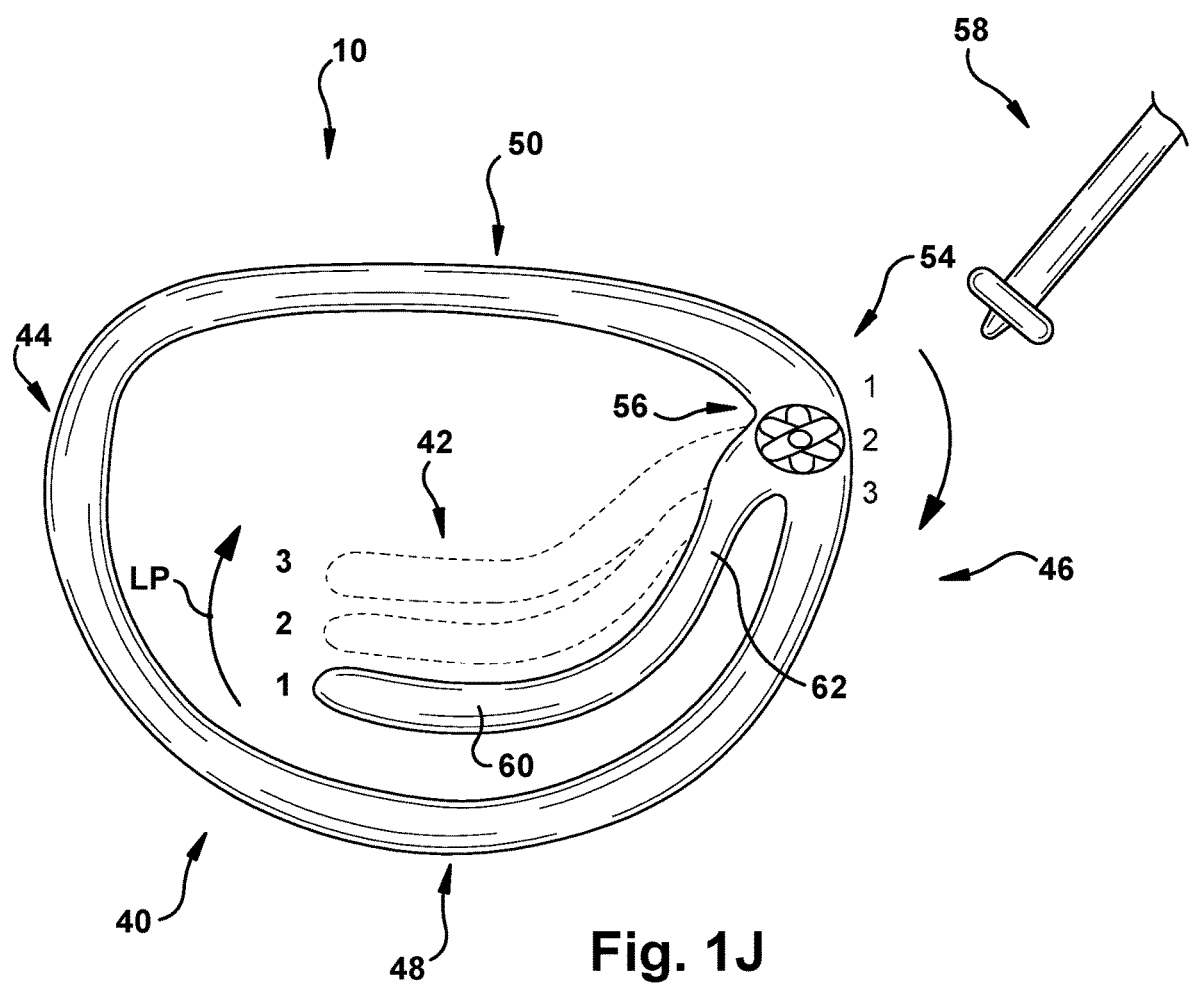
FIG. 1J is a top view of the apparatus in FIG. 1I showing manipulation of the adjustment mechanism.
Figure 1K:
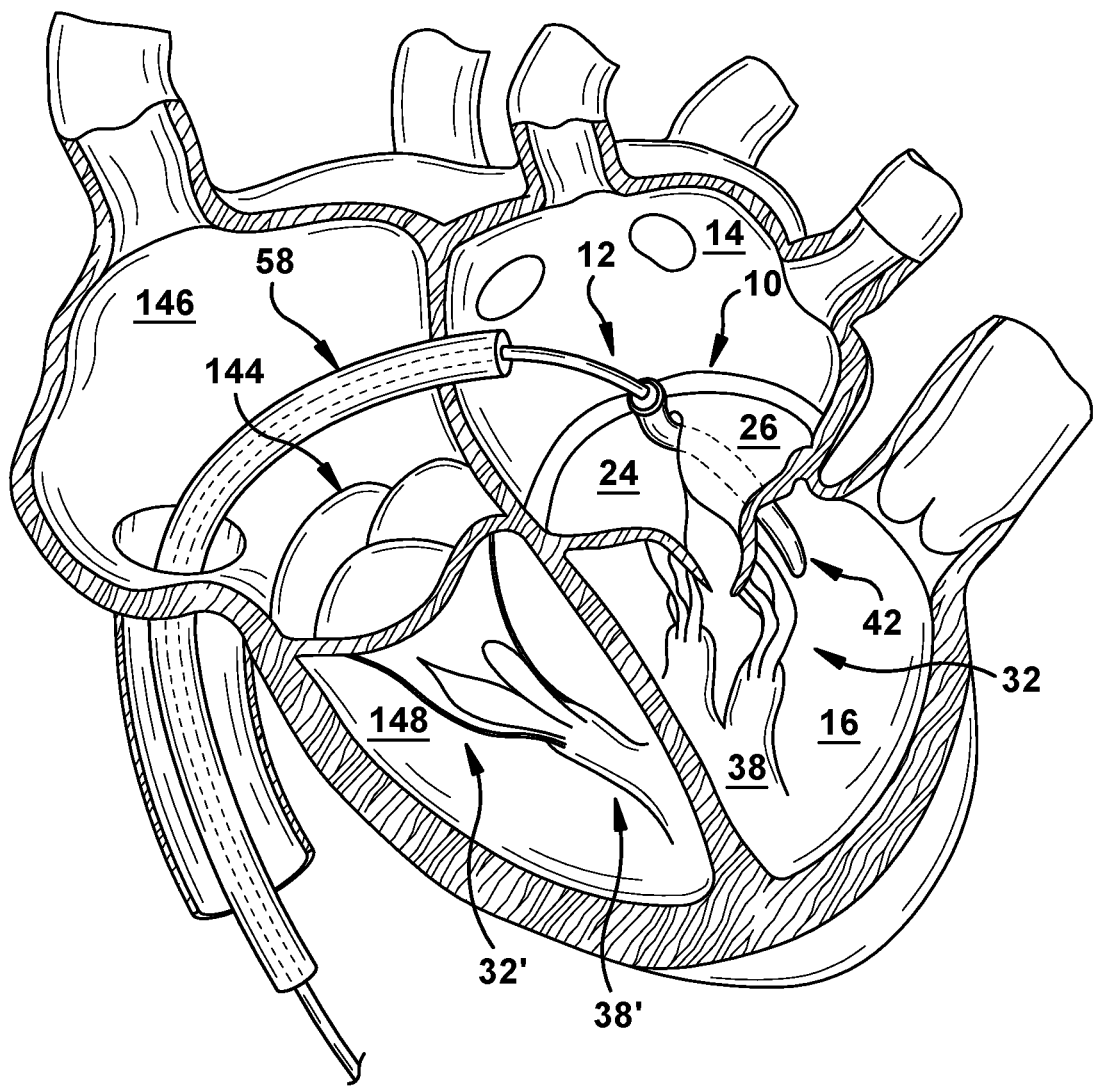
FIG. 1K is a cross-sectional view of a human heart showing percutaneous adjustment of the apparatus in FIG. 1J.

The actuation member 56 can be selectively manipulated via an adjustment tool 58 (FIGS. 1I-K). The configuration of the adjustment tool 58 will depend upon the time at which the position of the infra-annular posterior support member 42 is in need of adjustment. Where adjustment is needed during an open-heart procedure, for example, the adjustment tool 58 can be configured like a screw driver or other similar device that can be easily hand-held and manipulated by a surgeon (FIG. 1J). Alternatively, where adjustment is needed at a time following implantation of the apparatus 10, the adjustment tool 58 can be configured as a catheter to allow percutaneous adjustment of the infra-annular posterior support member 42 (FIGS. 1I and 1K).

Generally speaking, the actuation member 56 can be selectively manipulated under direct vision during open-heart surgery, using a percutaneous transeptal approach (FIG. 1K), using electromagnetic force (discussed below), and/or by echocardiographic guidance. For example, the adjustment tool 58 can be left attached to the actuation member 56 by magnetic force and externalized through the left atrial wall so that after coming off cardiopulmonary bypass, the infra-annular posterior support member 42 can be adjusted (e.g., under echocardiographic guidance) by manipulating the actuation member to achieve the optimal angle of leaflet coaptation and thereby eliminate mitral and/or tricuspid valve regurgitation. Thereafter, the magnetic force can be discontinued and the adjustment tool 58 withdrawn.

It will be appreciated that the adjustment mechanism 54 can have other configurations that enable selective adjustment of the infra-annular posterior support member 42. For example, all or only a portion of the infra-annular posterior support member 42 can be made of a shape memory material whose shape (and orientation) can be adjusted by selective application of energy thereto. If recurrent mitral and/or tricuspid regurgitation occurs over time, the adjustment mechanism 54 advantageously permits the position of the infra-annular posterior support member 42 to be adjusted without the need for additional open-heart surgeries.

The infra-annular posterior support member 42 (FIG. 1O) comprises an engaging portion 60 and an integral neck portion 62 that extends from the engaging portion to the first location 52. The engaging portion 60 is configured to contact at least one subvalvular structure, and generally has an elongated S-shaped configuration. The engaging portion 60 can have a circular cross-sectional profile, a V-shaped cross-sectional profile, and elliptical cross-sectional profile, a square-shaped cross-sectional profile, or any other geometric cross-sectional profile. The engaging portion 60 can have an arcuate configuration. As shown in FIG. 1O, for example, the engaging portion 60 can have a convex shape relative to the posterior end portion 48 of the substantially annular support member 40.

The neck portion 62 is integrally formed with the engaging portion 60. The neck portion 62 is dimensioned to extend between, or nearly between, a respective one of the commissures of the mitral valve leaflets 24 and 26. As such, the first location 52 is typically, but not necessarily, adjacent one of the commissures. As shown in FIGS. 1B-C, the neck portion 62 includes oppositely disposed first and second ends 64 and 66 that are integrally formed with the substantially annular support member 40 (i.e., at the first location 52) and the engaging portion 60, respectively. For example, the first end 64 of the neck portion 62 is integrally formed with the second intermediate portion 46 of the substantially annular support member 40.

All or only a portion of the apparatus 10 can be made of a rigid or semi-rigid material that allows manual deformation, and yet is rigid enough to withstand further deformation once implanted (i.e., when subject to normal physiological stresses). Non-limiting examples of materials for constructing the apparatus 10 can include biocompatible, medical-grade metals, such as metal alloys, plastics, Nitinol, stainless steel, titanium, pyrrolitic carbon, cobalt chromium, and the like.

All or only a portion of the apparatus 10 can be covered with a layer 68 of biocompatible material (FIG. 1E). The layer 68 of biocompatible material can comprise a synthetic material, such as DACRON, woven velour, polyurethane, PTFE, ePTFE, or heparin-coated fabric. Alternatively, the layer 68 can comprise a biological material, such as bovine or equine pericardium, a homograft, patient graft, or a cell-seeded tissue. The layer 68 can cover the inside surface of the substantially annular support member 40 and/or the infra-annular posterior support member 42, the outside surface of the substantially annular support member and/or the infra-annular posterior support member, or can be wrapped around both the inside and outside surfaces. As shown in FIG. 1E, for example, the layer 68 may be attached around the entire circumference of the substantially annular support member 40. It should be appreciated that the layer 68 can cover any portion of the apparatus 10.

As also shown FIG. 1C, the layer 68 can include at least one marker 70 to facilitate attachment of the apparatus 10 to the mitral annulus 18. The marker 70 can comprise a pre-formed hole to facilitate suture placement and/or a color indicator to indicate where sutures should be placed to stabilize of the apparatus 10 in vivo. It should be appreciated that a portion of the apparatus 10 can be enlarged or reinforced at the level of the trigones (not shown) to facilitate implantation and leaflet coaptation by including additional biocompatible layers about the desired portion(s).

At least a portion of the apparatus 10 can be treated with one or a combination of therapeutic agents capable of eluting into a cardiac chamber and/or a cardiac tissue. The therapeutic agent can be capable of preventing a variety of pathological conditions including, but not limited to, arrhythmias, thrombosis, stenosis, apoptosis, and inflammation. Accordingly, the therapeutic agent may include at least one of an anti-arrhythmic agent, anticoagulant, an antioxidant, a fibrinolytic, a steroid, an anti-apoptotic agent, an anti-overgrowth agent (i.e., capable of preventing epithelial cell overgrowth), and/or an anti-inflammatory agent. Optionally or additionally, the therapeutic agent may be capable of treating or preventing other disease or disease processes, such as microbial infections and heart failure. In these instances, the therapeutic agent may include an anti-microbial agent (e.g., an antibiotic), an inotropic agent, a chronotropic agent, and/or a biological agent, such as a cell or protein.

Another aspect of the present disclosure is illustrated in FIGS. 3A-D. The apparatus $10_a$ shown in FIGS. 3A-D is identically constructed as the apparatus 10 shown in FIGS. 1A-I, except as described below. In FIGS. 3A-D, structures that are identical as structures in FIGS. 1A-I use the same reference numbers, whereas structures that are similar but not identical carry the suffix "a". It should be appreciated that the apparatus $10_a$ can be constructed from any of the materials described above, and that the apparatus can include a layer 68 of biocompatible material and/or a therapeutic agent(s), as also described above.

Figure 3A:
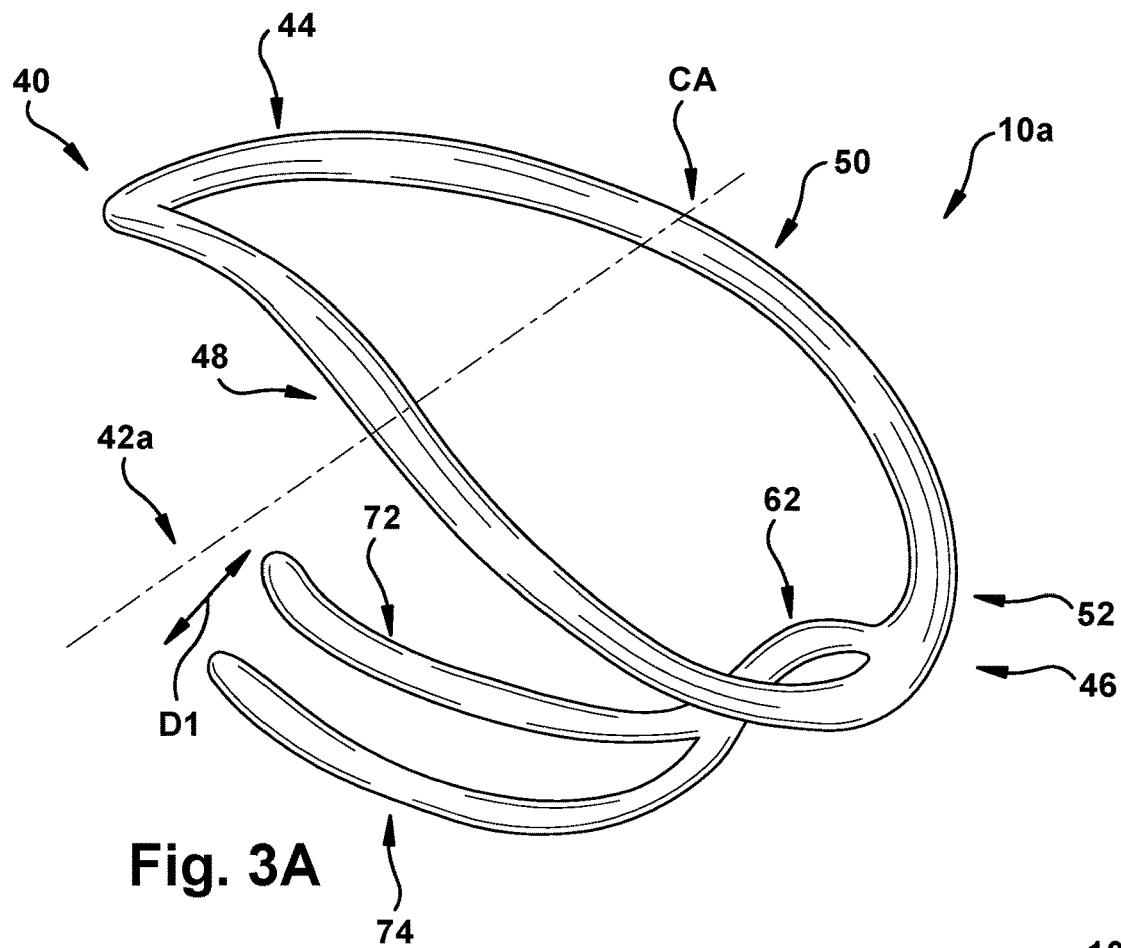
FIG. 3A is a perspective view showing an alternative configuration of the apparatus in FIG. 1A.
Figure 3B:
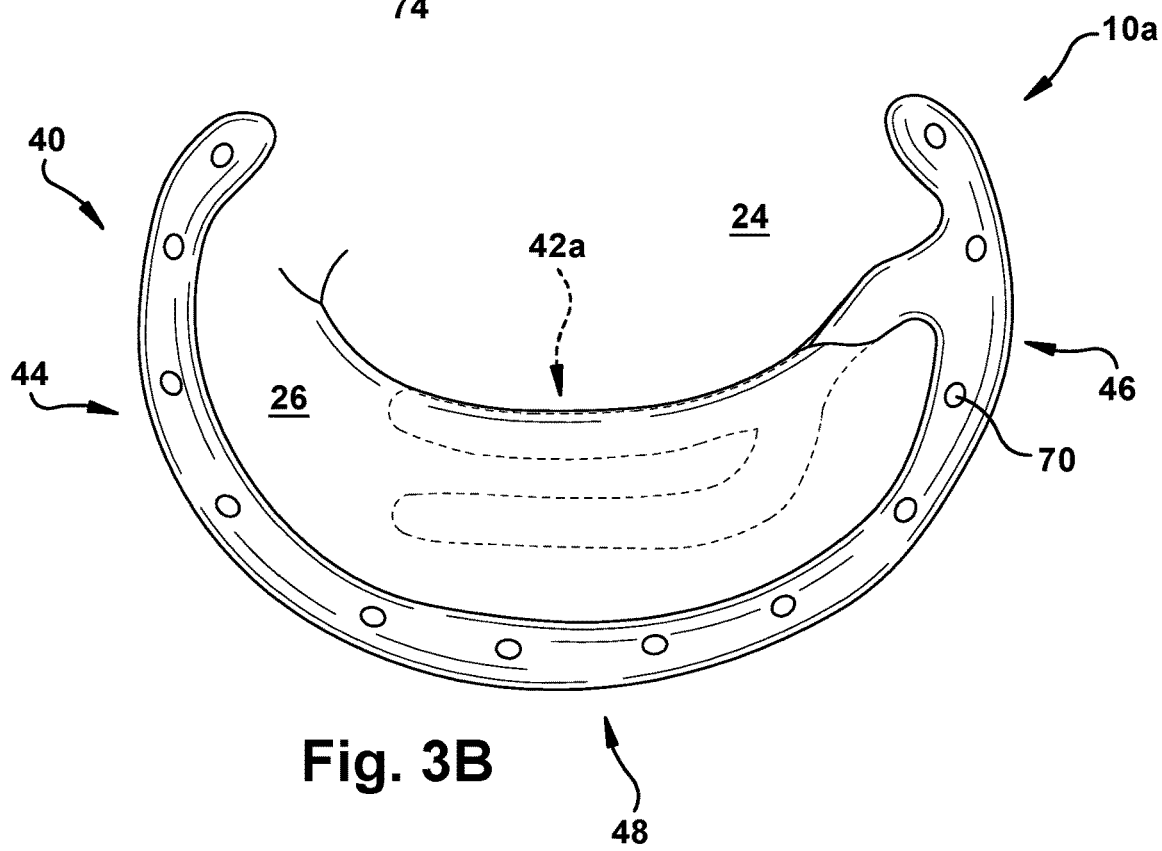
FIG. 3B is a top view showing the apparatus in FIG. 3A implanted about a diseased mitral valve.

As shown in FIGS. 3A-B, the infra-annular posterior support member $42_a$ can have a bifurcated configuration comprising spaced apart first and second engaging portions 72 and 74. The first and second engaging portions 72 and 74 can be spaced apart, and axially offset from one another (relative to a central axis CA), by a distance D1 (FIG. 3A). Generally, the distance D1 can be varied depending upon mitral valve anatomy, the particular valvular insufficiency from which a subject is suffering, as well as other factors. In particular, the distance D1 can be varied to facilitate contact between the first and second engaging portions 72 and 74 and one or more subvalvular structures. For example, the distance D1 can be varied so that the first engaging portion 72 contacts a portion of the inferior free edge 36 of the posterior mitral leaflet 26, and the second engaging portion 74 contacts a portion of the chordae tendineae 32 and/or papillary muscle(s) 38 associated with the posterior mitral leaflet.

Figure 3C:
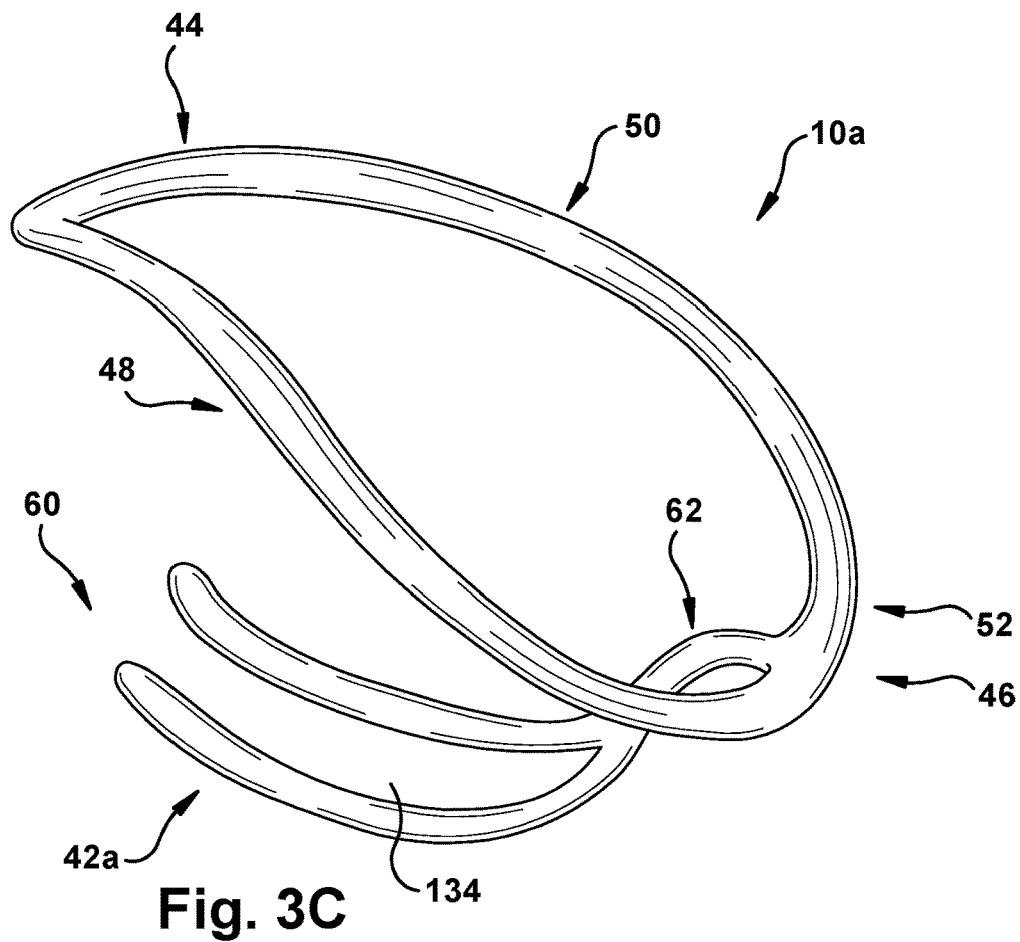
FIG. 3C is a perspective view showing an alternative configuration of the apparatus in FIG. 3A.
Figure 3D:
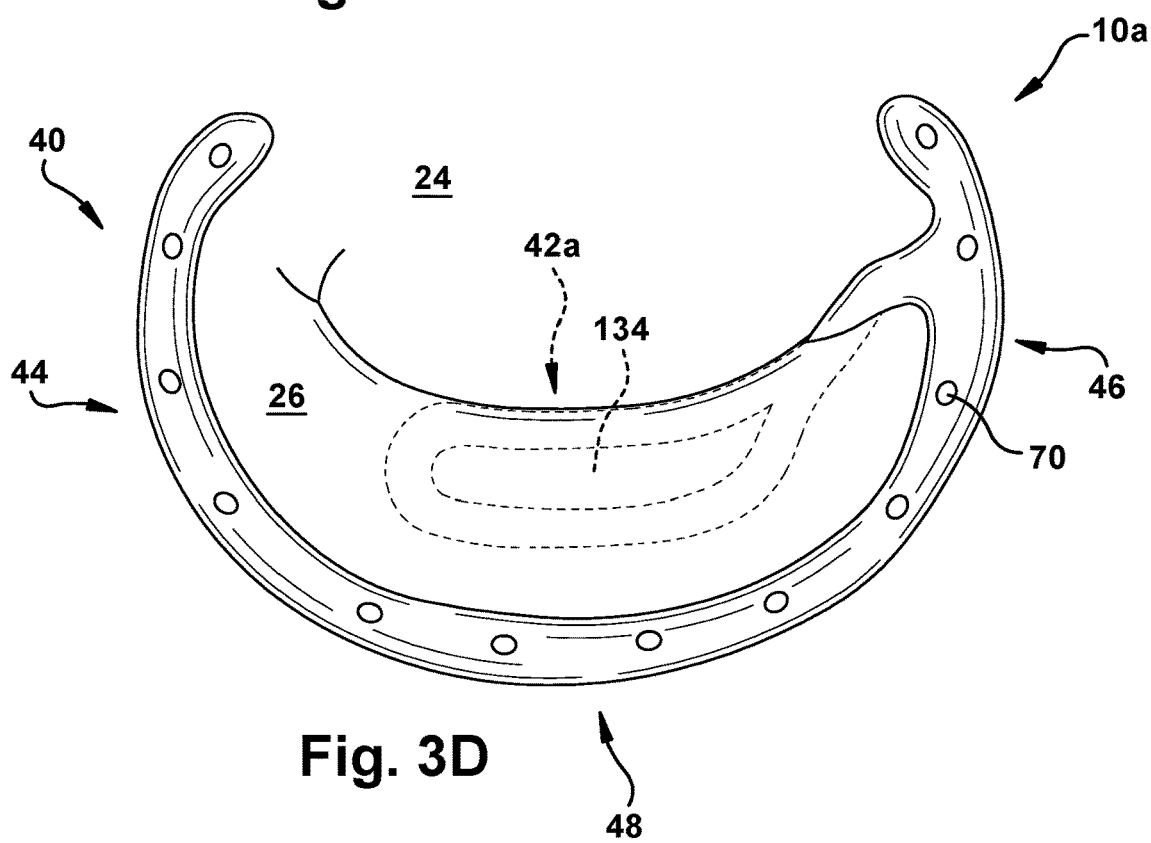
FIG. 3D is a top view showing the apparatus in FIG. 3C implanted about a diseased mitral valve.

As shown in FIGS. 3C-D, the infra-annular posterior support member 42 can alternatively have an arcuate, loop-shaped configuration that includes an aperture 134 extending therethrough. The engaging portion 60 of the infra-annular posterior support member 42 can have a concave shape relative to the anterior end portion 50 of the substantially annular support member 40. Additionally, the engaging portion 60 of the infra-annular posterior support member 42 can extend across or behind all or only a portion of at least one subvalvular structure.

Figure 4A:
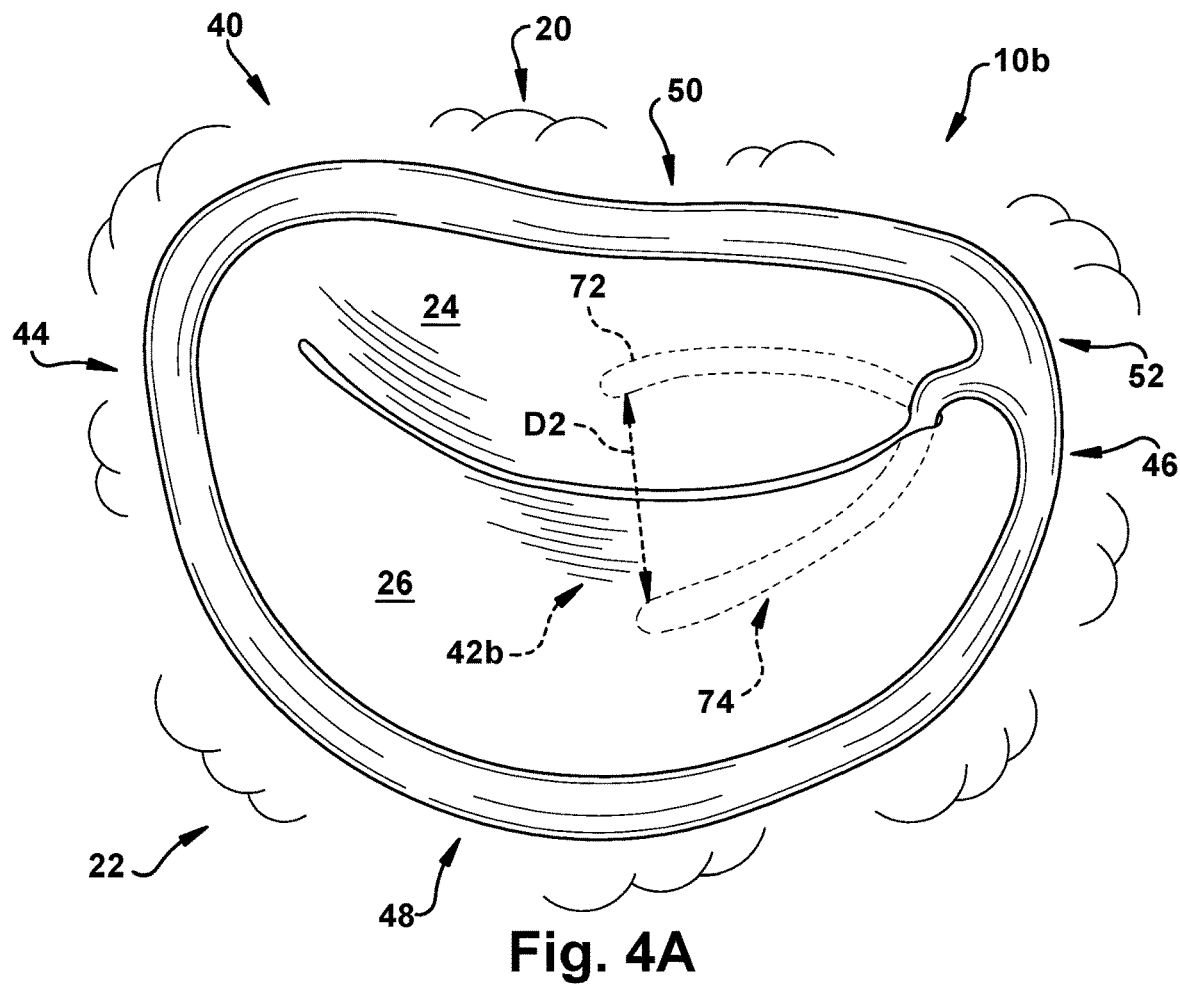
FIG. 4A is a top view showing an alternative configuration of the apparatus in FIG. 1A implanted about a diseased mitral valve.
Figure 4B:
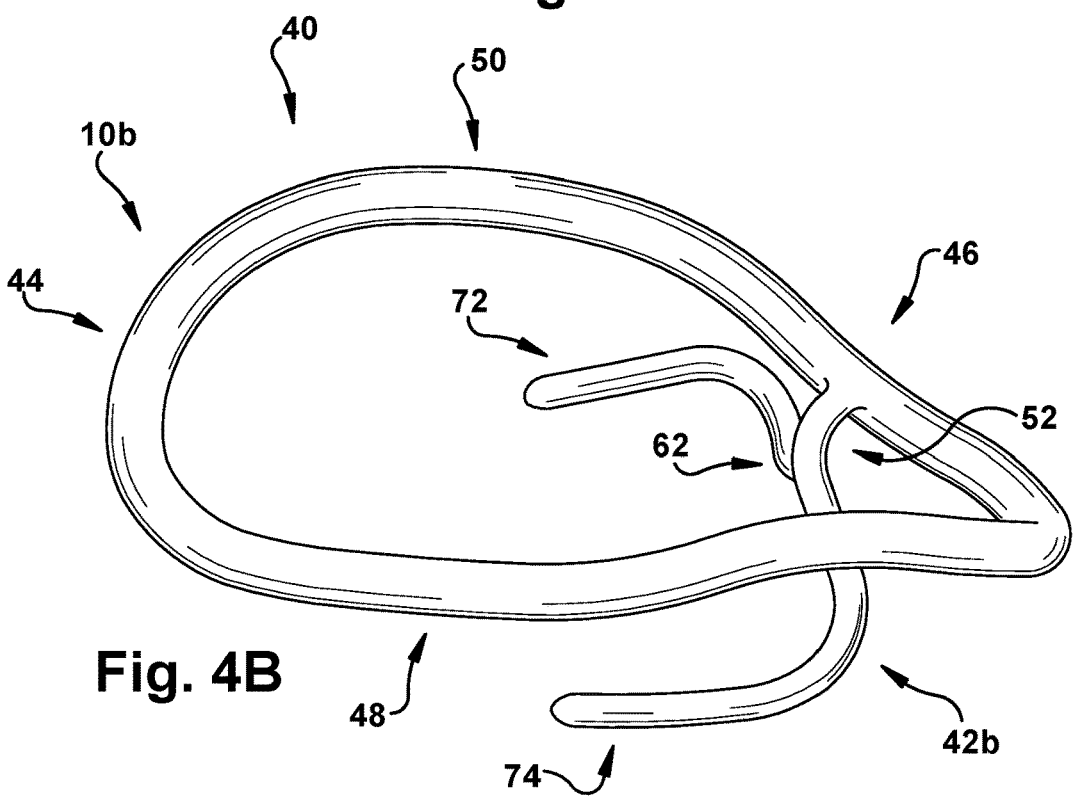
FIG. 4B is a perspective view of the apparatus in FIG. 4A.
Figure 4C:
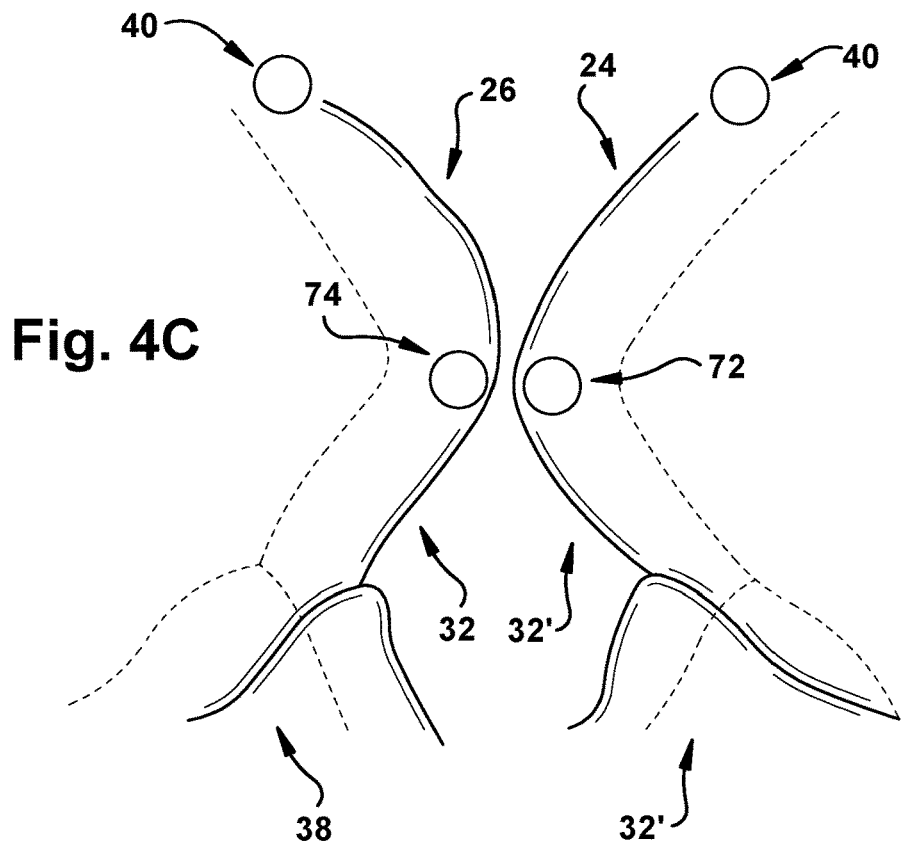
FIG. 4C is a cross-sectional view showing the apparatus of FIGS. 4A-B implanted about a diseased mitral valve.
Figure 4D:
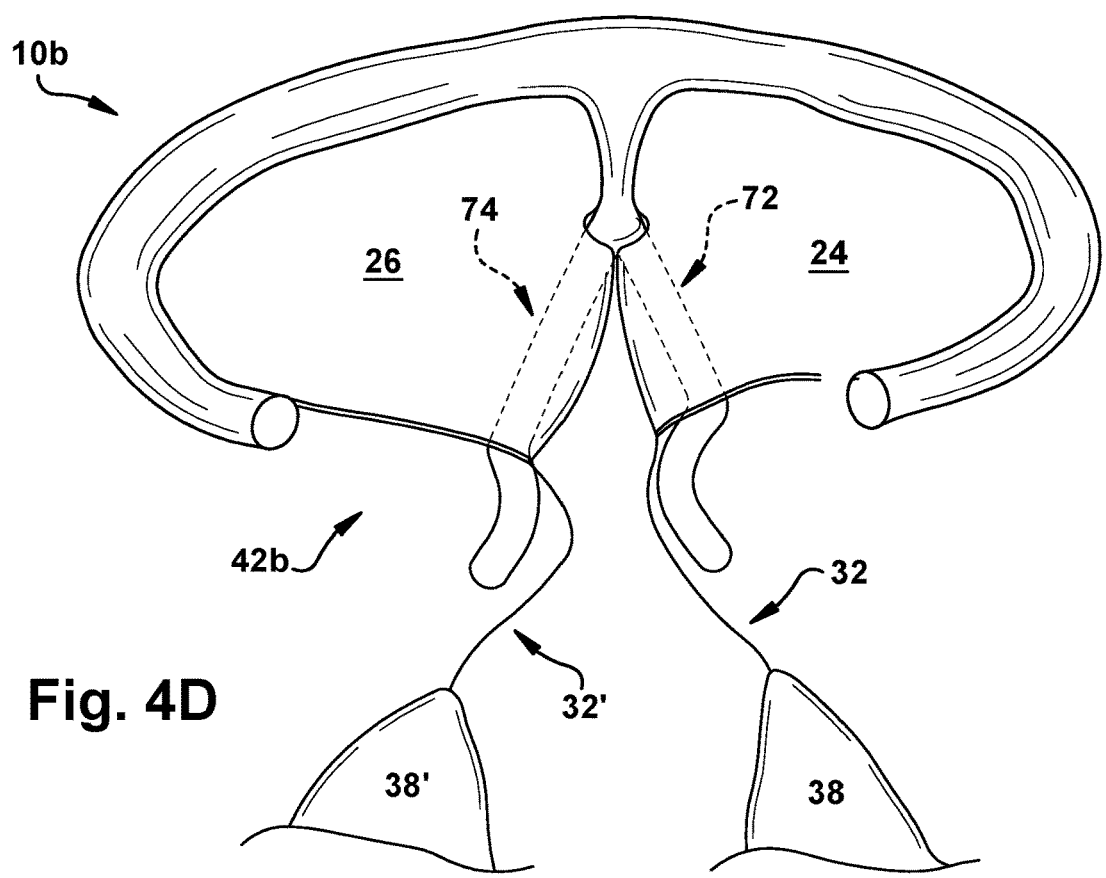
FIG. 4D is a perspective view showing the apparatus of FIGS. 4A-B implanted about a diseased mitral valve.
Figure 4E:
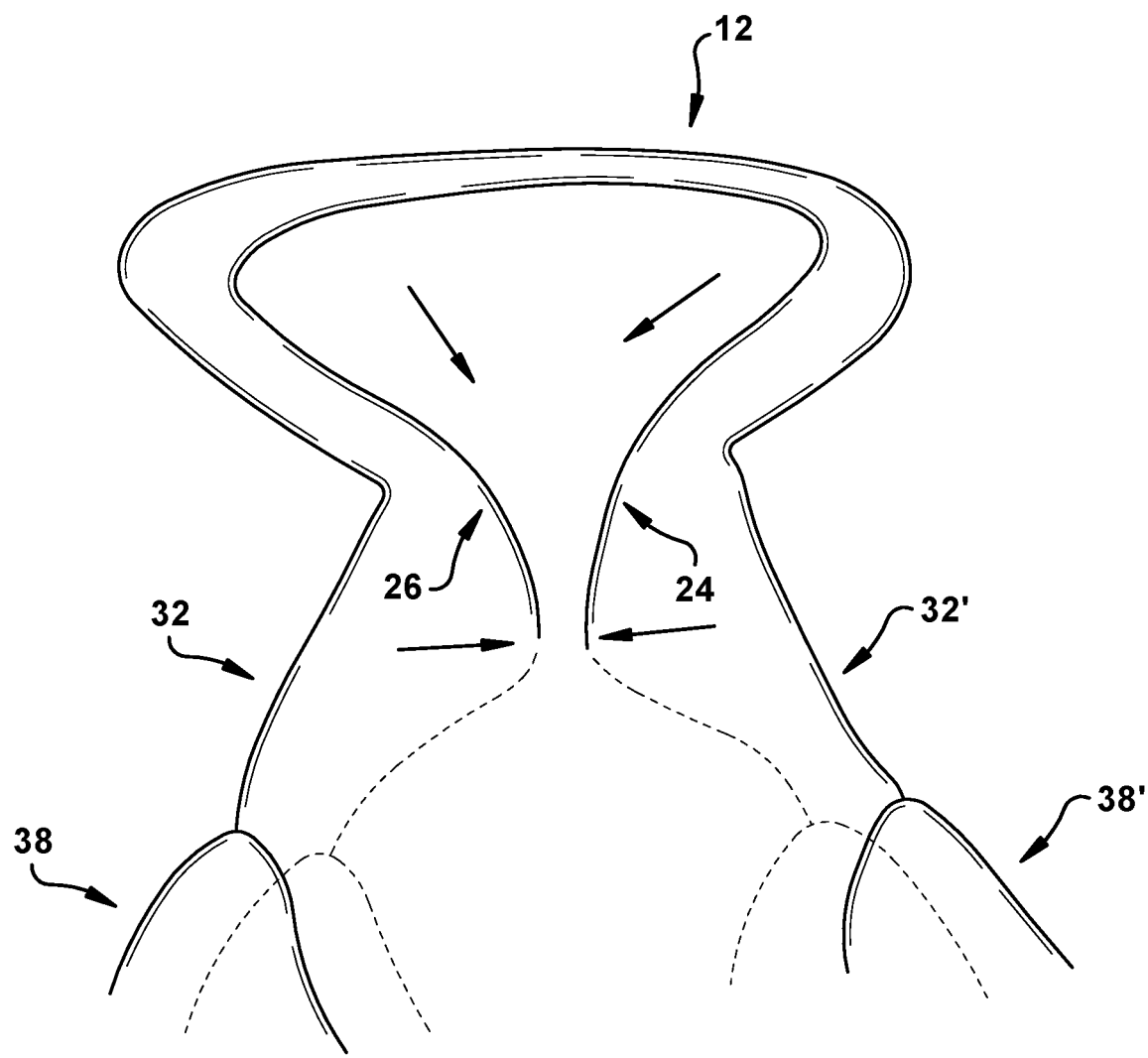
FIG. 4E is a schematic illustration showing annular and sub-annular levels of remodeling of the mitral valve in FIGS. 4C-D.

Another aspect of the present disclosure is illustrated in FIGS. 4A-E. The apparatus $10_b$ shown in FIGS. 4A-E is identically constructed as the apparatus 10 shown in FIGS. 1A-I, except as described below. In FIGS. 4A-E, structures that are identical as structures in FIGS. 1A-I use the same reference numbers, whereas structures that are similar but not identical carry the suffix "b". It should be appreciated that the apparatus $10_b$ can be constructed from any of the materials described above, and that the apparatus can include a layer 68 of biocompatible material and/or a therapeutic agent(s), as also described above As shown in FIGS. 4A-B, the infra-annular posterior support member $42_b$ can have a bifurcated configuration comprising spaced apart first and second engaging portions 72 and 74. The first and second engaging portions 72 and 74 can be spaced apart, and radially offset from one another (relative to a central axis CA), by a distance D2. Generally, the distance D2 can be varied depending upon mitral valve anatomy, the particular valvular insufficiency from which a subject is suffering, as well as other factors. In particular, the distance D2 can be varied to facilitate contact between the first and second engaging portions 72 and 74 and one or more subvalvular structures. For example, the distance D2 can be varied so that the first engaging portion 72 contacts a portion of the inferior free edge 34 of the anterior mitral leaflet 24 and/or the chordae tendineae 32' (and/or papillary muscle(s) 38') associated with the anterior mitral leaflet, and the second engaging portion 74 contacts a portion of the inferior free edge 36 of the posterior mitral leaflet 26 and/or chordae tendineae 32 (and/or papillary muscle(s) 38') associated with the posterior mitral leaflet. As shown in FIGS. 4C-E and described in more detail below, two levels of cardiac remodeling can occur when the apparatus $10_b$ is securely implanted.

Figure 5A:
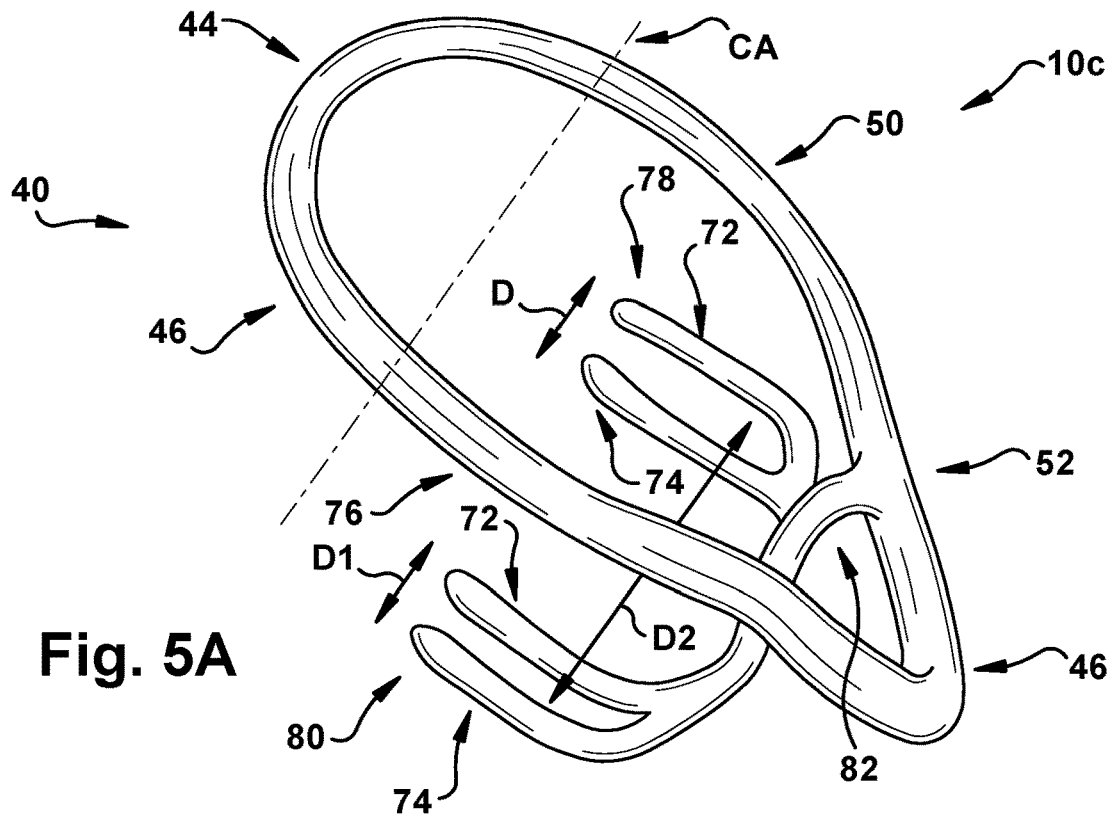
FIG. 5A is a perspective view showing an alternative configuration of the apparatus in FIGS. 4A-B.
Figure 5B:
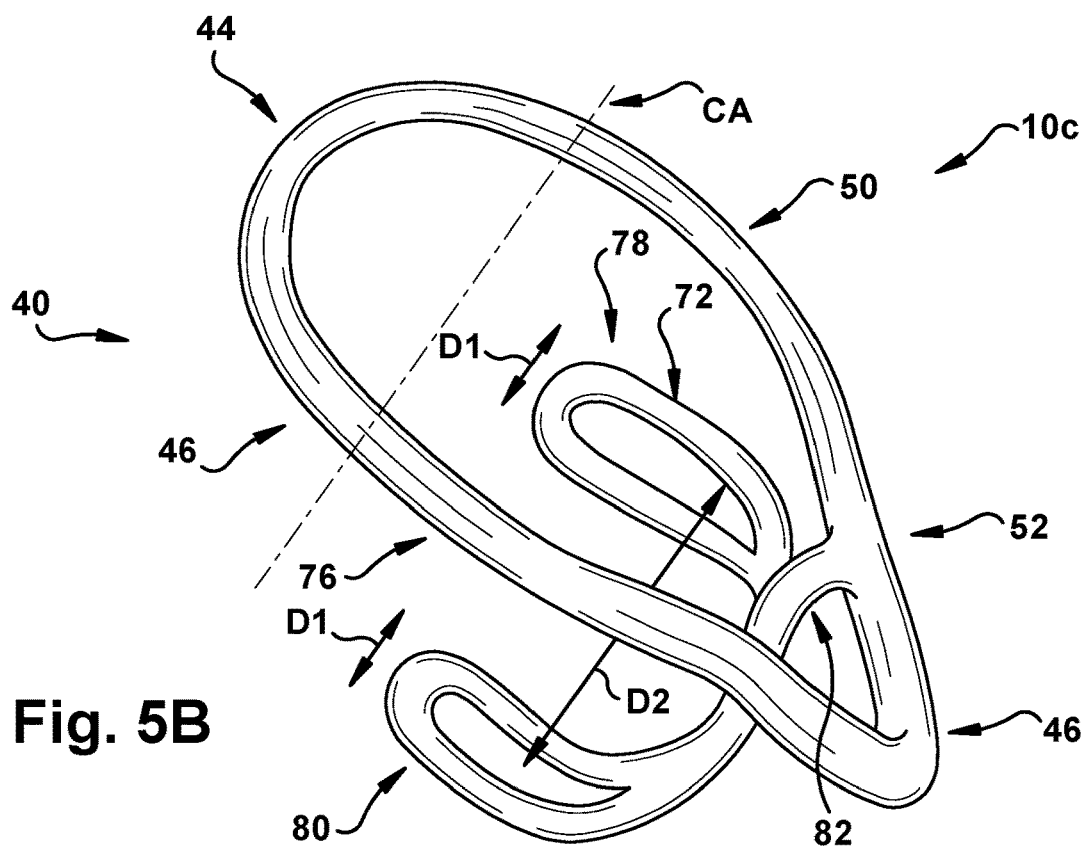
FIG. 5B is a perspective view showing another alternative configuration of the apparatus in FIG. 5A.

Another aspect of the present disclosure is illustrated in FIGS. 5A-B. The apparatus $10_c$ shown in FIGS. 5A-B is identically constructed as the apparatus 10 shown in FIGS. 1A-B, except as described below. In FIGS. 5A-B, structures that are identical as structures in FIGS. 1A-B use the same reference numbers, whereas structures that are similar but not identical carry the suffix "c". It should be appreciated that the apparatus $10_c$ can be constructed from any of the materials described above, and that the apparatus can include a layer 68 of biocompatible material and/or a therapeutic agent(s), as also described above.

The apparatus includes a Y-shaped or fork-shaped infra-annular support member 76 comprising an infra-annular anterior support portion 78 that is oppositely disposed from an infra-annular posterior support portion 80. The infra-annular anterior support portion 78 and the infra-annular posterior support portion 80 are integrally connected at a first location 52 of the substantially annular support 40 member via a common neck portion 82. The first location 52 can be on either the first or second intermediate portions 44 and 46 and located adjacent a mitral commissure.

As shown in FIG. 5A, each of the infra-annular anterior support portion 78 and the infra-annular posterior support portion 80 comprises spaced apart first and second engaging portions 72 and 74. The first and second engaging portions 72 and 74 can be spaced apart, and axially offset from one another (relative to a central axis CA), by a distance D1. Alternatively, each of the infra-annular anterior support portion 78 and the infra-annular posterior support portion 80 can have an elongated, loop-shaped configuration (FIG. 5B). The infra-annular anterior support portion 78 is radially spaced apart from the infra-annular posterior support portion 80 by a distance D2. It will be appreciated that the distance D1 and/or distance D2 can be varied to optimize leaflet coaptation.

Figure 6A:
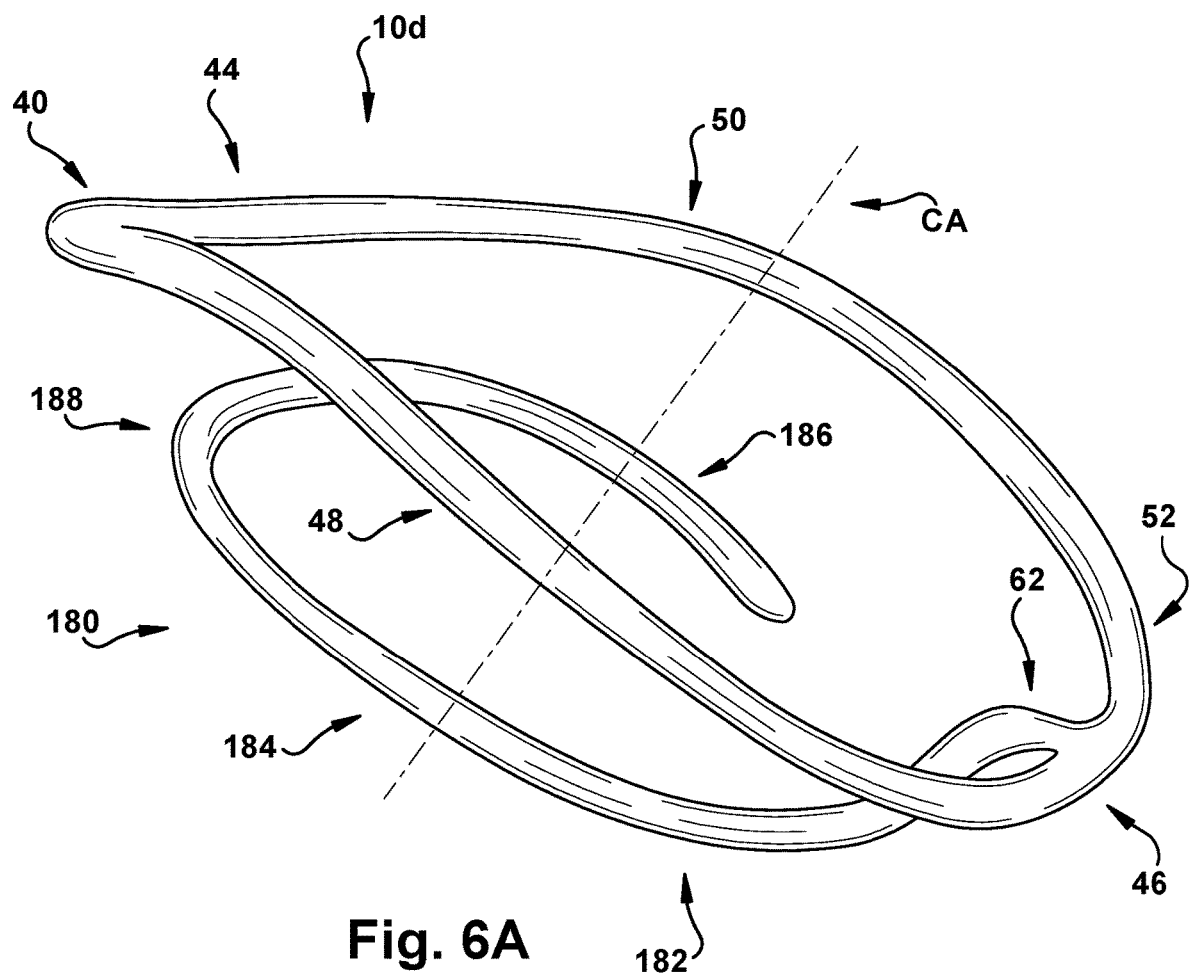
FIG. 6A is a perspective view showing an alternative configuration of the apparatus in FIG. 1A.
Figure 6B:
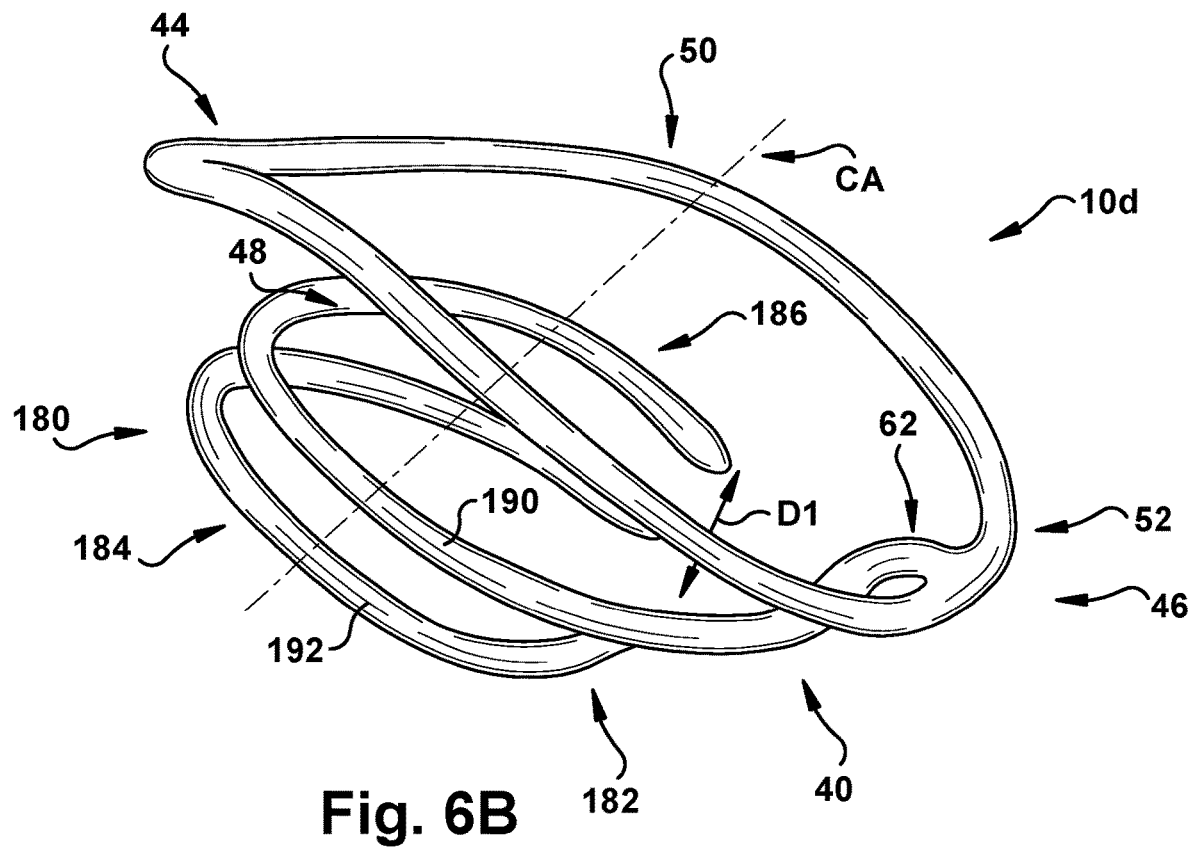
FIG. 6B is a perspective view showing an alternative configuration of the apparatus in FIG. 6A.
Figure 6C:
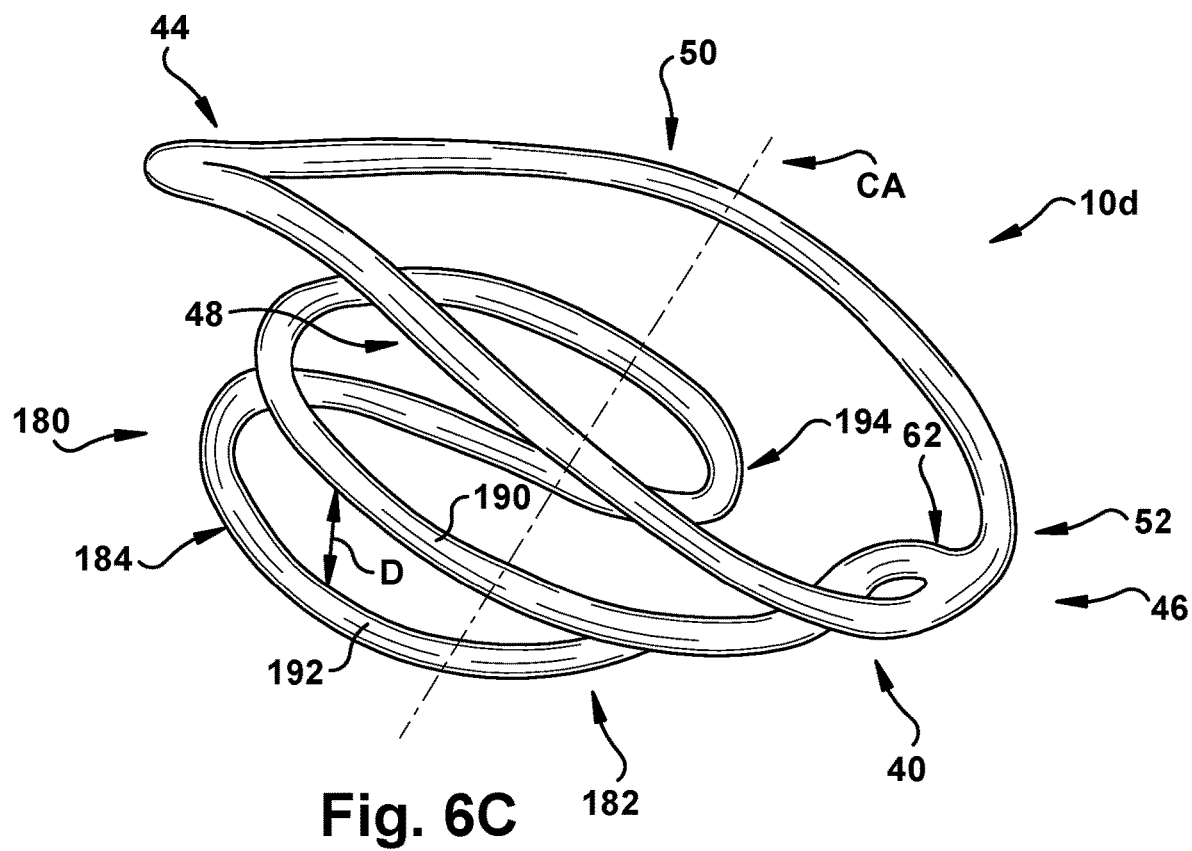
FIG. 6C is a perspective view showing another alternative configuration of the apparatus in FIG. 6A.

Another aspect of the present disclosure is illustrated in FIGS. 6A-C. The apparatus $10_d$ shown in FIGS. 6A-C is identically constructed as the apparatus 10 shown in FIGS. 1A-I, except as described below. In FIGS. 6A-C, structures that are identical as structures in FIGS. 1A-I use the same reference numbers, whereas structures that are similar but not identical carry the suffix "d". It should be appreciated that the apparatus $10_d$ can be constructed from any of the materials described above, and that the apparatus can include a layer 68 of biocompatible material and/or a therapeutic agent(s), as also described above.

As shown in FIGS. 6A-C, the apparatus $10_d$ comprises a substantially annular support member 40 and an infra-annular posterior and anterior support member 180 that is securely connected thereto. The substantially annular support member 40 can be entirely annular and comprise a first intermediate portion 44, a second intermediate portion 46, a posterior end portion 48 extending between the first and second intermediate portions, and an anterior end portion 50 extending between the first and second intermediate portions opposite the posterior end portion. Alternatively, the substantially annular support member 40 can be partly annular and comprise a first intermediate portion 44, a second intermediate portion 46, and a posterior end portion 48 extending between the first and second intermediate portions.

The anterior end portion 50 and the posterior end portion 48 are dimensioned for attachment to the anterior and posterior portions 20 and 22 of the mitral annulus 18, respectively. For example, the posterior end portion 48, the first intermediate portion 44, and the second intermediate portion 46 form a continuous arc so that the posterior end portion has a concave shape relative to the anterior end portion 50. Similarly, the anterior end portion 50, the first intermediate portion 44, and the second intermediate portion 46 form a continuous arc so that the anterior end portion has a convex shape relative to the posterior end portion 48. Like the apparatus 10 shown in FIG. 1D, the substantially annular support member 40 of the apparatus $10_d$ also includes a longitudinal axis LA. The substantially annular support member 40 can have a rigid or semi-rigid configuration.

The infra-annular posterior and anterior support member 180 is dimensioned, shaped, and configured to extend below the posterior and anterior mitral leaflets 26 and 24 and across or behind at least one subvalvular structure when the apparatus $10_d$ is implanted on or about the mitral annulus 18. The infra-annular posterior and anterior support member 180 is securely and directly connected to the substantially annular support member 40 at a first location 52. As shown in FIG. 6A, for example, the infra-annular posterior and anterior support member 180 is securely and directly connected to the second intermediate portion 46. Although not shown, it will be appreciated that the infra-annular posterior and anterior support member 180 can alternatively be securely and directly connected to the first intermediate portion 44.

The infra-annular posterior and anterior support member 180 comprises a hook-shaped engaging portion 182 that is integrally and directly connected to the substantially annular support member 40 via a neck portion 62. The engaging portion 182 further comprises a first engaging portion 184, a second engaging portion 186, and a bend portion 188 extending between the first and second engaging portions. Each of the first and second engaging portions 184 and 186 has a continuous, arc-shaped (or arcuate) configuration configured to extend across or behind at least one subvalvular structure. The first and second engaging portions 184 and 186 can have concave and convex shapes (respectively) relative to the anterior end portion 50 of the substantially annular support member 40.

The first engaging portion 184 is configured to extend across or behind at least one subvalvular structure, such as: an inferior aspect of the posterior leaflet 26, such as an inferior free edge 36 of the posterior leaflet; chordae tendineae 32 associated with the posterior leaflet; one or more papillary muscles 38 associated with the tendineae chordae of the posterior leaflet; and combinations thereof. Additionally, the second engaging portion 186 is configured to extend across or behind at least one subvalvular structure, such as: an inferior aspect of the anterior leaflet 24, such as an inferior free edge 34 of the anterior leaflet; chordae tendineae 32' associated with the anterior leaflet; one or more papillary muscles 38' associated with the chordae tendineae of the anterior leaflet; and combinations thereof.

The first and second engaging portions 184 and 186 can be located in the same lateral plane (i.e., a plane that extends below and parallel or substantially parallel to the longitudinal axis LA) or, alternatively, offset from one another relative to a central axis CA. In this manner, the first and second engaging portions 184 and 186 can be positioned to contact the same or different corresponding subvalvular structures. Where the first and second engaging portions 184 and 186 are offset from one another, for example, the first engaging portion can be configured to extend across or behind an inferior aspect of the posterior leaflet 26 (e.g., an inferior free edge 36 of the posterior leaflet), and the second engaging portion can be configured to extend across or behind chordae tendineae 32' associated with the anterior leaflet 24.

Alternative configurations of the infra-annular posterior and inferior support member 180 are illustrated in FIGS. 6B-C. As shown in FIG. 6B, the engaging portion 182 of the infra-annular posterior and anterior support member 180 can have a bifurcated configuration comprising spaced apart first and second engaging members 190 and 192. The first and second engaging members 190 and 192 can be spaced apart, and axially offset from one another (relative to a central axis CA), by a distance D1. Generally, the distance D1 can be varied depending upon mitral valve anatomy, the particular valvular insufficiency from which a subject is suffering, as well as other factors. In particular, the distance D1 can be varied to facilitate contact between the first and second engaging members 190 and 192 and one or more subvalvular structures. Each of the first and second engaging members 190 and 192 includes first and second engaging portions 184 and 186, as described above.

As shown in FIG. 6C, the engaging portion 182 of the infra-annular posterior and anterior support member 180 can alternatively have an arcuate, loop-shaped configuration that includes an aperture 134 extending therethrough. The loop-shaped engaging portion 182 can comprise first and second engaging members 190 and 192 that join at a common arcuate bend 194. The first and second engaging members 190 and 192 can be spaced apart, and axially offset from one another (relative to a central axis CA), by a distance D1. Generally, the distance D1 can be varied depending upon mitral valve anatomy, the particular valvular insufficiency from which a subject is suffering, as well as other factors.

It will be appreciated that the apparatus $10_d$ can additionally or optionally include other features as the apparatus 10 shown in FIGS. 1A-B and described above. For example, the apparatus $10_d$ can include: an adjustable mechanism 54; a layer 68 of biocompatible material; at least one marker 70 to facilitate attachment of the apparatus to the mitral annulus 18; and/or one or a combination of therapeutic agents.

Figure 7A:
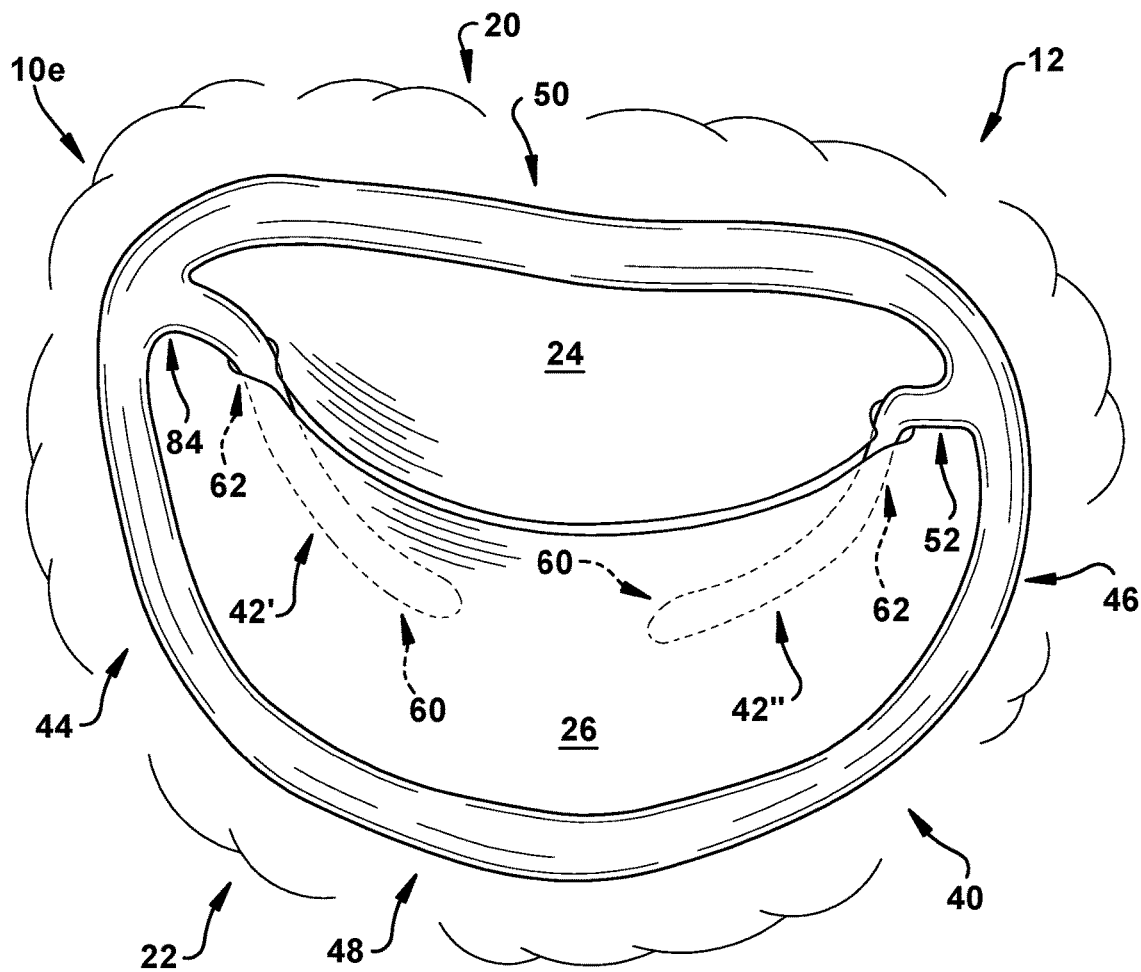
FIG. 7A is a top view showing an alternative configuration of the apparatus in FIG. 1A.
Figure 7B:
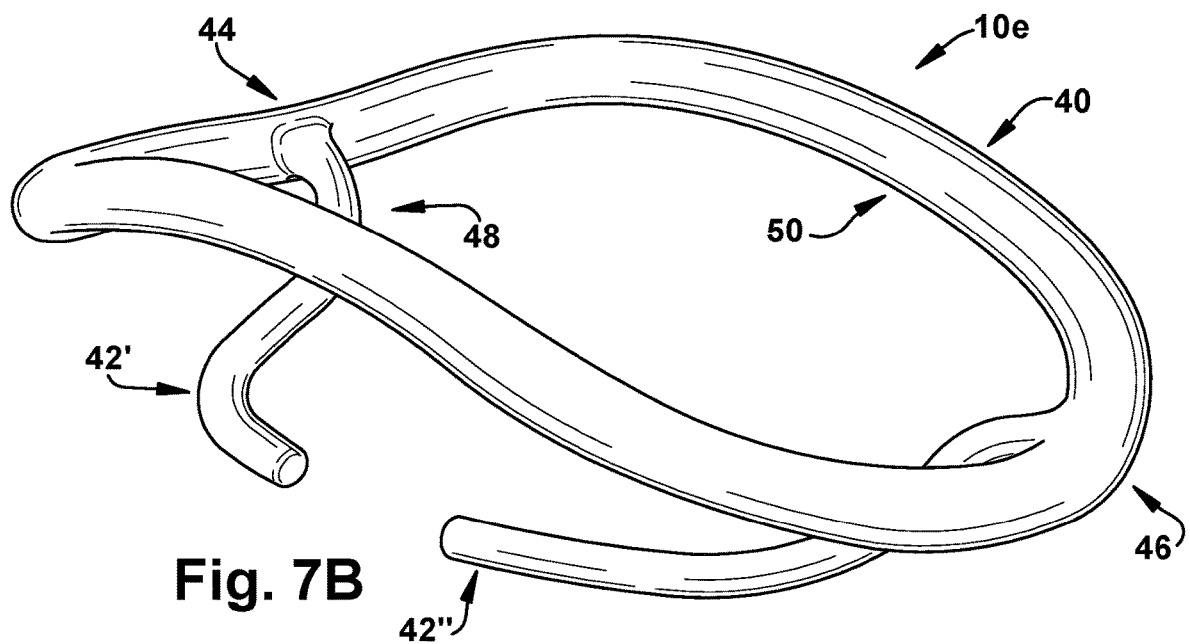
FIG. 7B is a perspective view of the apparatus in FIG. 7A.
Figure 7C:
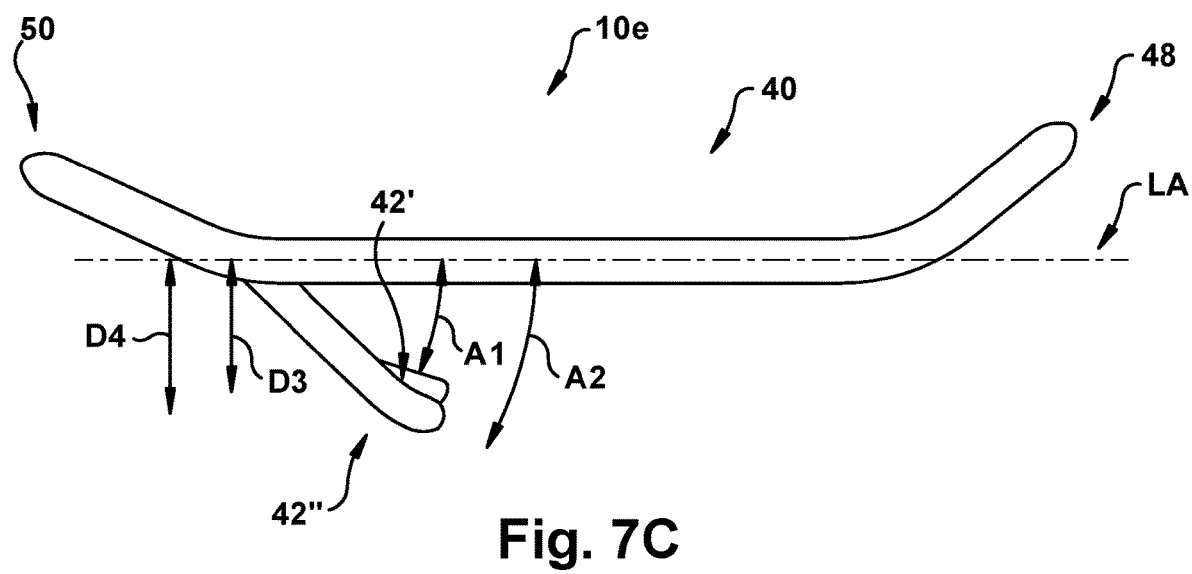
FIG. 7C is a side view of the apparatus in FIGS. 7A-B.

Another aspect of the present disclosure is illustrated in FIGS. 7A-C. The apparatus $10_e$ shown in FIGS. 7A-C is identically constructed as the apparatus 10 shown in FIGS. 1A-I, except as described below. In FIGS. 7A-C, structures that are identical as structures in FIGS. 1A-I use the same reference numbers, whereas structures that are similar but not identical carry the suffix "e". It should be appreciated that the apparatus $10_e$ can be constructed from any of the materials described above, and that the apparatus can include a layer 68 of biocompatible material and/or a therapeutic agent(s), as also described above.

As shown in FIGS. 7A-C, the apparatus $10_e$ comprises a substantially annular support member 40, a first infra-annular posterior support member 42', and a second infra-annular posterior support member 42". The substantially annular support member 40 can be entirely annular and comprise a first intermediate portion 44, a second intermediate portion 46, a posterior end portion 48 extending between the first and second intermediate portions, and an anterior end portion 50 extending between the first and second intermediate portions opposite the posterior end portion. Alternatively, the substantially annular support member 40 can be partly annular and comprise a first intermediate portion 44, a second intermediate portion 46, and a posterior end portion 48 extending between the first and second intermediate portions.

The anterior end portion 50 and the posterior end portion 48 are dimensioned for attachment to the anterior and posterior portions 20 and 22 of the mitral annulus 18, respectively. For example, the posterior end portion 48, the first intermediate portion 44, and the second intermediate portion 46 form a continuous arc so that the posterior end portion has a concave shape relative to the anterior end portion 50. Similarly, the anterior end portion 50, the first intermediate portion 44, and the second intermediate portion 46 form a continuous arc so that the anterior end portion has a convex shape relative to the posterior end portion 48. As shown in FIG. 7C, the substantially annular support member 40 also includes a longitudinal axis LA. The substantially annular support member 40 can have a rigid or semi-rigid configuration.

The first and second infra-annular posterior support members 42' and 42" are dimensioned, shaped, and configured to extend below the posterior mitral leaflet 26 and across or behind at least one subvalvular structure when the apparatus $10_e$ is implanted on or about the mitral annulus 18. The first infra-annular posterior support member 42' is securely and directly connected to the substantially annular support member 40 at a first location 52, and the second infra-annular posterior support member 42" is securely and directly connected to the substantially annular support member at a second location 84 that is different than the first location. As shown in FIG. 7A, for example, the first infra-annular posterior support member 42' is securely and directly connected to the first intermediate portion 44, and the second infra-annular posterior support member 42" is securely and directly connected to the second intermediate portion 46.

Each of the first and second infra-annular posterior support members 42' and 42" extends at an angle A1 and A2 (FIG. 7C), respectively, and at a distance D3 and D4 below the longitudinal axis LA of the substantially annular support member 40. The angle A1 and A2 of each of the first and second infra-annular posterior support members 42' and 42", respectively, is such that the first and second infra-annular posterior support members facilitate optimal leaflet coaptation. In one example of the present disclosure, the angle A1 and A2 of one or both of the first and second infra-annular posterior support members 42' and 42" can be about 10° to about 60° (e.g., about 30°). It will be appreciated that the angle A1 and A2 can be the same or different. Similarly, the distance D3 and D4 is such that a portion of each of the first and second infra-annular posterior support members 42' and 42", respectively, extends below the posterior mitral leaflet 26 to enable the first and second infra-annular first and second posterior support members to facilitate optimal leaflet coaptation. It will also be appreciated that the distance D3 and D4 can be the same or different.

Each of the first and second infra-annular posterior support members 42' and 42" is configured similarly or identically as the infra-annular posterior support member 42 shown in FIGS. 1A-B and described above. For example, each of the first and second infra-annular posterior support members 42' and 42" comprises an engaging portion 60 (FIG. 7A) and an integral neck portion 62 that extends from the engaging portion to the first location 52. The engaging portion 60 of each of the first and second infra-annular posterior support members 42' and 42" can have an arcuate shape such that each of the engaging portions has a concave shape relative to the anterior end portion 50 of the substantially annular support member 40.

It will be appreciated that the apparatus 10$_e$ can additionally or optionally include other features as the apparatus 10 shown in FIGS. 1A-B and described above. For example, the apparatus 10$_e$ can include: an adjustable mechanism 54; a layer 68 of biocompatible material; at least one marker 70 to facilitate attachment of the apparatus to the mitral annulus 18; and/or one or a combination of therapeutic agents.

Another aspect of the present disclosure is illustrated in FIGS. 8A-9C and includes a method for treating regurgitation of blood flow through a regurgitant mitral valve 12. Although the method of the present disclosure will be described below using the apparatus 10$_e$ illustrated in FIGS. 7A-B, it should be appreciated that any of the apparatus described herein may also be used to treat regurgitation of blood flow through a diseased mitral valve. For example, the apparatus 10$_f$ shown in FIGS. 13A-B may be used to treat a dysfunctional (e.g., restricted motion) anterior mitral valve leaflet 24.

As described above, the apparatus 10$_e$ (FIGS. 7A-B) comprises a D-shaped annular support member 40 having a saddle-shaped, 3D configuration dimensioned for attachment to the mitral annulus 18. The apparatus 10$_e$ additionally includes oppositely disposed first and second infra-annular posterior support members 42' and 42" that are integrally formed with the first and second intermediate portions 44 and 46 of the substantially annular support member 40, respectively. Although not shown in FIGS. 7A-B, it will be appreciated that all or only a portion of the apparatus 10$_e$ (e.g., the substantially annular support member 40) can be covered with a layer 68 of biocompatible material, such as a sewing ring.

To treat the regurgitant mitral valve 12, the dimensions of the mitral valve are first obtained to determine optimal dimensions for the apparatus 10$_e$. Sizing of the mitral valve 12 can be performed using a valve sizing device. Examples of valve sizing devices are known in the art and can include commercially-available sizers, such as those from the ATS OPEN PIVOT STANDARD SIZER series (ATS Medical, Inc. Minneapolis, Minn.). In one example of the present disclosure, the dimensions of the mitral valve 12 can be determined using the valve sizing device 86 disclosed in U.S. Patent Publication No. 2009/0132036 A1 to Navia (hereinafter, "the '036 application"), which is hereby incorporated by reference in its entirety.

Figure 8A:
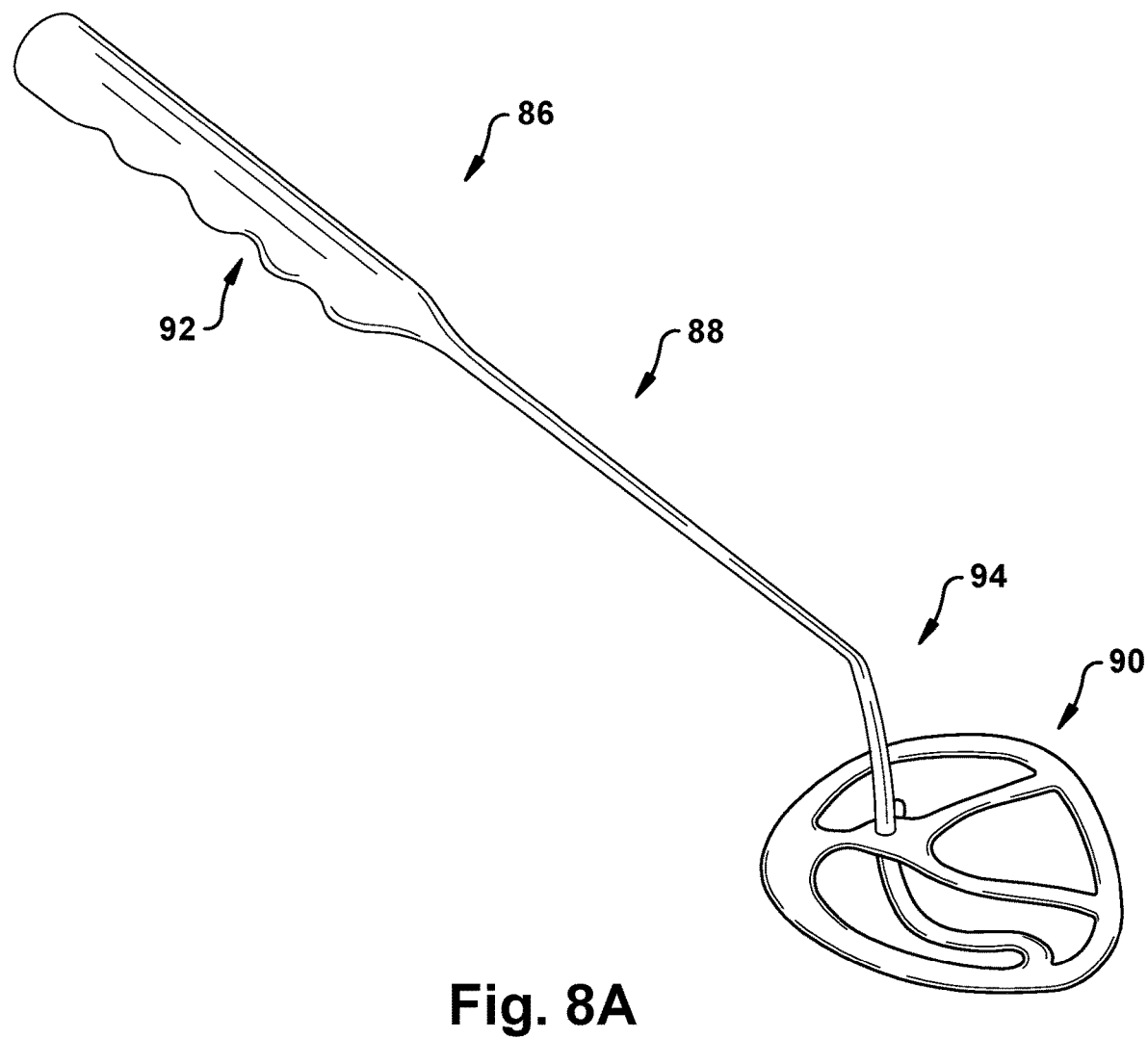
FIG. 8A is a perspective view of a sizing device constructed in accordance with another aspect of the present disclosure.
Figure 8B:
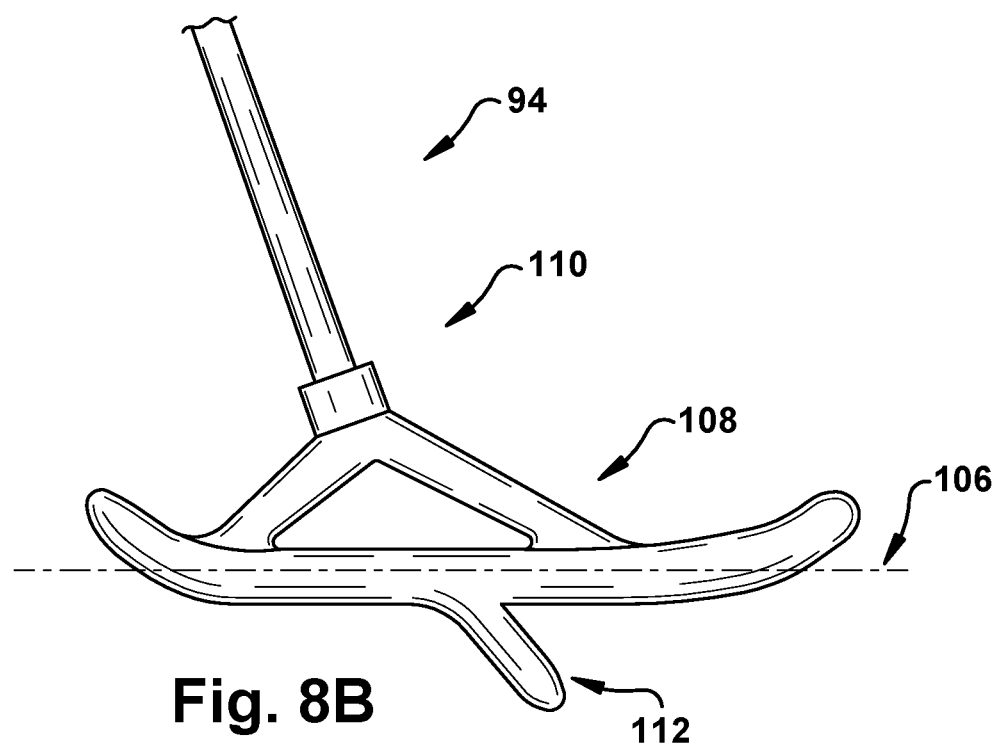
FIG. 8B is a magnified side view showing a distal portion of the sizing device in FIG. 8A.
Figure 8C:
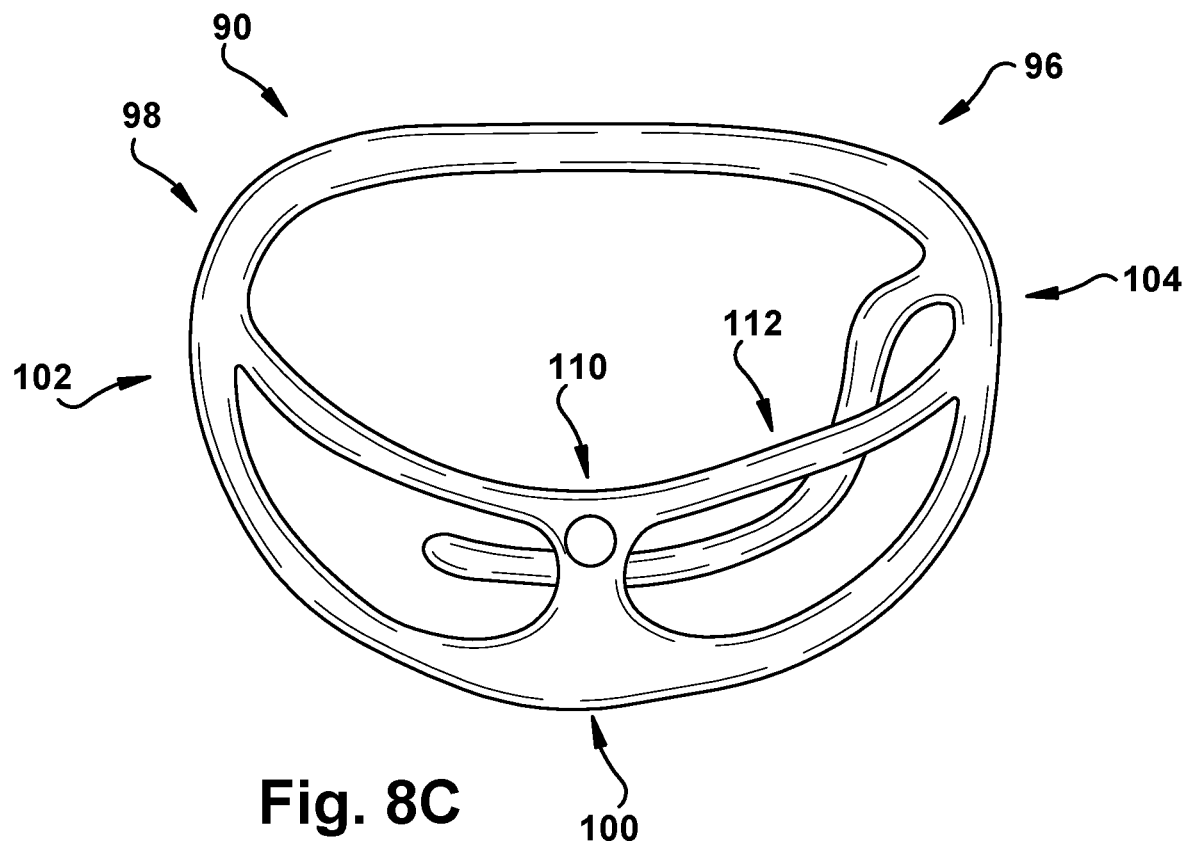
FIG. 8C is a top view of a sizing member comprising the sizing device in FIG. 8A.

As shown in FIGS. 8A-C, the sizing device 86 comprises a handle member 88 securely attached to a sizing member 90. The handle member 88 includes a handle 92 fluidly connected to a distal attachment portion 94. The handle 92 is for guiding the sizing device 86, and the distal attachment portion 94 is for connecting the handle to the sizing member 90. Referring to FIGS. 8B-C, the sizing member 90 includes an annular support member 96 having an anterior end portion 98, a posterior end portion 100, and first and second oppositely disposed intermediate portions 102 and 104 extending between the anterior and posterior end portions. The annular support member 96 has a planar configuration (FIG. 8B) can have a 3D or saddle-shaped configuration.

The sizing member 90 defines a longitudinal axis 106 (FIG. 8B) and includes a bracing portion 108 having an attachment mechanism 110, such as an aperture for mating to the distal attachment portion 94 of the handle member 88. As shown in FIG. 8B, the bracing portion 108 extends above the longitudinal axis 106 of the annular support member 96. The sizing member 90 further includes an infra-annular support member 112 for supporting a heart valve leaflet (e.g., an inferior aspect of a posterior leaflet 26, such as an inferior free edge 36) and subvalvular apparatus (e.g., chordae tendineae 32 and 32' and/or papillary muscle(s) 38 and 38'). As shown in FIG. 8B, the infra-annular support member 112 extends below the longitudinal axis 106 of the annular support member 96. In one example of the present disclosure, the infra-annular support member 112 can be dimensioned to extend below the posterior mitral leaflet 26 and engage at least one subvalvular structure.

To determine the dimensions of the mitral valve 12 using the sizing device 86, access to the mitral valve is gained via an open-chest surgical procedure. During the procedure, the mitral valve 12 is visualized so that the sizing device 86, and in particular the sizing member 90, can be positioned about a superior aspect of the mitral valve 12. Using the handle 92 to guide the sizing member 90 into the left atrium 14, the sizing device 86 is positioned about the mitral valve 12 so that the annular support member 96 contacts the mitral valve annulus 18 and the infra-annular support member 112 contacts or engages at least one subvalvular structure from behind.

Next, blood flow through the mitral valve 12 is monitored to assess coaptation between the anterior and posterior mitral leaflets 24 and 26. Differently dimensioned sizing members 90 can be placed over the mitral valve 12 until substantially normal coaptation of the mitral valve is observed. "Normal blood flow" can refer to the movement of blood through a mammalian valve or vasculature that is unimpeded and progresses under physiologically-normal pressures and at a physiologically-normal rate. When substantially normal blood flow is observed through the mitral valve 12, the dimensions of the sizing member 90 are noted and an apparatus 10$_e$ having dimensions that correspond to the dimensions of the sizing member is selected for implantation. It should be appreciated that a saline solution test may additionally or alternatively be used to assess proper leaflet coaptation and blood flow through the mitral valve 12.

Figure 8D:
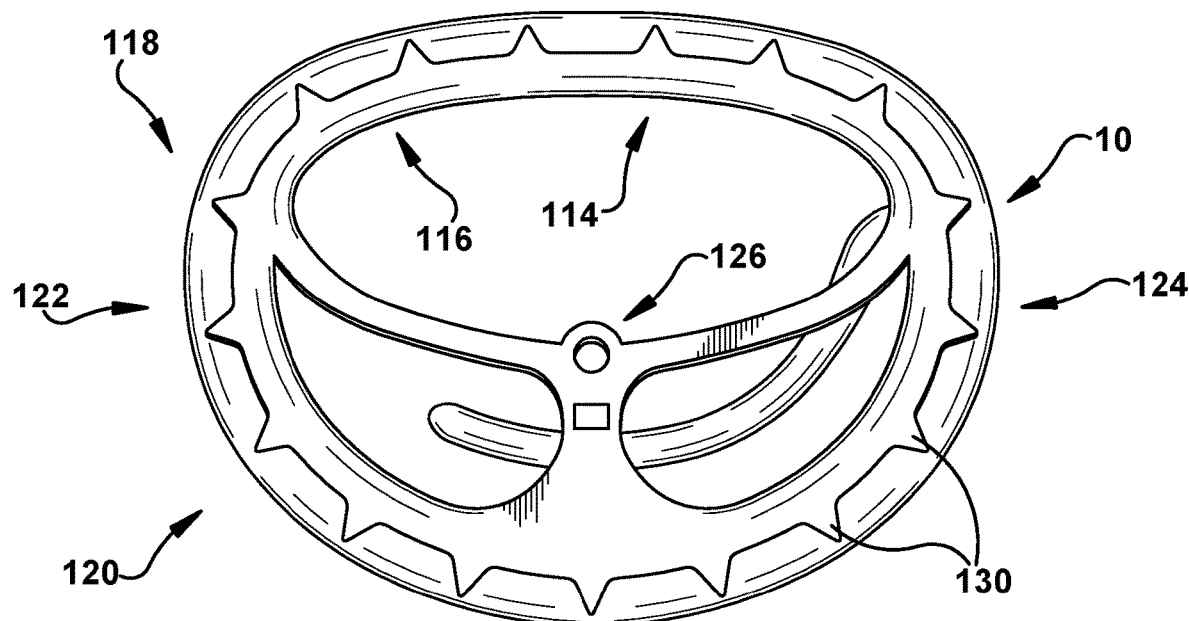
FIG. 8D is a top view showing the apparatus in FIG. 1A coupled to a delivery device or holder.
Figure 8E:
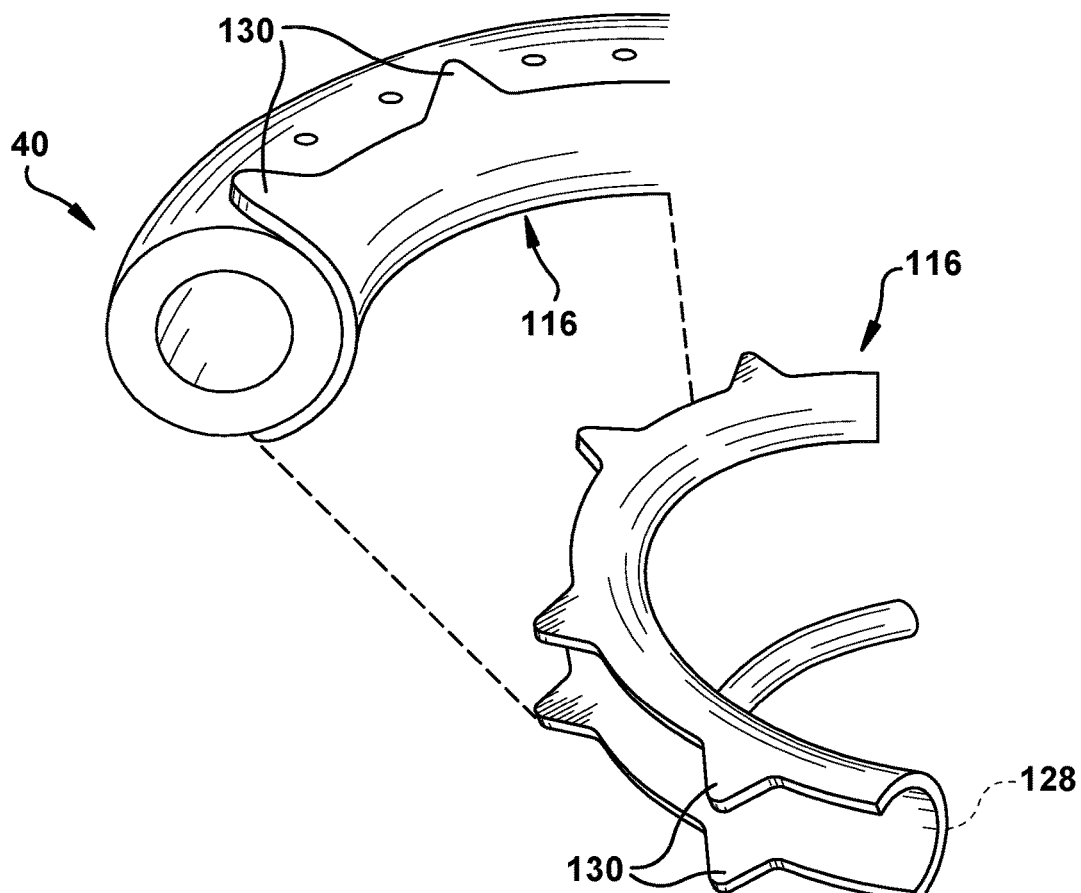
FIG. 8E is a magnified perspective view showing a portion of the delivery device or holder (FIG. 8D) being coupled to the apparatus in FIG. 1A.
Figure 9A:
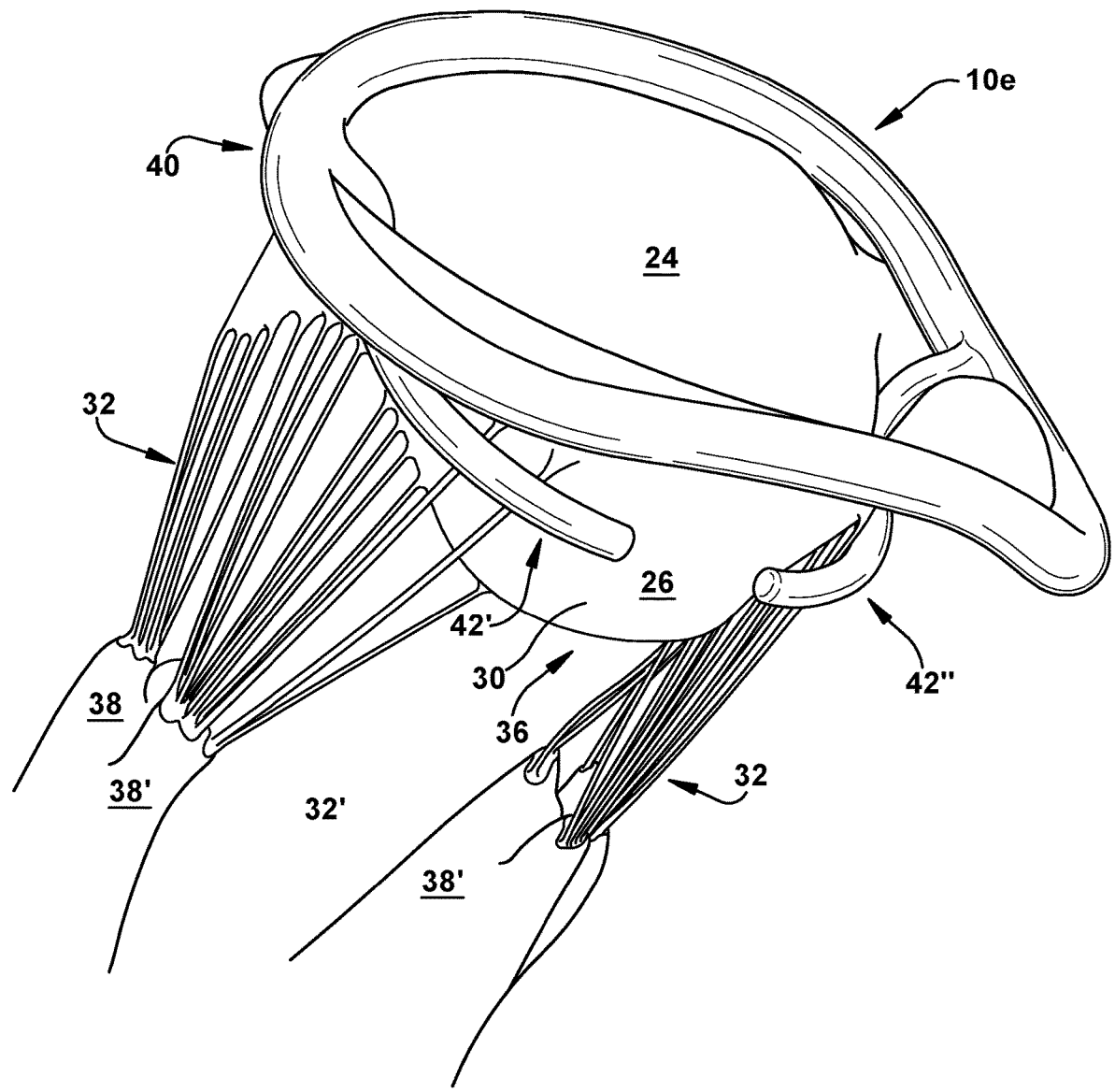
FIG. 9A is a perspective view showing the apparatus in FIG. 7A implanted about a diseased mitral valve.
Figure 9B:
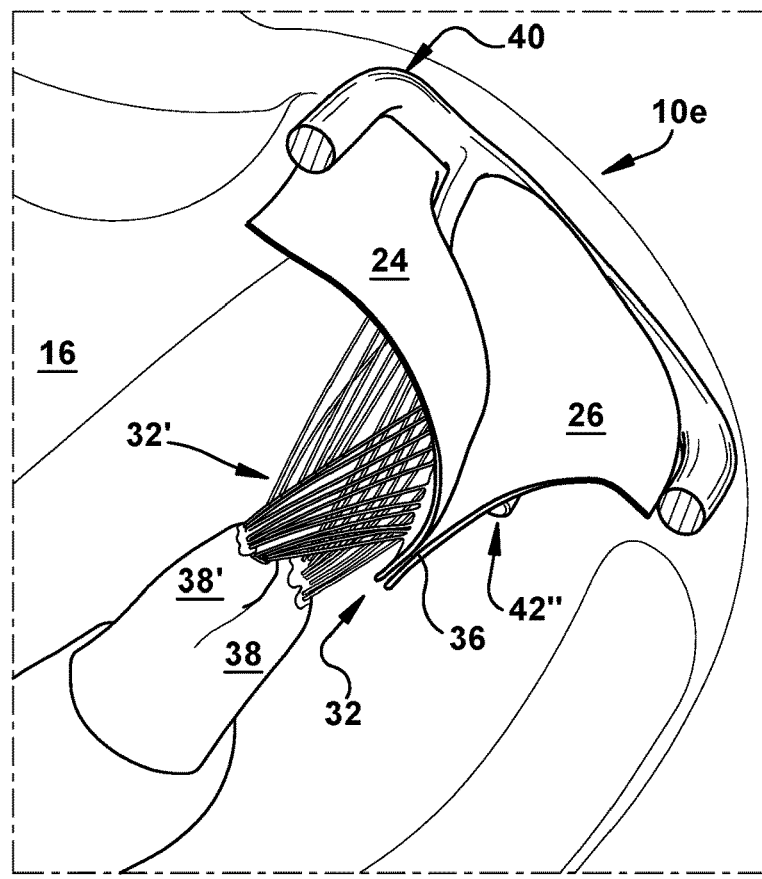
FIG. 9B is a cross-sectional view of the apparatus in FIG. 9A.
Figure 9C:
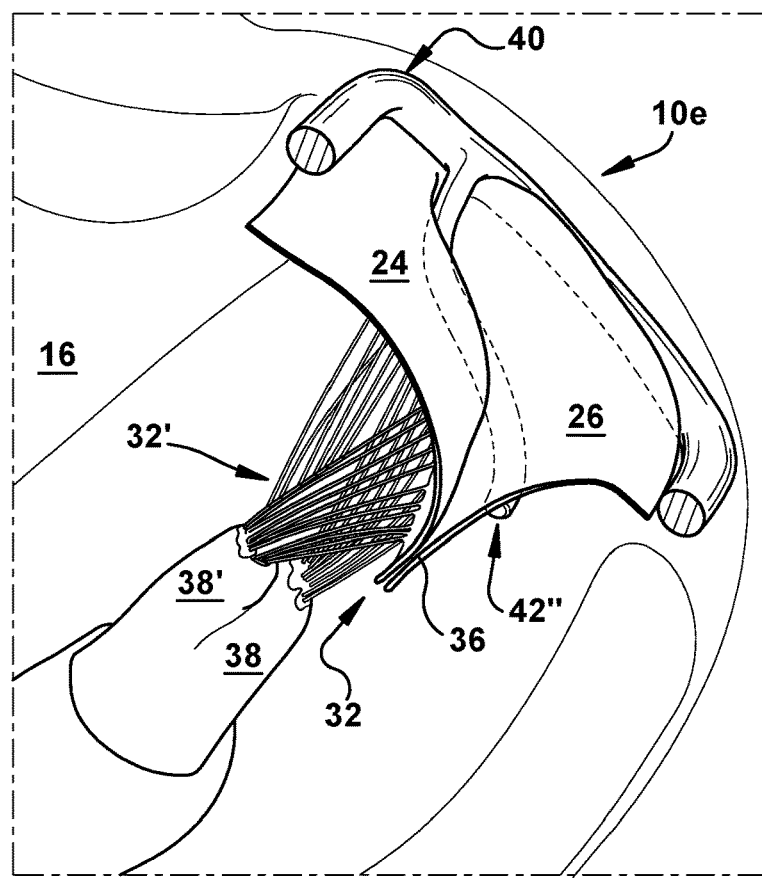
FIG. 9C is a cross-sectional showing an infra-annular posterior support member of the apparatus in FIG. 9B extending about an inferior free edge of the posterior mitral leaflet.

After selecting an appropriately-dimensioned apparatus 10$_e$, the apparatus is attached to a delivery device 114 or holder (FIGS. 8D-E), such as the one disclosed in the '036 application. As shown in FIGS. 8D-E, the delivery device 114 or holder comprises a ring-shaped support member 116 having an anterior end portion 118, a posterior end portion 120, and oppositely disposed first and second intermediate portions 122 and 124 extending between the anterior and posterior end portions. The delivery device 114 or holder includes an attachment mechanism 126, such as an aperture for connecting to the distal attachment portion 94 of the sizing device 86 (or similar to that). The ring-shaped support member 116 has a C-shaped cross-section that defines a channel 128 (FIG. 8E). The channel 128 extends around the periphery of the ring-shaped support member 116 and includes a plurality of extensions 130 to facilitate attachment of the apparatus 10$_e$ to the delivery device 114 or holder. The delivery device 114 or holder also includes a plurality of suture attachment points 132 through which sutures can be threaded to attach the apparatus 10$_e$ to the delivery device or holder. The apparatus 10$_e$ can be released by cutting sutures over different points 132.

To begin the implant procedure of the apparatus 10$_e$, a silicone tube (not shown) is passed through at least one commissure of the mitral valve 12 and placed behind at least one subvalvular structure, such as the chordae tendineae 32 and 32' and/or papillary muscle(s) 38 and 38' associated with the posterior mitral leaflet 26. Once the apparatus 10$_e$ is securely attached to the delivery device 114, sutures (not shown) are placed in the mitral annulus 18. The delivery device 114 is then positioned about the superior aspect of the mitral valve 12. Next, the sutures are passed through the marker(s) 70 (e.g., holes), while the delivery device engages the mitral valve 12 and the substantially annular support member 40 of the apparatus 10$_e$ is advanced toward the mitral annulus 18. Next, the silicone tube is manipulated so that an open end of the tube engages a distal end of at least one of the first and second infra-annular posterior support members 42' and 42". The tube is then gently pulled from its non-engaged end, which causes the first and second infra-annular posterior support members 42' and 42" to move through the commissures and engage at least one subvalvular structure from behind. The tube is then disengaged, followed by removal of the handle portion 88 and tightening of the sutures so that the apparatus 10$_e$ is securely positioned about the mitral valve 12. After tightening of the sutures is complete, the sutures are cut so that the delivery device 114 or holder is detached from the apparatus 10$_e$ and removed from the left atrium 14.

With the apparatus 10$_e$ securely in place (FIGS. 9A-C), two levels of cardiac remodeling can simultaneously occur. At the sub-annular level, the first and second infra-annular posterior support members 42' and 42" support at least one subvalvular structure (e.g., the inferior free edge 36 of the posterior mitral leaflet 26, the chordae tendineae 32 and 32' associated with the posterior leaflet, and/or papillary muscle (s) 38 and 38' associated with posterior leaflet) during systole by moving forward the subvalvular structure(s), which reduces the restrictive motion of the posterior mitral leaflet and prevents or mitigates regurgitation of blood through the mitral valve 12. Furthermore, left ventricle remodeling caused by ischemic and dilated cardiomyopathy is prevented or mitigated by pushing (or moving) forward (or medially) the posterior left ventricular wall (i.e., a reverse remodeling mechanism). Simultaneously, at the annular level, a portion of the posterior left ventricular wall is pushed forward to prevent or mitigate not only ventricular remodeling caused by dilated and ischemic cardiomyopathy, but also the incidence of recurrent mitral regurgitation over time. Also at the annular level, the 3D saddle-shaped geometry of the apparatus 10$_e$ remodels the mitral annulus 18 and reduces the annular diameter to improve leaflet coaptation. Upon proper implantation of the apparatus 10$_e$, the procedure can be completed so that normal blood flow can resume through the mitral valve 12.

Figure 10A:
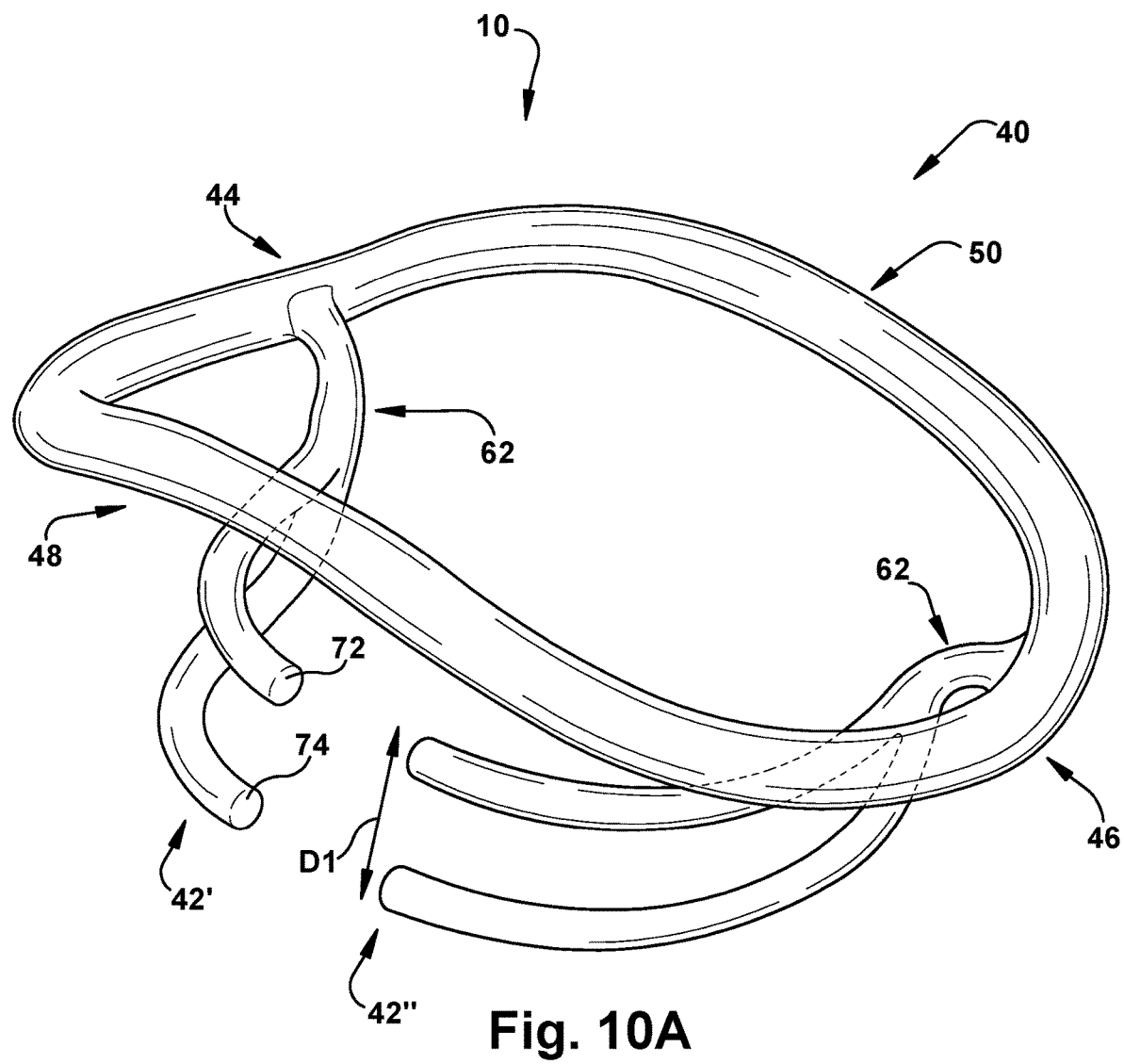
FIG. 10A is a perspective view showing an alternative configuration of the apparatus in FIGS. 7A-B.
Figure 10B:
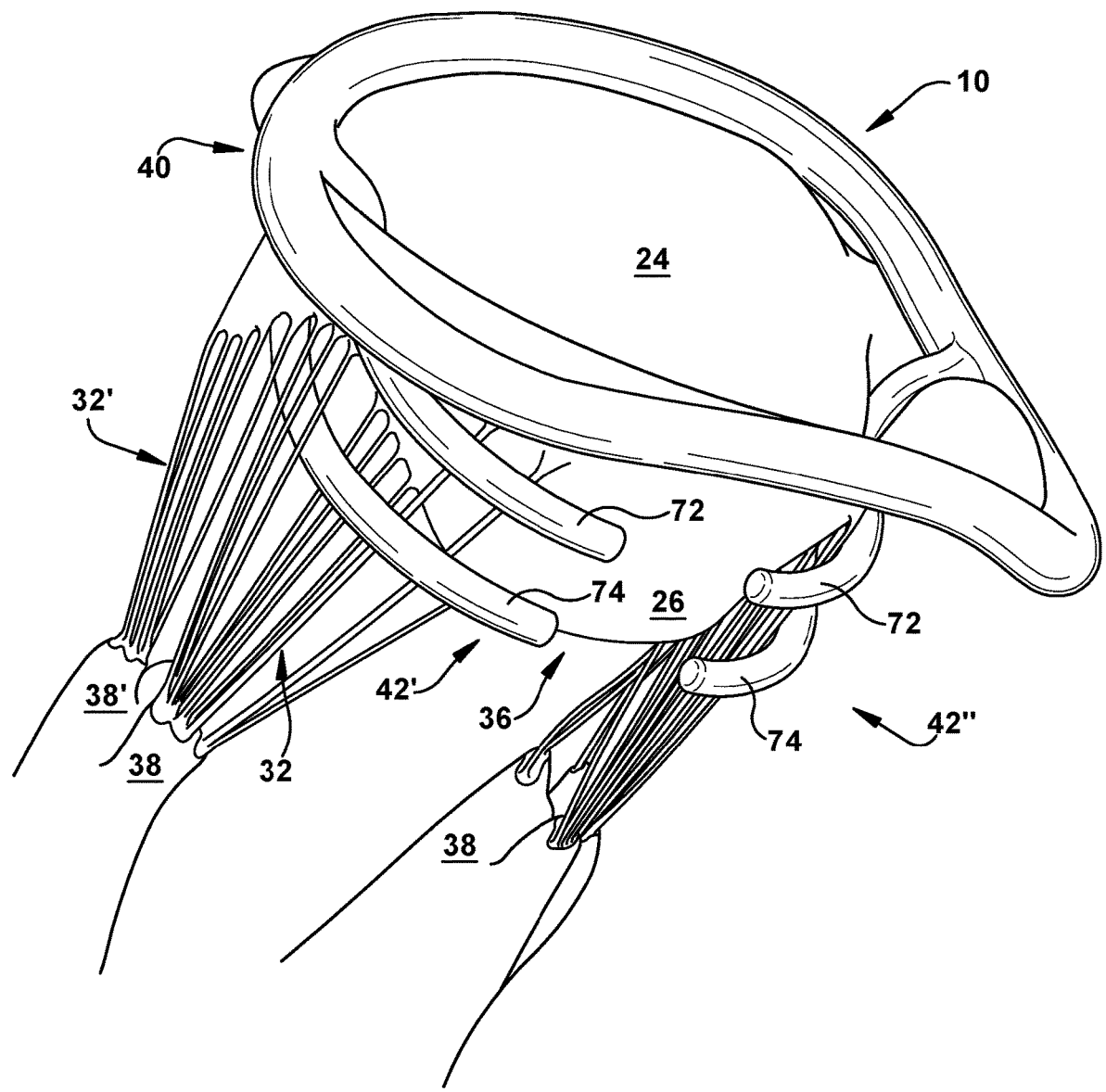
FIG. 10B is a perspective view showing the apparatus in FIG. 10A implanted about a diseased mitral valve.

FIGS. 10A-12C illustrate other geometric variations of the apparatus 10 shown in FIGS. 1A-D. As shown in FIG. 10A, for example, the engaging portion 60 of each of the first and second infra-annular posterior support members 42' and 42" can alternatively have a fork-like configuration. In particular, each of the engaging portions 60 can include oppositely disposed first and second engaging portions 72 and 74 that are spaced apart, and axially offset from each other (relative to a central axis CA), by a distance D1. The distance D1 can be the same or different between the first and second infra-annular posterior support members 42' and 42", depending upon the anatomy of the subject's mitral valve 12, the particular valvular insufficiency from which the subject is suffering, as well as other factors. Each of the first and second engaging portions 72 and 74 can have a concave shape relative to the anterior end portion 50 of the substantially annular support member 40. Additionally, each of the first and second engaging portions 72 and 74 can extend across or behind all or only a portion of at least one subvalvular structure (FIG. 10B).

Figure 11A:
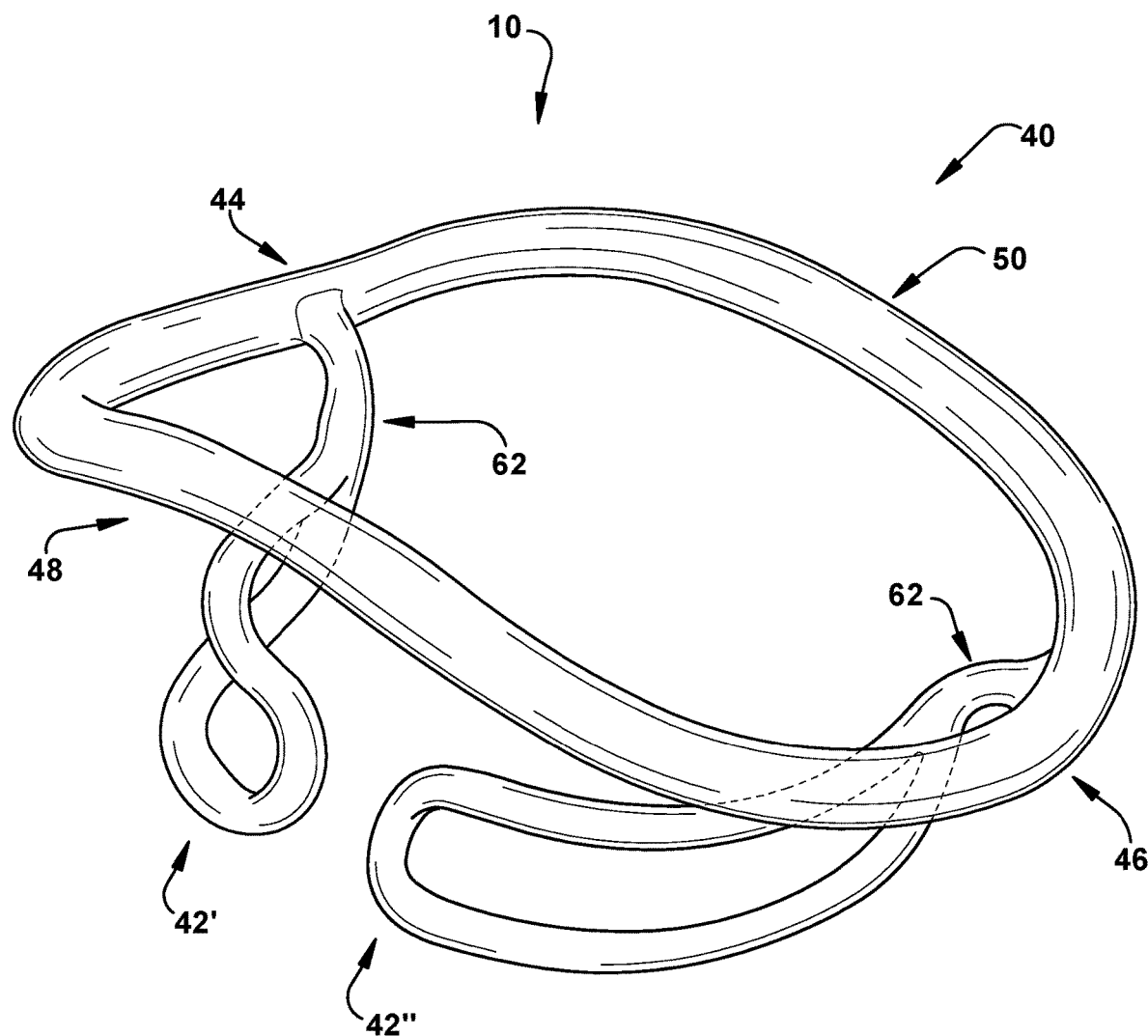
FIG. 11A is a perspective view showing an alternative configuration of the apparatus in FIGS. 7A-B.
Figure 11B:
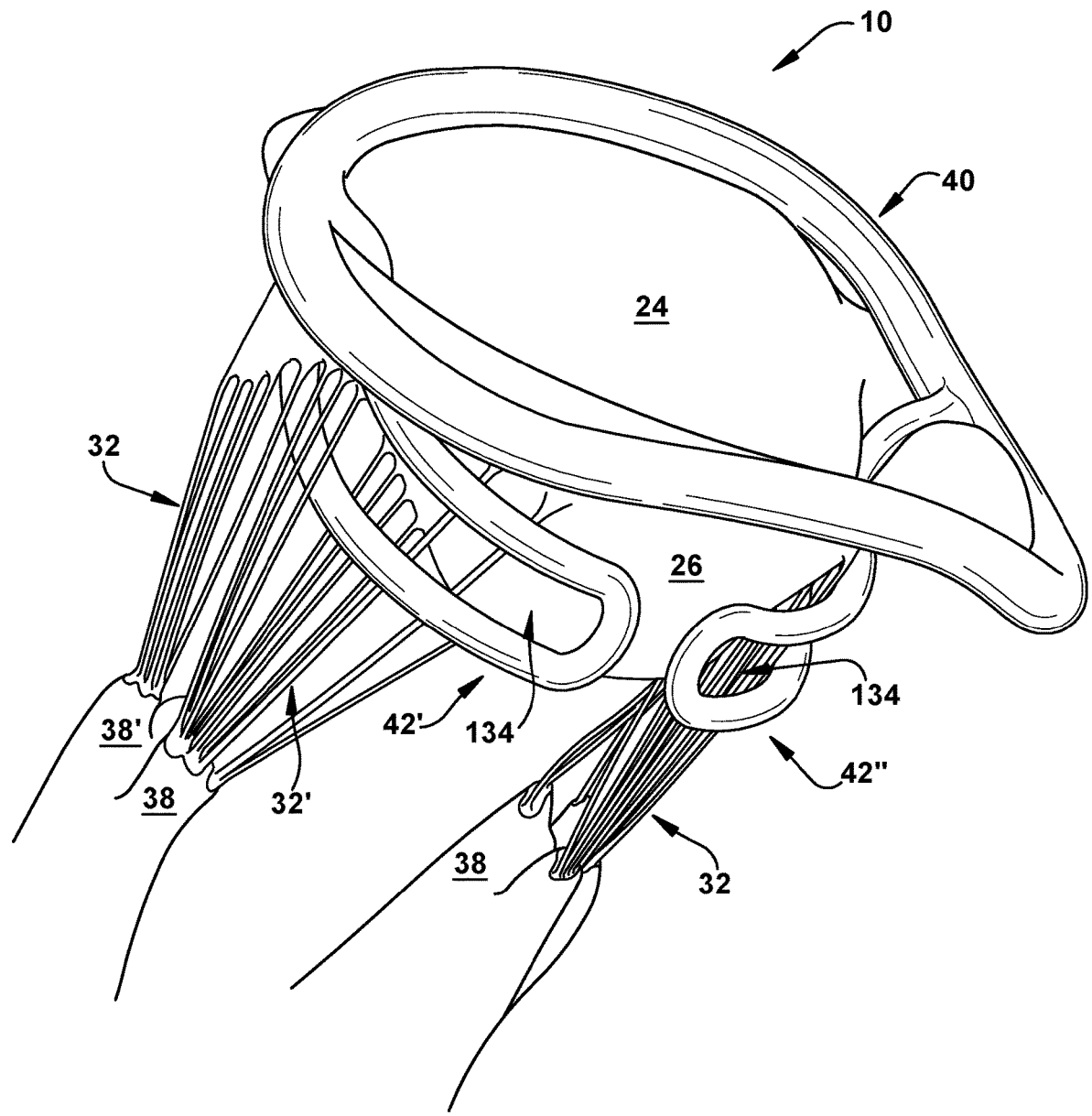
FIG. 11B is a perspective view showing the apparatus in FIG. 11A implanted about a diseased mitral valve.

As shown in FIGS. 11A-B, each of the first and second infra-annular posterior support members 42' and 42" can alternatively have an arcuate, loop-shaped configuration that includes an aperture 134 extending therethrough. The engaging portion 60 of each of the first and second infra-annular posterior support members 42' and 42" can have a concave shape relative to the anterior end portion 50 of the substantially annular support member 40. Additionally, the engaging portion 60 of each of the first and second infra-annular posterior support members 42' and 42" can extend across or behind all or only a portion of at least one subvalvular structure (FIG. 11B).

Figure 12A:
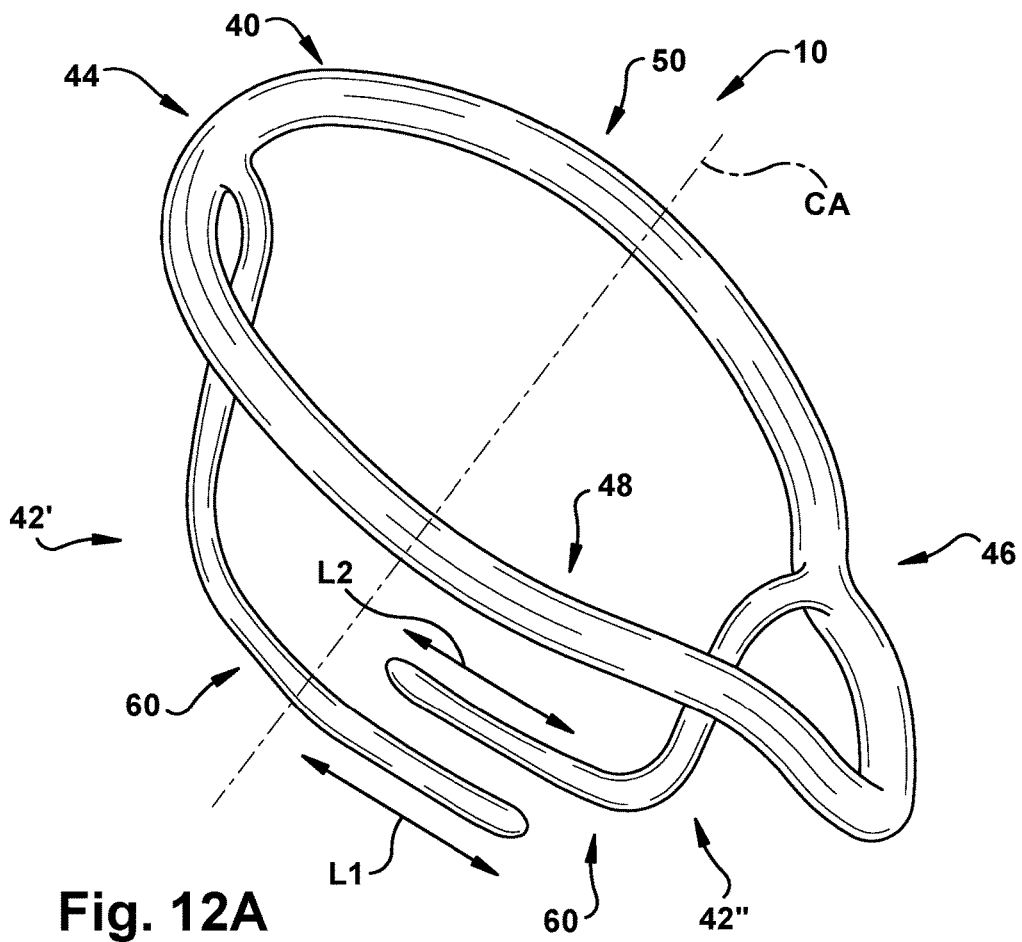
FIG. 12A is a perspective view showing an alternative configuration of the apparatus in FIGS. 7A-B.
Figure 12B:
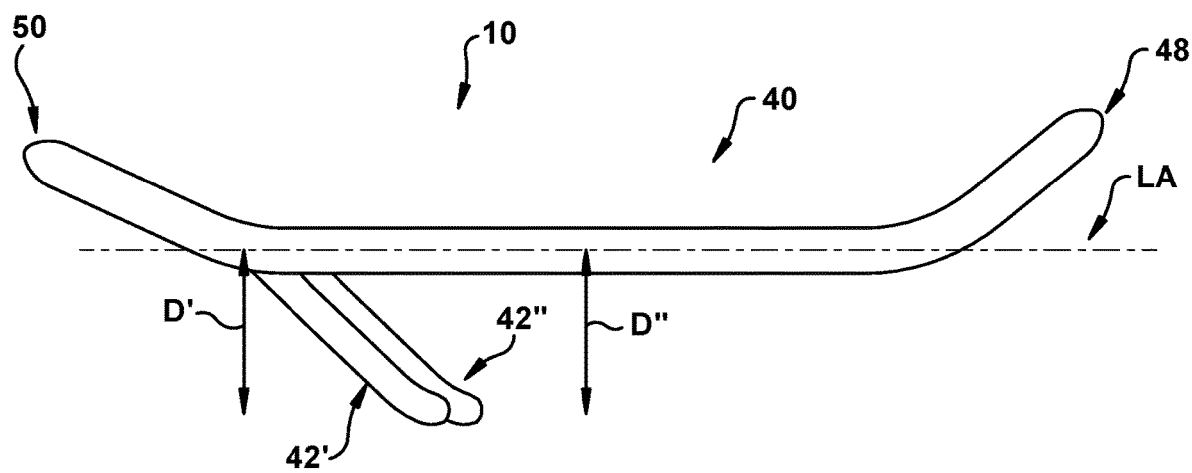
FIG. 12B is a side view of the apparatus in FIG. 12A.
Figure 12C:
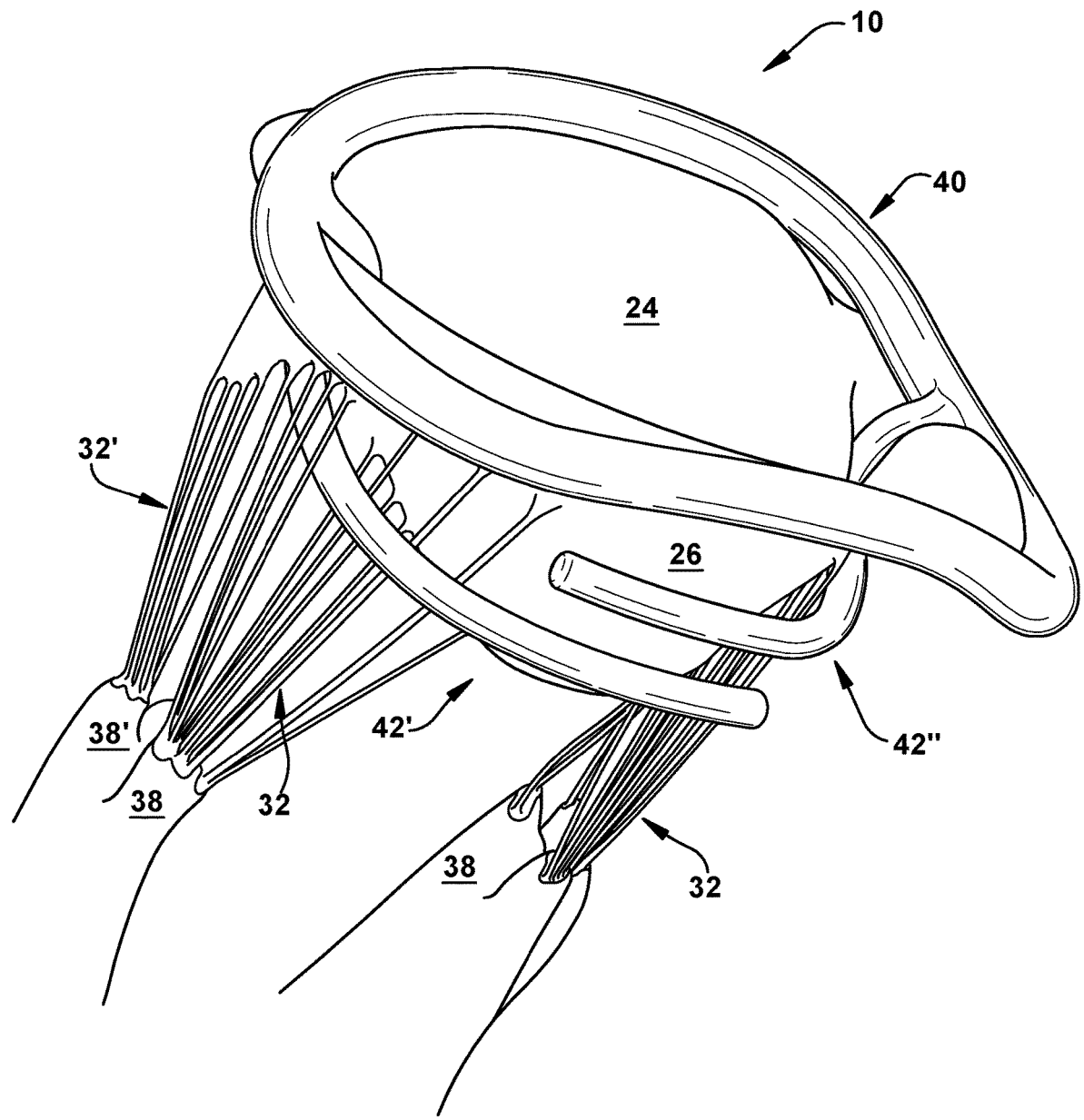
FIG. 12C is a perspective view showing the apparatus in FIGS. 12A-B implanted about a diseased mitral valve.

As shown in FIGS. 12A-C, each of the first and second infra-annular posterior support members 42' and 42" can be configured in a similar fashion as the first and second infra-annular posterior support members illustrated in FIGS. 7A-B. As shown in FIG. 12B, however, the first infra-annular posterior support member 42' is dimensioned to extend a first distance D', which is less than a second distance D" that corresponds to the second infra-annular posterior support member 42". In other words, the first distance D' is less than the second distance D" so that the first and second infra-annular posterior support members 42' and 42" are axially offset from one other relative to a central axis CA (FIG. 12A).

As can additionally be seen in FIG. 12A, a length L1 of the first infra-annular posterior support member 42' is dimensioned to overlap with a corresponding length L2 of the second infra-annular posterior support member 42". The engaging portion 60 of each of the first and second infra-annular posterior support members 42' and 42" can have a concave shape relative to the anterior end portion 50 of the substantially annular support member 40. Additionally, the engaging portion 60 of each of the first and second infra-annular posterior support members 42' and 42" can extend across or behind all or only a portion of at least one subvalvular structure (FIG. 12C).

Figure 13A:
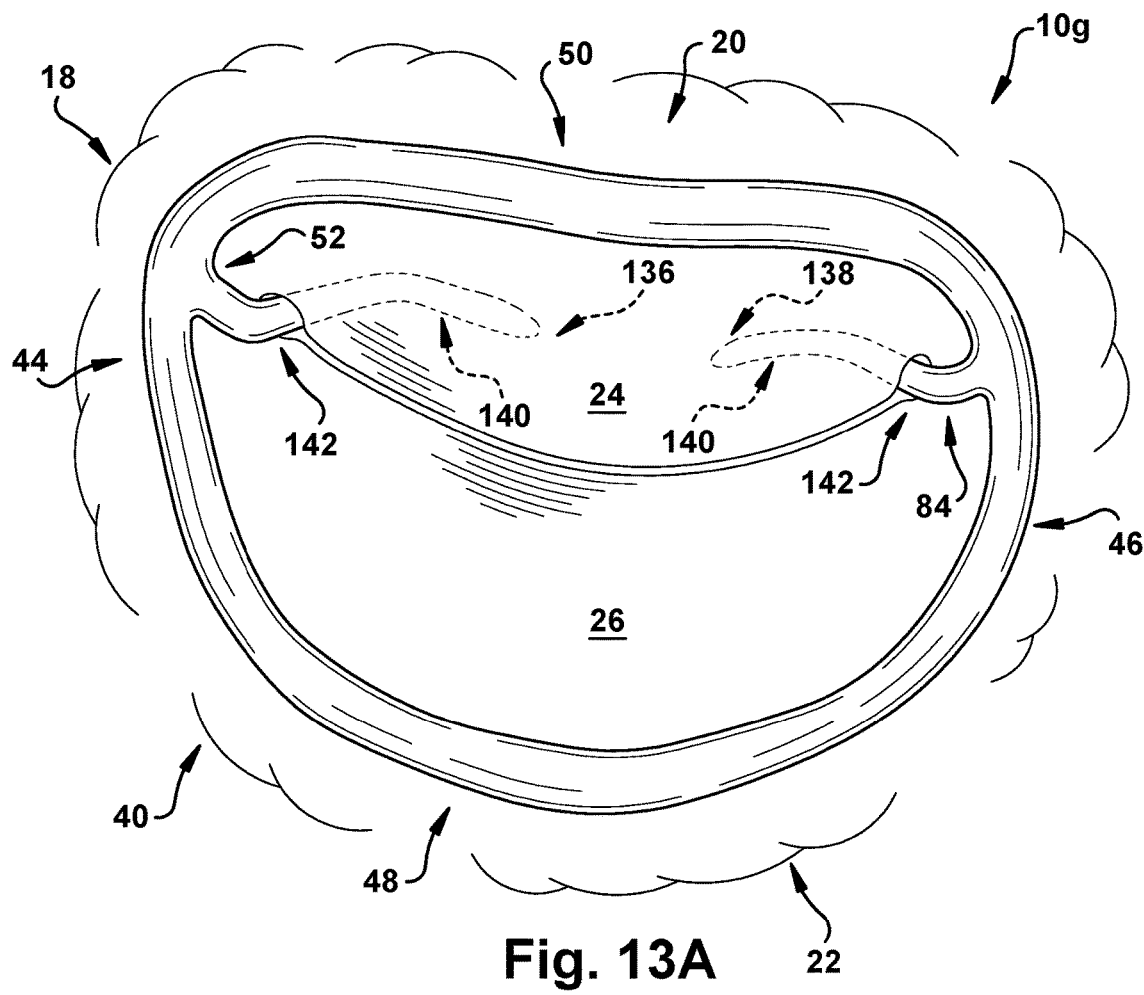
FIG. 13A is a plan view showing an alternative configuration of the apparatus in FIGS. 7A-B.
Figure 13B:
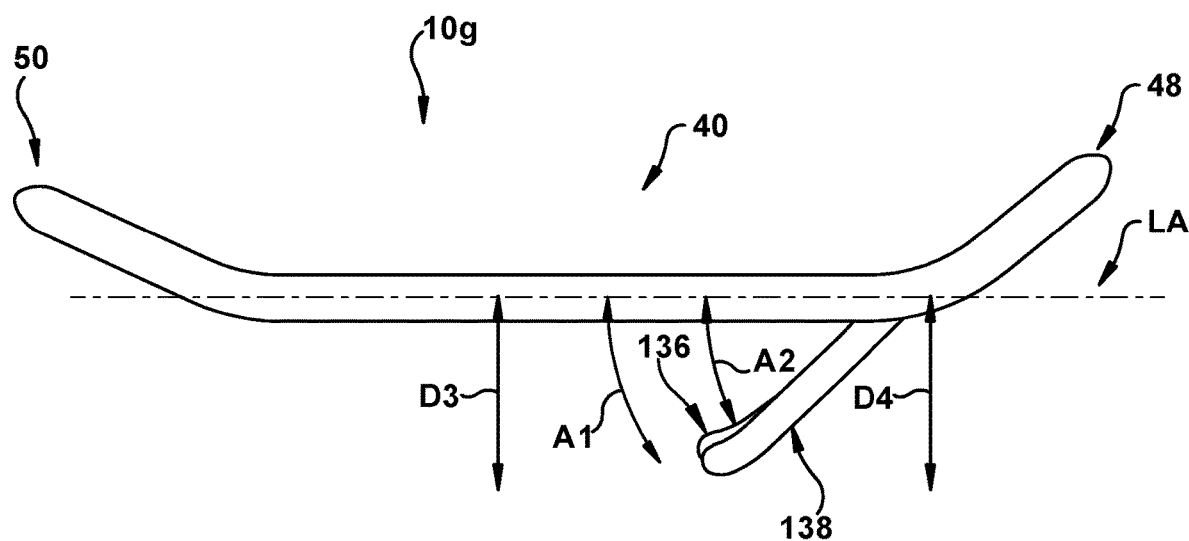
FIG. 13B is a side view of the apparatus in FIG. 13A.

Another aspect of the present disclosure is illustrated in FIGS. 13A-B. The apparatus $10_f$ shown in FIGS. 13A-B is identically constructed as the apparatus 10, shown in FIGS. 7A-B, except as described below. In FIGS. 13A-B, structures that are identical as structures in FIGS. 7A-B use the same reference numbers, whereas structures that are similar but not identical carry the suffix "f". It should be appreciated that the apparatus $10_f$ can be constructed from any of the materials described above, and that the apparatus can include a layer 68 of biocompatible material and/or a therapeutic agent(s), as also described above.

As shown in FIGS. 13A-B, the apparatus $10_f$ comprises a substantially annular support member 40, a first infra-annular anterior support member 136, and a second infra-annular anterior support member 138. The substantially annular support member 40 can be entirely annular and comprise a first intermediate portion 44, a second intermediate portion 46, a posterior end portion 48 extending between the first and second intermediate portions, and an anterior end portion 50 extending between the first and second intermediate portions and oppositely disposed from the posterior end portion. Alternatively, the substantially annular support member 40 can be partly annular and comprise a first intermediate portion 44, a second intermediate portion 46, and a posterior end portion 48 extending between the first and second intermediate portions.

The anterior end portion 50 (FIGS. 13A-B) and the posterior end portion 48 are dimensioned for attachment to the anterior and posterior portions 20 and 22 of the mitral annulus 18, respectively. For example, the posterior end portion 48, the first intermediate portion 44, and the second intermediate portion 46 form a continuous arc so that the posterior end portion has a concave shape relative to the anterior end portion 50. Similarly, the anterior end portion 50, the first intermediate portion 44, and the second intermediate portion 46 form a continuous arc so that the anterior end portion has a convex shape relative to the posterior end portion 48. As shown in FIG. 13B, the substantially annular support member 40 also includes a longitudinal axis LA. The substantially annular support member 40 can have a rigid or semi-rigid configuration.

The first and second infra-annular anterior support members 136 and 138 are dimensioned, shaped, and configured to extend below the anterior mitral leaflet 24 and across or behind at least one subvalvular structure when the apparatus $10_f$ is implanted on or about the mitral annulus 18. The first infra-annular anterior support member 136 is securely and directly connected to the substantially annular support member 40 at a first location 52, and the second infra-annular anterior support member 138 is securely and directly connected to the substantially annular support member at a second location 84 that is different than the first location. As shown in FIG. 13A, for example, the first infra-annular anterior support member 136 is securely and directly connected to the first intermediate portion 44, and the second infra-annular anterior support member 138 is securely and directly connected to the second intermediate portion 46.

As shown in FIG. 13B, each of the first and second infra-annular anterior support members 136 and 138 extends at an angle A1 and A2 and at a distance D3 and D4, respectively, below the longitudinal axis LA of the substantially annular support member 40. The angle A1 and A2 of each of the first and second infra-annular anterior support members 136 and 138, respectively, is such that the first and second infra-annular anterior support members facilitate optimal leaflet coaptation. In one example of the present disclosure, the angle A1 and A2 of one or both of the first and second infra-annular anterior support members 136 and 138, respectively, can be about 20° to about 40° (e.g., about 30°). It will be appreciated that the angle A1 and A2 can be the same or different. Similarly, the distance D3 and D4 is such that a portion of each of the first and second infra-annular anterior support members 136 and 138, respectively, extends below the anterior mitral leaflet 24 to enable the first and second infra-annular first and second anterior support members to facilitate optimal leaflet coaptation. It will also be appreciated that the distance D3 and D4 can be the same or different.

Each of the first and second infra-annular anterior support members 136 and 138 is configured similarly as the infra-annular posterior support member 42 shown in FIGS. 1A-B and described above. For example, each of the first and second infra-annular anterior support members 136 and 138 (FIG. 13A) comprises an engaging portion 140 and an integral neck portion 142 that extends from the engaging portion to the first location 52. The engaging portion 140 of each of the first and second infra-annular anterior support members 136 and 138 can have an arcuate shape (e.g., convex) relative to the anterior end portion 50 of the substantially annular support member 40.

It will be appreciated that the apparatus $10_f$ can additionally or optionally include other features as the apparatus $10_e$ shown in FIGS. 7A-B and described above. For example, the apparatus $10_f$ can include: an adjustable mechanism 54; a layer 68 of biocompatible material; at least one marker 70 to facilitate attachment of the apparatus to the mitral annulus 18; and/or one or a combination of therapeutic agents.

Figure 14A:
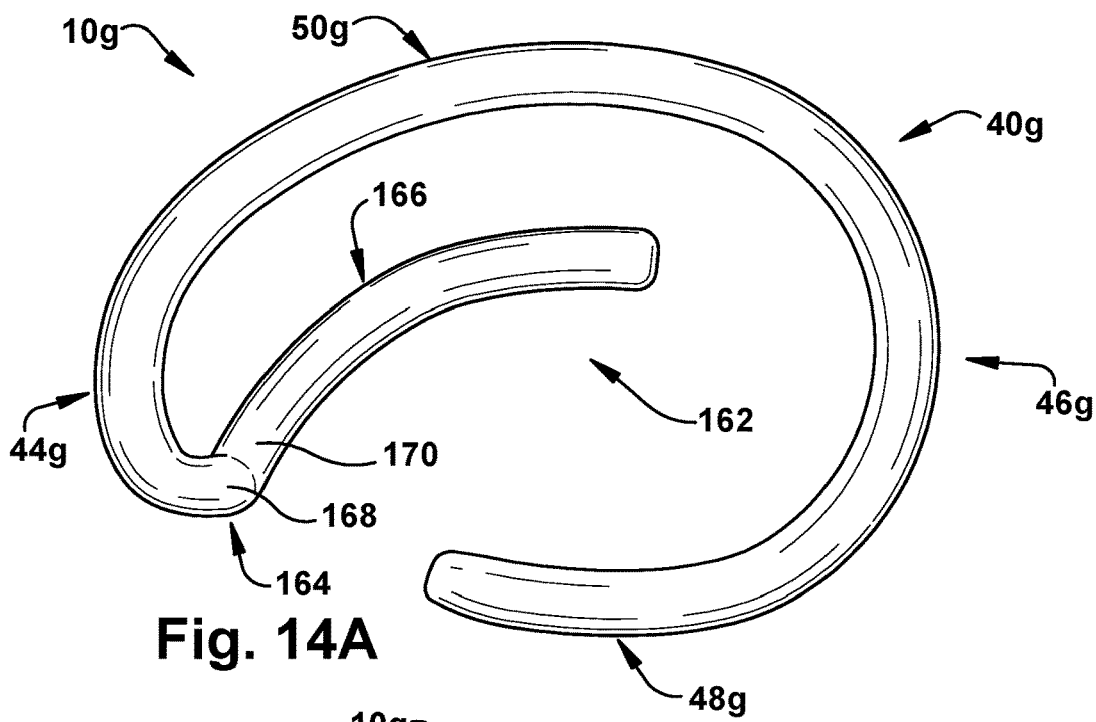
FIG. 14A is a top view of an apparatus for treating regurgitation of blood flow through a tricuspid valve constructed in accordance with another aspect of the present disclosure.
Figure 14B:
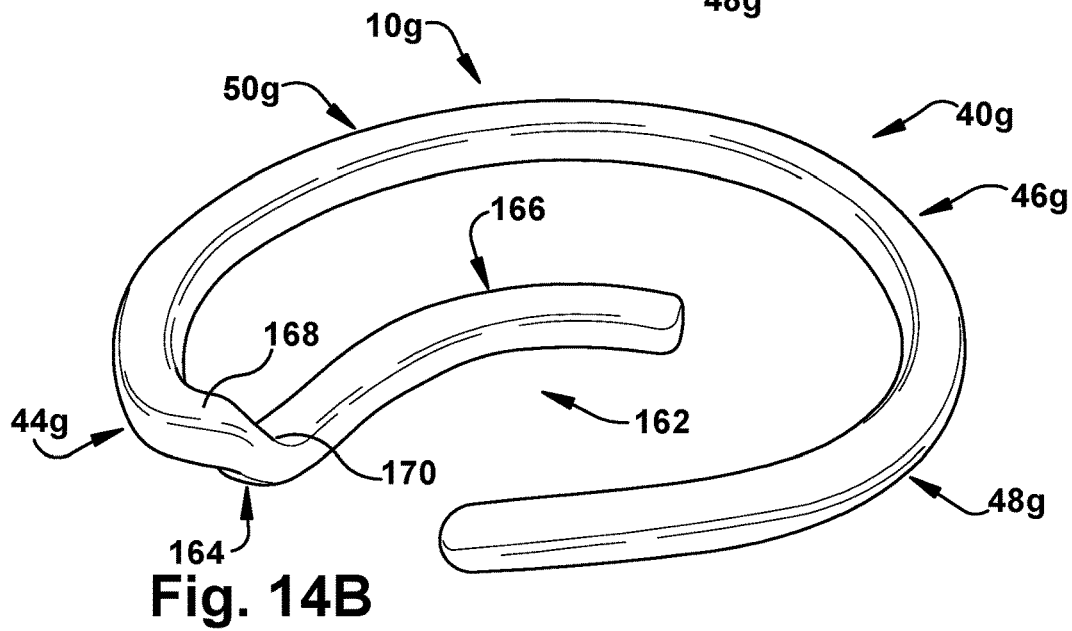
FIG. 14B is a perspective view of the apparatus in FIG. 14A.
Figure 14C:
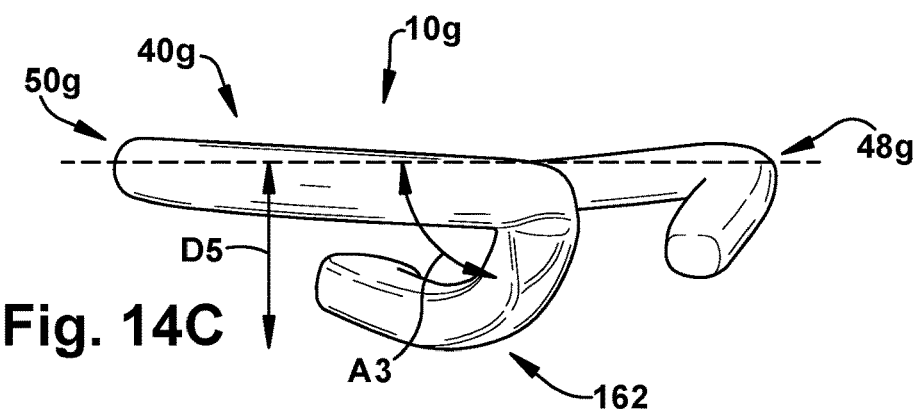
FIG. 14C is a side view of the apparatus in FIG. 14A.

Another aspect of the present disclosure is illustrated in FIGS. 14A-C. The apparatus $10_g$ shown in FIGS. 14A-C is identically constructed as the apparatus 10 and $10_f$ shown in FIGS. 1A-E and FIGS. 13A-B, respectively, except as described below. In FIGS. 14A-C, structures that are identical as structures in FIGS. 1A-E and FIGS. 13A-B use the same reference numbers, whereas structures that are similar but not identical carry the suffix "g". It should be appreciated that the apparatus $10_g$ can be constructed from any of the materials described above, and that the apparatus can include a layer 68 of biocompatible material and/or a therapeutic agent(s), as also described above.

Figure 15:
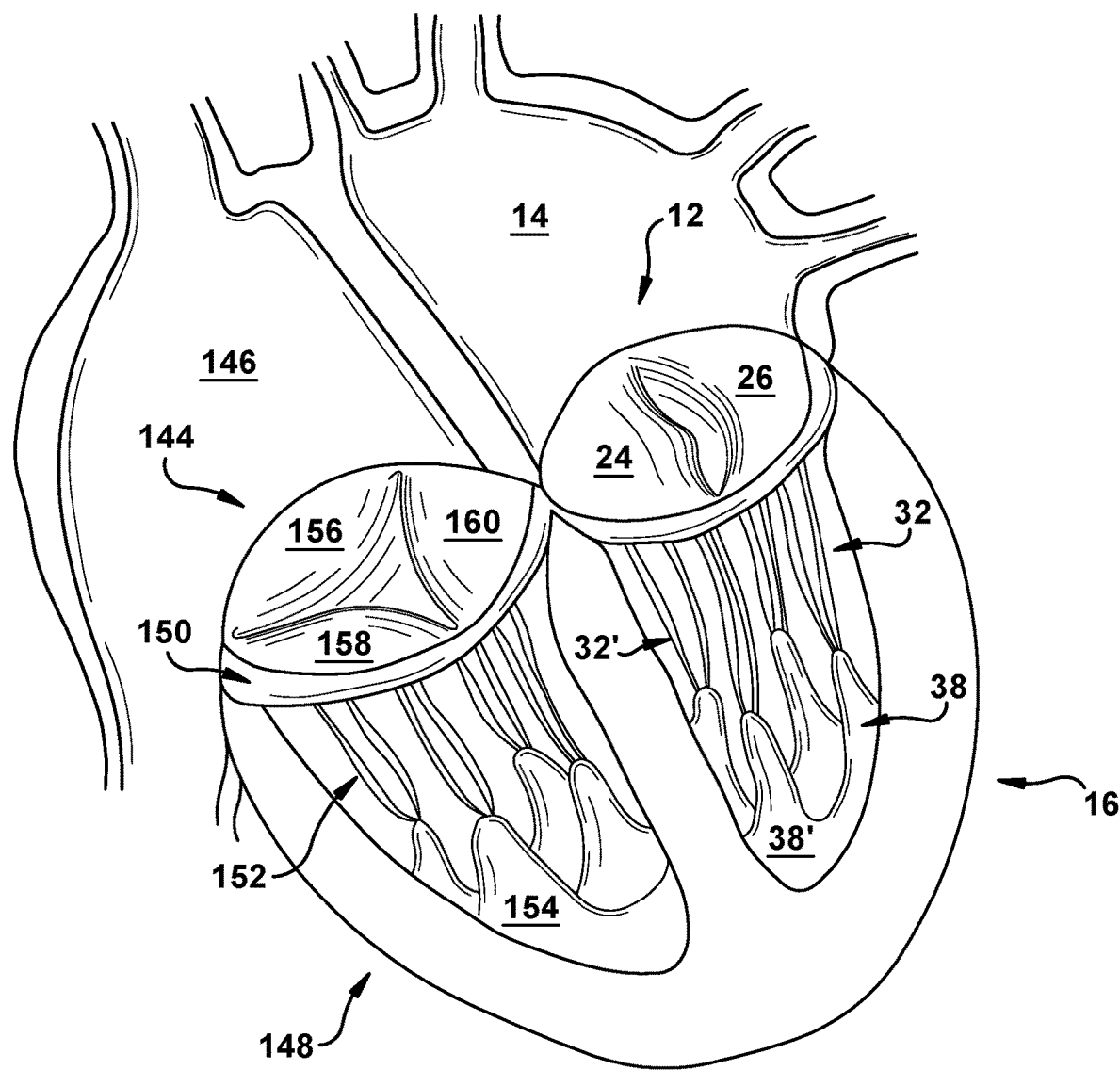
FIG. 15 is a cross-sectional view of a human heart.

As shown in FIG. 15, the tricuspid valve 144 is located between the right atrium 146 and the right ventricle 148. The tricuspid valve 144 is made up of the three valve leaflets (discussed below), the annulus 150, the supporting chordae tendineae (generally indicated at 152), and the papillary muscles (generally indicated at 154). The tricuspid valve 144 itself is slightly inclined to the vertical so that the margins of the valve are anterosuperior, inferior, and septal, and the leaflets take their name from these attachment sites. The anterosuperior leaflet 156 is the largest leaflet and is interposed between the atrioventricular orifice (not shown) and the conus arteriosus (not shown). The posterior leaflet 158 is the next largest leaflet and is named for its relative posterior position and relationship to the margin of the right ventricle 148. The third and smallest leaflet, the septal leaflet 160, is attached to the right and left fibrous trigones (not shown) and the atrial and ventricular septa. The tricuspid subvalvular apparatus consists of anterior, posterior, and septal papillary muscles 154 and their true chordae tendineae 152. False chordae (not shown) can connect two papillary muscles 154, connect a papillary muscle to the ventricular wall, or connect points on the ventricular walls. The true chordae 152 typically originate from the apical third of the papillary muscle 154 but can originate from the ventricular walls, as is the case for the septal leaflet 160.

Referring again to FIGS. 14A-C, the apparatus $10_g$ can comprise a substantially annular support member $40_g$ and at least one infra-annular anterior support member 162 securely connected thereto. The substantially annular support member $40_g$ can have a 3D shape that corresponds to the 3D shape of the tricuspid annulus 150 (FIG. 15). The substantially annular support member $40_g$ can define a longitudinal axis LA (FIG. 14C) and include an anterior end portion $50_g$, a posterior end portion $48_g$, and oppositely disposed first and second intermediate portions $44_g$ and $46_g$ extending between the anterior and posterior end portions. The anterior end portion $50_g$ and the posterior end portion $48_g$ are dimensioned for attachment to anterior and posterior portions of the tricuspid annulus 150 (FIG. 15), respectively. Although the substantially annular support member $40_g$ (FIGS. 14A-C) is shown as having a C-shaped or partial ring configuration, it will be appreciated that the substantially annular support member can have other configurations, such a completely annular ring configuration.

Figure 14D:
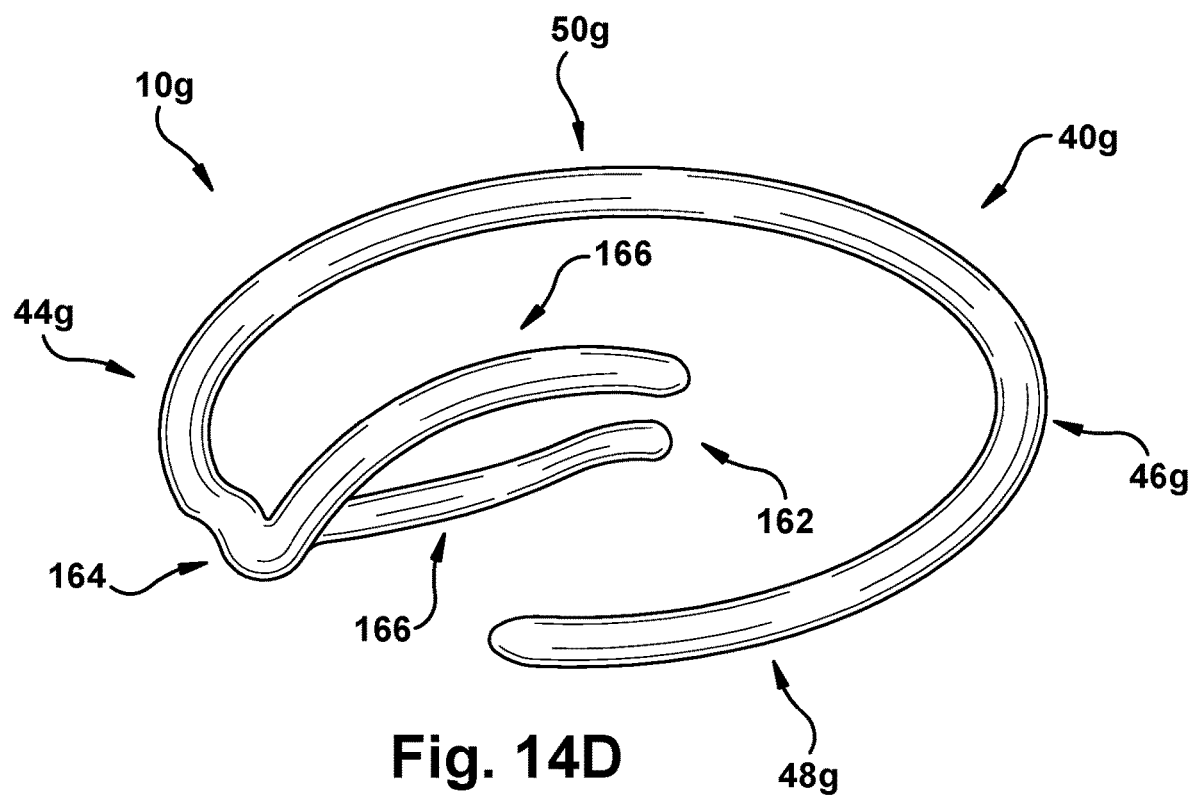
FIG. 14D is a perspective view showing an alternative configuration of the apparatus in FIG. 14A.
Figure 14E:
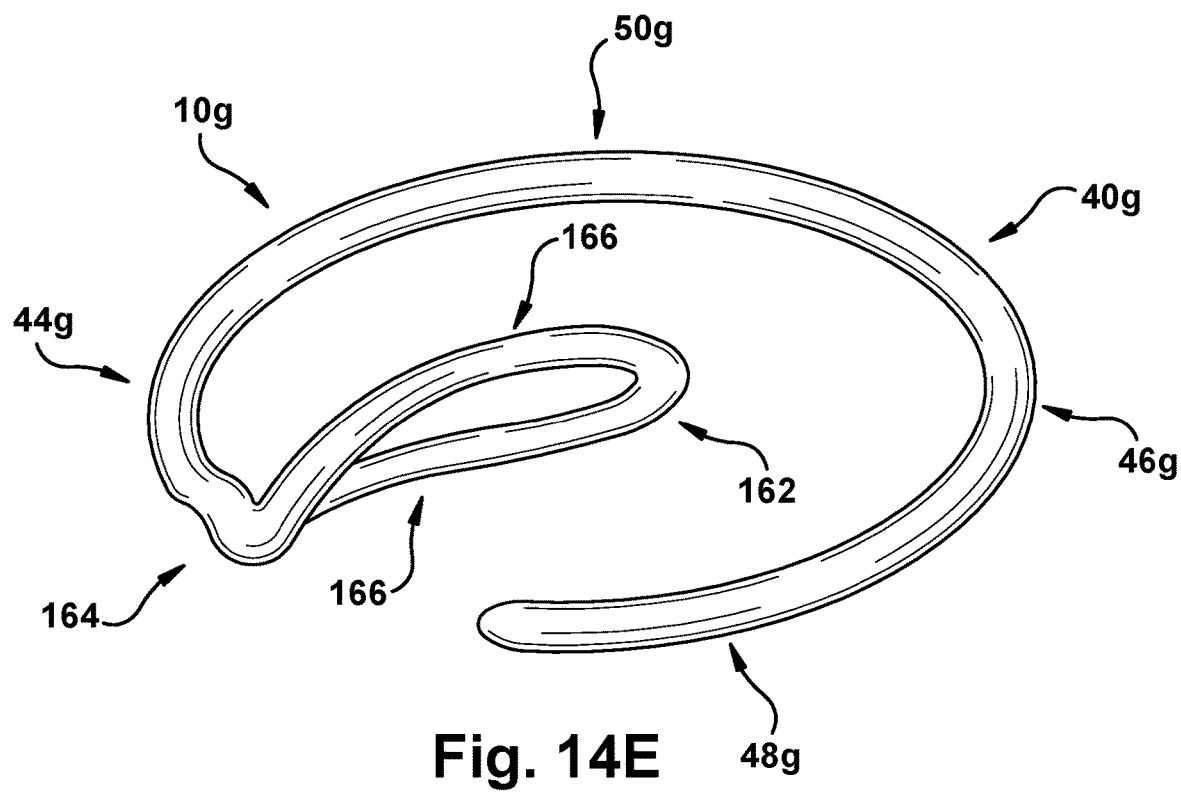
FIG. 14E is a perspective view showing another alternative configuration of the apparatus in FIG. 14A.

As shown in FIGS. 14A-C, the apparatus $10_g$ includes an infra-annular anterior support member 162. It will be appreciated, however, that the apparatus $10_g$ can include more than one infra-annular anterior support member 162 (FIGS. 14D-E) and/or one or more infra-annular support members for supporting the septal leaflet 160 (FIGS. 17A-E) and/or posterior tricuspid leaflet 158. The infra-annular anterior support member 162 is dimensioned to extend below the anterosuperior leaflet 156 and across or behind all or only a portion of at least one subvalvular structure. The infra-annular anterior support member 162 illustrated in FIGS. 14A-C can be dimensioned to extend across or behind the entire inferior free edge (not shown) of the anterosuperior tricuspid leaflet 156, only a portion of the inferior free edge of the anterosuperior tricuspid leaflet, all or only a portion of the chordae tendineae 152 associated with the anterosuperior tricuspid leaflet, and/or all or only a portion of a papillary muscle 154 associated with the anterosuperior tricuspid leaflet.

It will be appreciated that the infra-annular anterior support member 162 can be shaped, configured, and dimensioned to extend across or behind other subvalvular structures, such as: the entire inferior free edge (not shown) of the septal tricuspid leaflet 160; only a portion of the inferior free edge of the septal tricuspid leaflet; all or only a portion of the chordae tendineae 152 associated with the septal tricuspid leaflet; all or only a portion of a papillary muscle 154 associated with the septal tricuspid leaflet; the entire inferior free edge (not shown) of the posterior tricuspid leaflet 158; only a portion of the inferior free edge of the posterior tricuspid leaflet; all or only a portion of the chordae tendineae associated with the posterior tricuspid leaflet; and/or all or only a portion of a papillary muscle associated with the posterior tricuspid leaflet.

The infra-annular anterior support member 162 can have a rigid or semi-rigid configuration. Where the infra-annular anterior support member 162 has a semi-rigid configuration, for example, the first infra-annular anterior support member can be bendable or adjustable to various positions. The infra-annular anterior support member 162 can additionally or optionally include an adjustment mechanism 54 (as described above) for selectively adjusting the position thereof relative to the longitudinal axis LA of the substantially annular support member $40_g$.

As shown in FIG. 14C, the infra-annular anterior support member 162 extends at an angle A3 and at a distance D5 below the longitudinal axis LA of the substantially annular support member $40_f$. The angle A3 of the infra-annular anterior support member 162 is such that the first infra-annular anterior support member facilitates optimal leaflet coaptation. In one example of the present disclosure, the angle A3 of the infra-annular anterior support member 162 can be about 20° to about 40° (e.g., about 30°). Similarly, the distance D5 is such that a portion of the infra-annular anterior support member 162 extends below the anterosuperior tricuspid leaflet 156 to facilitate optimal leaflet coaptation.

The infra-annular anterior support member 162 has an elongated, substantially U-shaped configuration and includes a neck portion 164 (FIG. 14A) that is integrally formed with an engaging portion 166. The neck portion 164 is dimensioned to extend between, or nearly between, a respective one of the commissures of the tricuspid valve leaflets 156, 158 and 160. As shown in FIGS. 14A-B, the neck portion 164 includes oppositely disposed first and second ends 168 and 170 that are integrally formed with the substantially annular support member $40_g$ and the engaging portion 166, respectively. For example, the first end 168 of the neck portion 164 can be integrally formed with the first intermediate portion $44_g$ of the substantially annular support member $40_f$.

The engaging portion 166 of the infra-annular anterior support member 162 has a concave shape relative to the posterior end portion $48_g$ of the substantially annular support member $40_g$. All or only a portion of the engaging portion 166 is dimensioned to contact all or only a portion of a subvalvular structure upon implantation. It will be appreciated that the infra-annular anterior support member 162 can have any one or combination of the configurations shown in FIGS. 4A-B, 5-6, 14D-E and 17D-E; provided, of course, that the engaging portion 166 has a concave shape relative to either the anterior end portion $50_g$ or the posterior end portion $48_g$ of the substantially annular support member $40_g$.

Figure 16A:
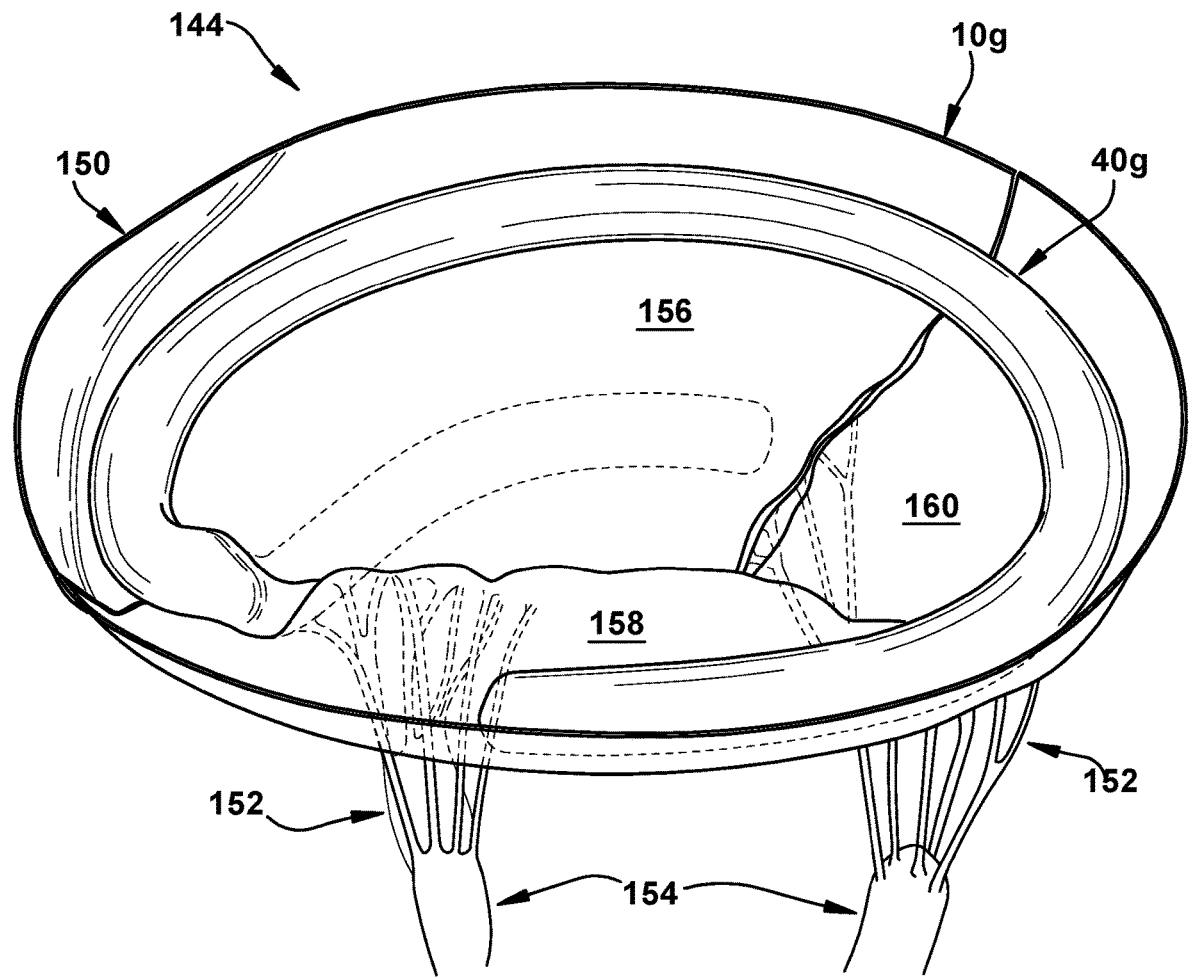
FIG. 16A is a perspective view showing the apparatus in FIG. 14A implanted about a diseased tricuspid valve.
Figure 16B:
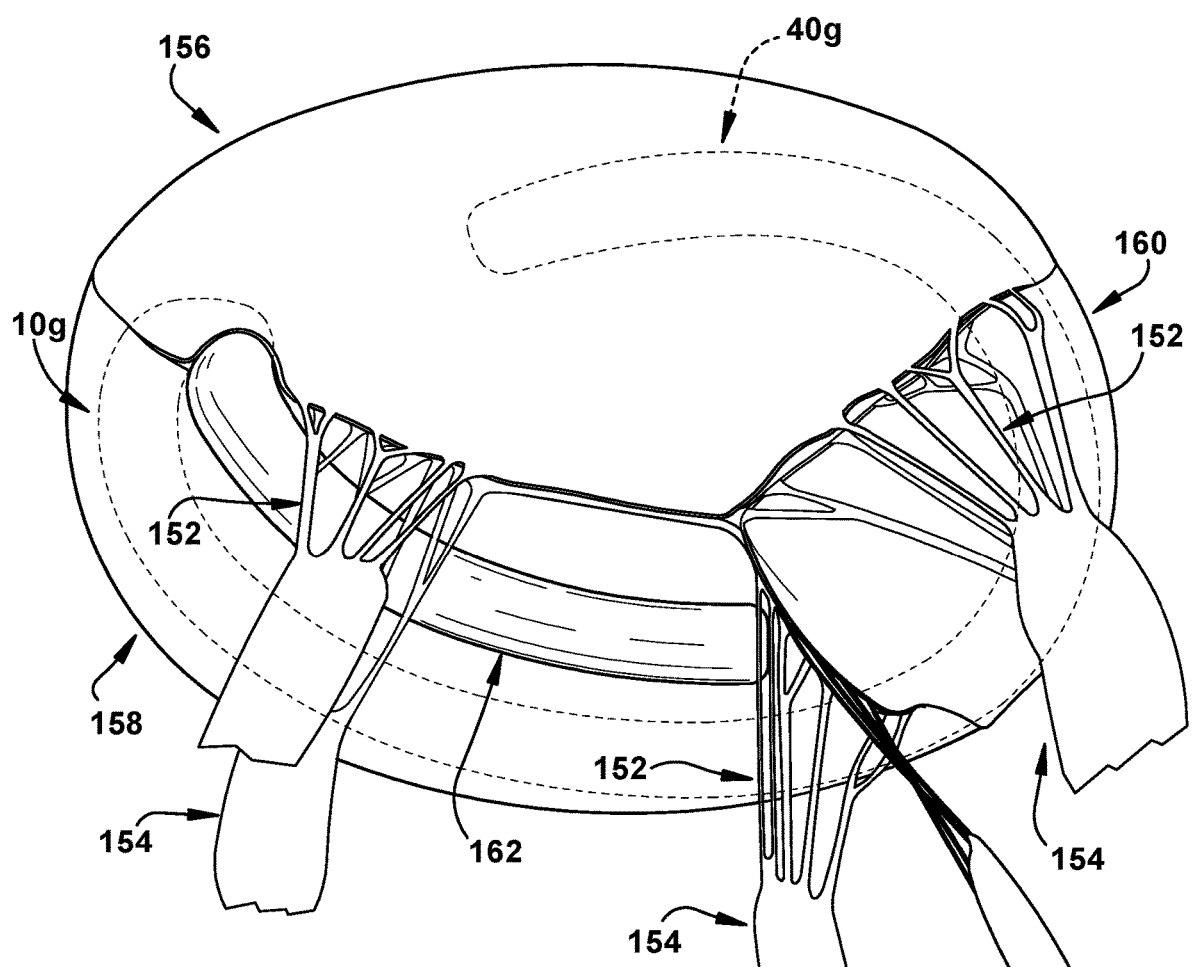
FIG. 16B is a perspective view showing an inferior aspect of the tricuspid valve in FIG. 16A.
Figure 17A:
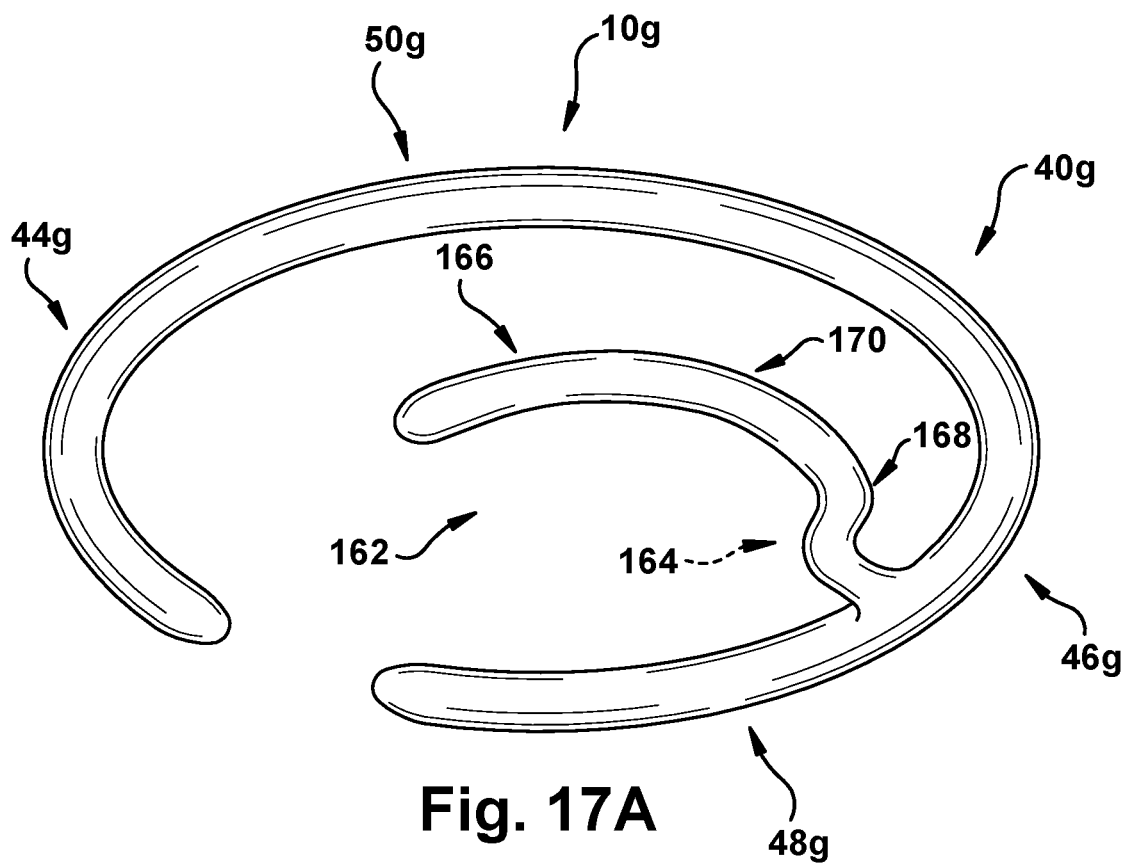
FIG. 17A is a perspective view showing an alternative configuration of the apparatus in FIG. 14A.
Figure 17B:
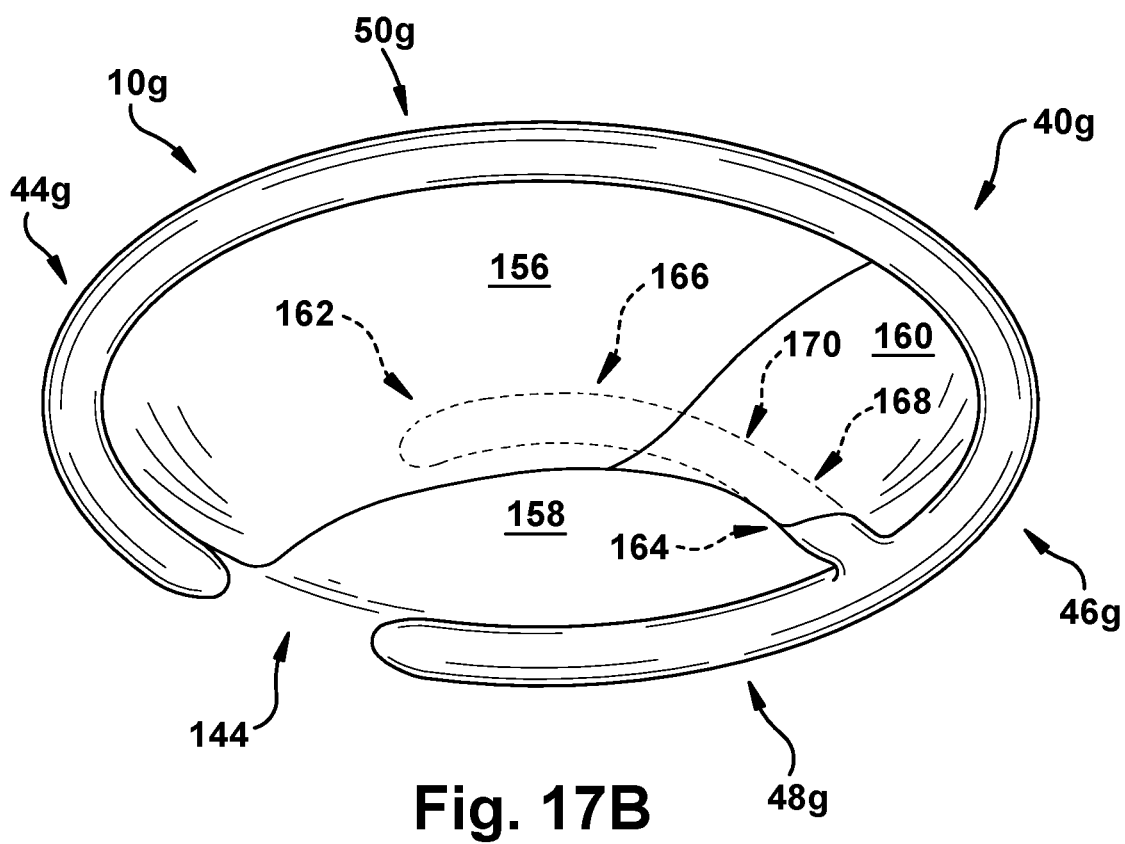
FIG. 17B is a perspective view of the apparatus in FIG. 17A implanted about a diseased tricuspid valve.
Figure 17C:
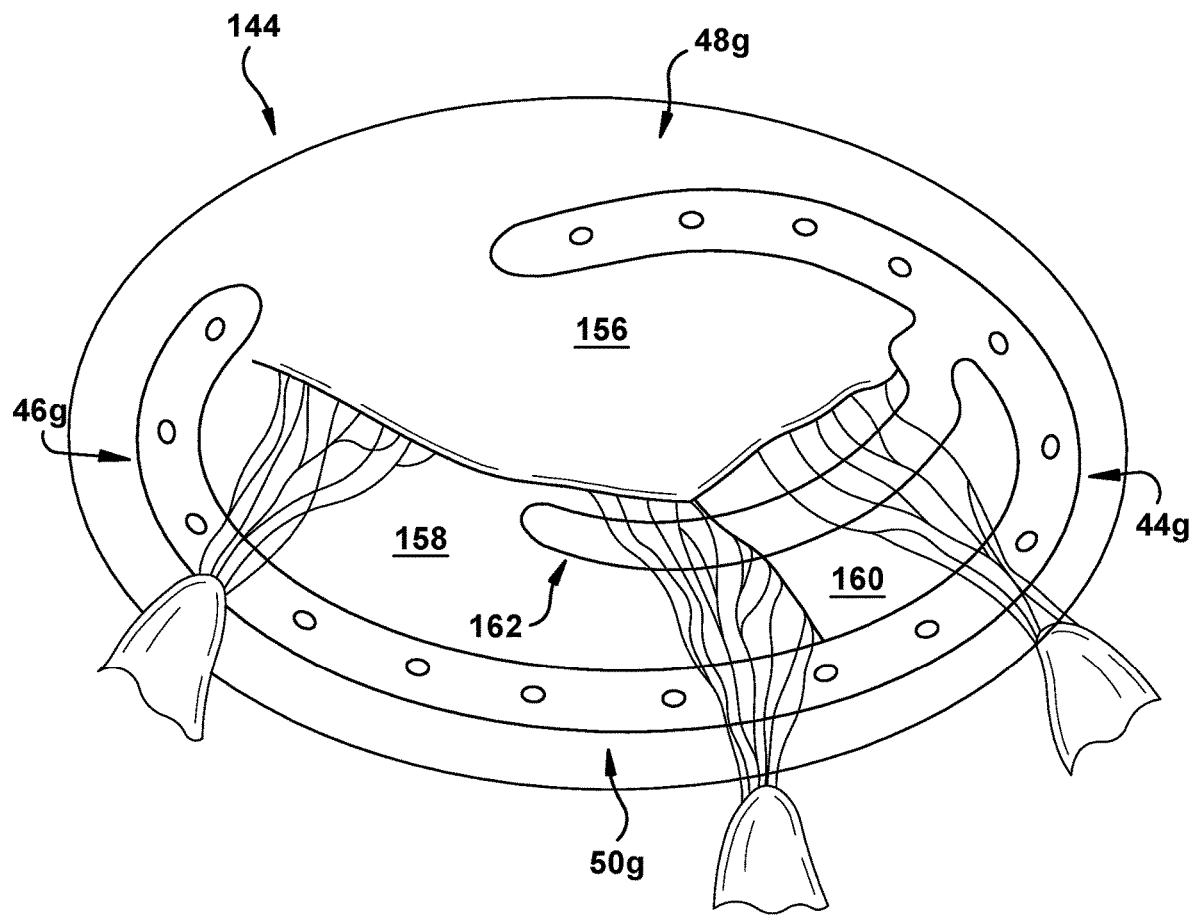
FIG. 17C is a perspective view showing an inferior aspect of the tricuspid valve in FIG. 17B.
Figure 17D:
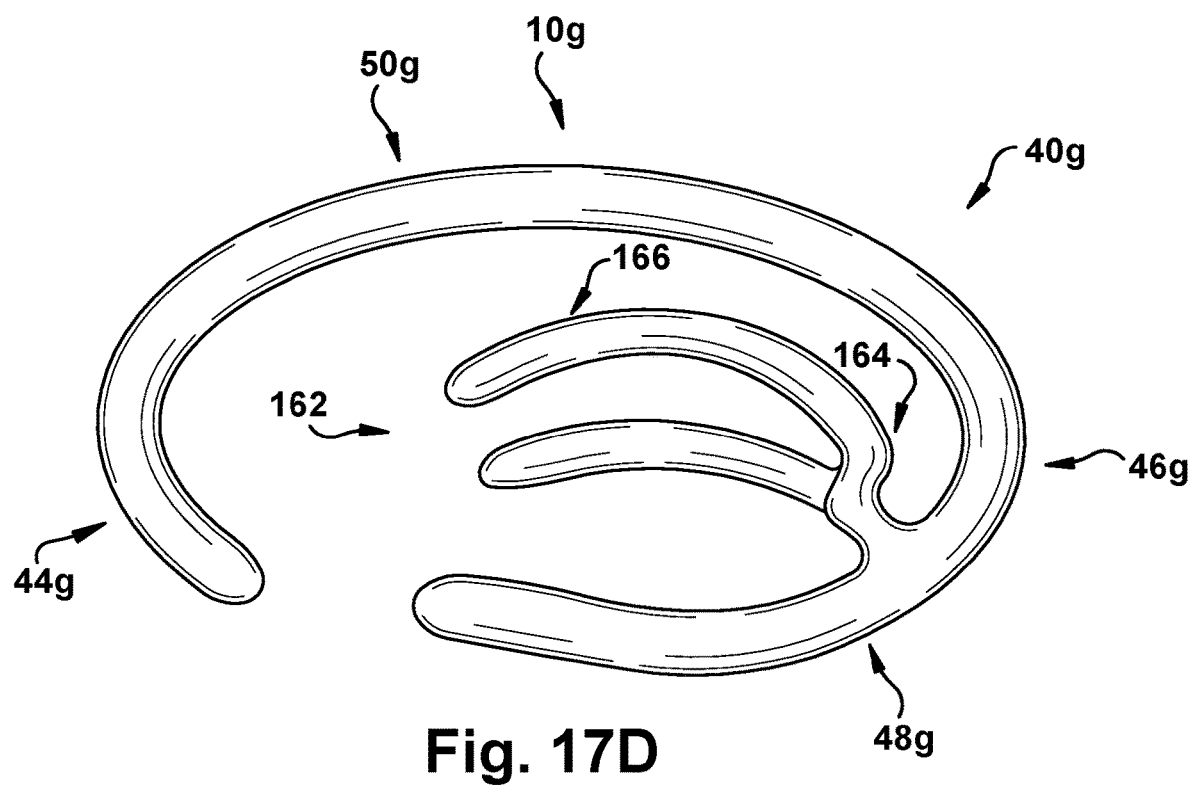
FIG. 17D is a perspective view showing an alternative configuration of the apparatus in FIG. 17A.
Figure 17E:
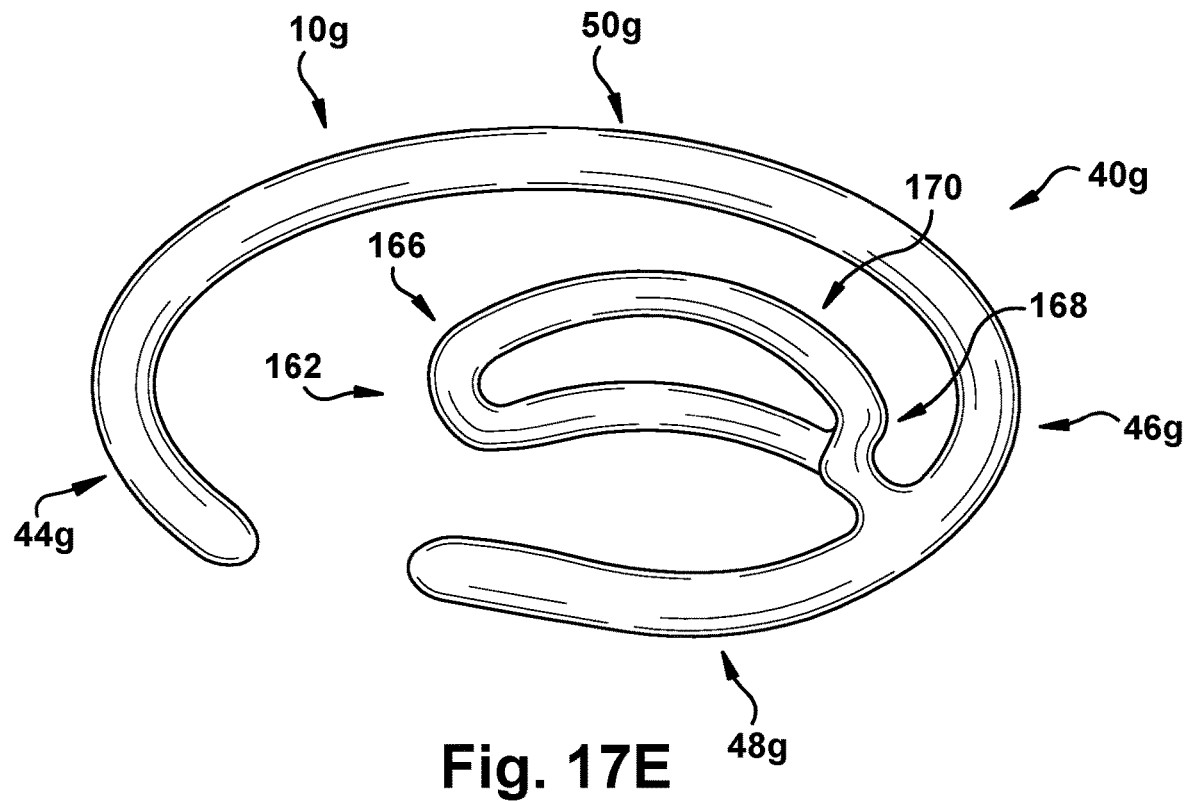
FIG. 17E is a perspective view showing another alternative configuration of the apparatus in FIG. 17A.

Another aspect of the present disclosure is illustrated in FIGS. 16A-B and includes a method for treating regurgitation of blood flow through a regurgitant tricuspid valve 144. Although the method will be described below using the apparatus $10_g$ illustrated in FIGS. 14A-C, it should be appreciated that an apparatus comprising any one or combination of the geometric variations discussed herein may also be used to treat regurgitation of blood flow through a diseased tricuspid valve 144.

As described above, the apparatus $10_g$ (FIGS. 14A-C) comprises a partial ring-shaped annular support member $40_g$ having a 3D configuration dimensioned for attachment to the tricuspid annulus 150. The apparatus $10_g$ additionally includes an infra-annular anterior support member 162 that is integrally formed with the first intermediate portion $44_f$ of the substantially annular support member $40_g$. Although not shown in FIGS. 14A-C, it will be appreciated that all or only a portion of the apparatus $10_f$ (e.g., the annular support member $40_f$) can be covered with a layer 68 of biocompatible material, such as a sewing ring, at least one marker 70, and/or one or a combination of therapeutic agents.

The method can be performed in a substantially identical manner as the method for treating a regurgitant mitral valve 12 described above. For example, the dimensions of the tricuspid valve 144 can first be obtained to determine optimal dimensions for the apparatus $10_g$. Sizing of the tricuspid valve 144 can be performed using a valve sizing device, such as the sizing device 86 described above. After determining the dimensions of the tricuspid valve 144, blood flow through the tricuspid valve can be monitored to assess coaptation between the anterosuperior, posterior, and septal leaflets 156, 158 and 160 (as described above). Differently dimensioned sizing members 90 can be placed over the tricuspid valve 144 until substantially normal fluid flow (e.g., blood or saline) through the tricuspid valve is observed. When substantially normal blood flow is observed through the tricuspid valve 144, the dimensions of the sizing member 90 are noted and an apparatus $10_g$ having dimensions that correspond to the dimensions of the sizing member is selected for implantation. It should be appreciated that a saline solution test may additionally or alternatively be used to assess fluid flow and proper leaflet coaptation through the tricuspid valve 144.

After selecting an appropriately-dimensioned apparatus $10_g$, the apparatus is attached to a delivery device 114 or holder as described above. To begin the implant procedure, a silicone tube (not shown) is passed through at least one commissure of the tricuspid valve 144 and placed behind at least one subvalvular structure, such as the chordae tendineae 152 and/or papillary muscle(s) 154 associated with the anterosuperior tricuspid leaflet 156. Once the apparatus $10_g$ is securely attached to the delivery device 114, sutures (not shown) are placed in the tricuspid annulus 150. The delivery device 114 is then positioned about the superior aspect of the tricuspid valve 144. Next, the sutures are passed through the marker(s) 70 (e.g., holes), while the delivery device 114 engages the tricuspid valve 144 and the substantially annular support member $40_g$ of the apparatus $10_g$ is advanced toward the tricuspid annulus 150.

After doing so, the silicone tube is manipulated so that an open end of the tube engages a distal end of the infra-annular anterior support member 162. The tube is then gently pulled from its non-engaged end, which causes the infra-annular anterior support member 162 to move through the commissure and engage at least one subvalvular structure. The tube is then disengaged, followed by removal of the handle member 88 and tightening of the sutures so that the apparatus $10_g$ is securely positioned about the tricuspid valve 144. After tightening of the sutures is complete, the sutures are cut so that the delivery device 114 or holder is detached from the apparatus $10_g$ and removed from the right atrium 146.

With the apparatus $10_g$ securely in place (FIGS. 16A-B), two levels of cardiac remodeling can simultaneously occur. At the sub-annular level, the infra-annular anterior support member 162 supports at least one subvalvular structure (e.g., the inferior free edge of the anterosuperior tricuspid leaflet 156, the chordae tendineae 152 associated with the anterior leaflet, and/or papillary muscle(s) 154 associated with anterior leaflet) during systole by moving forward the subvalvular structure(s), which reduces the restrictive motion of the anterior leaflet 24 and prevents or mitigates regurgitation of blood through the tricuspid valve 144. Furthermore, ventricular remodeling caused by ischemic and dilated cardiomyopathy is prevented or mitigated by pushing (or moving) forward the anterior and inferior wall of the right ventricle 148. Also at the annular level, the 3D saddle-shaped geometry of the apparatus $10_g$ remodels the tricuspid annulus 150 and reduces the annular diameter to improve leaflet coaptation. Upon proper implantation of the apparatus $10_g$, the procedure can be completed so that normal blood flow can resume through the tricuspid valve 144.

Figure 18A:
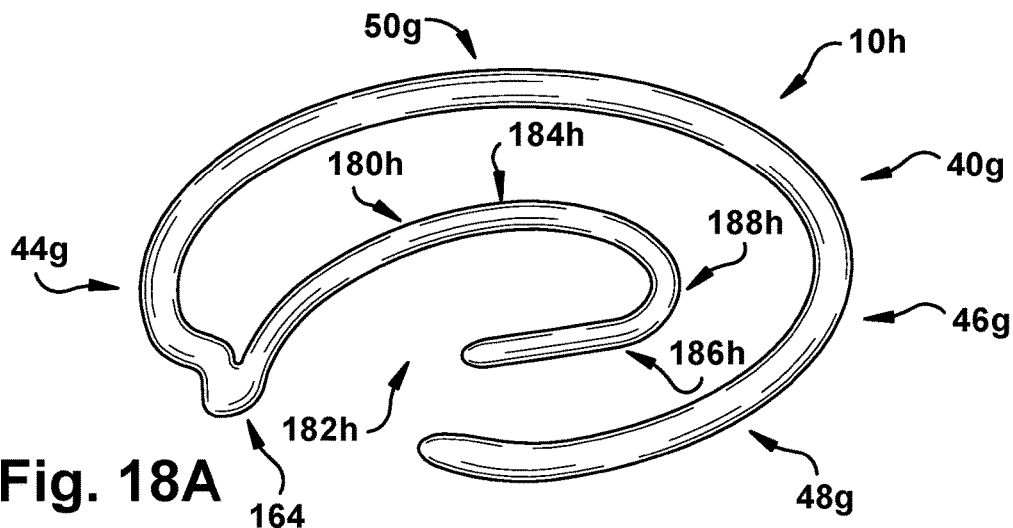
FIG. 18A is a perspective view showing an alternative configuration of the apparatus in FIG. 14A.
Figure 18B:
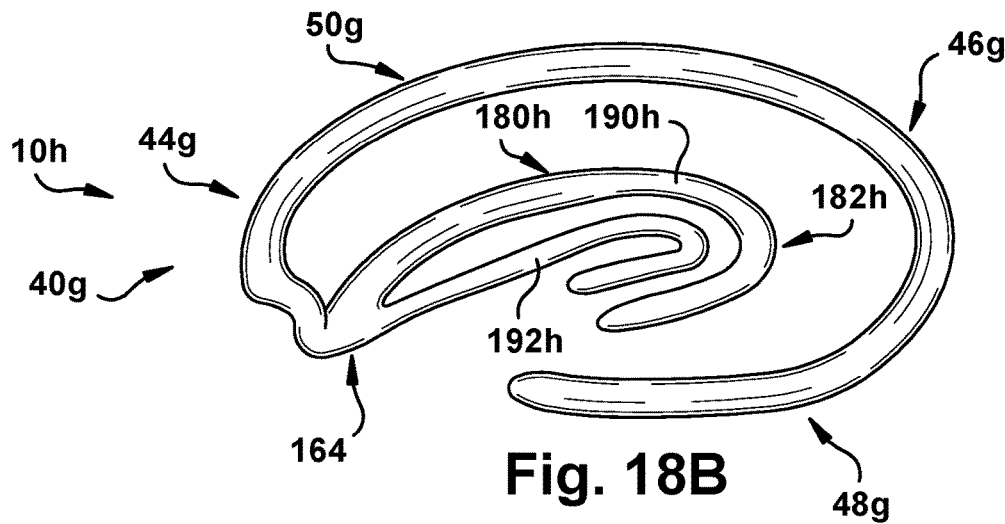
FIG. 18B is a perspective view showing an alternative configuration of the apparatus in FIG. 18A.
Figure 18C:
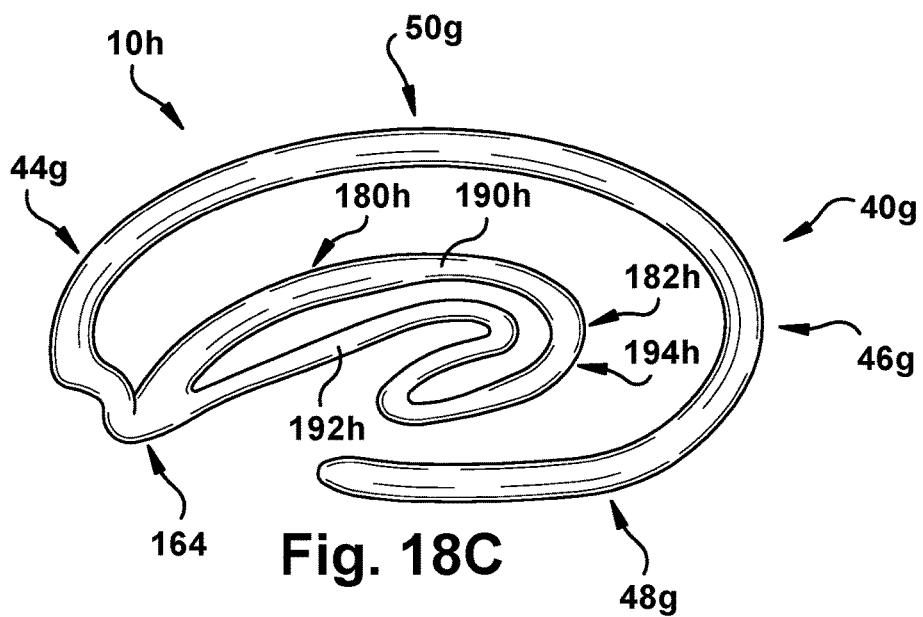
FIG. 18C is a perspective view showing another alternative configuration of the apparatus in FIG. 18B.
Figure 21:
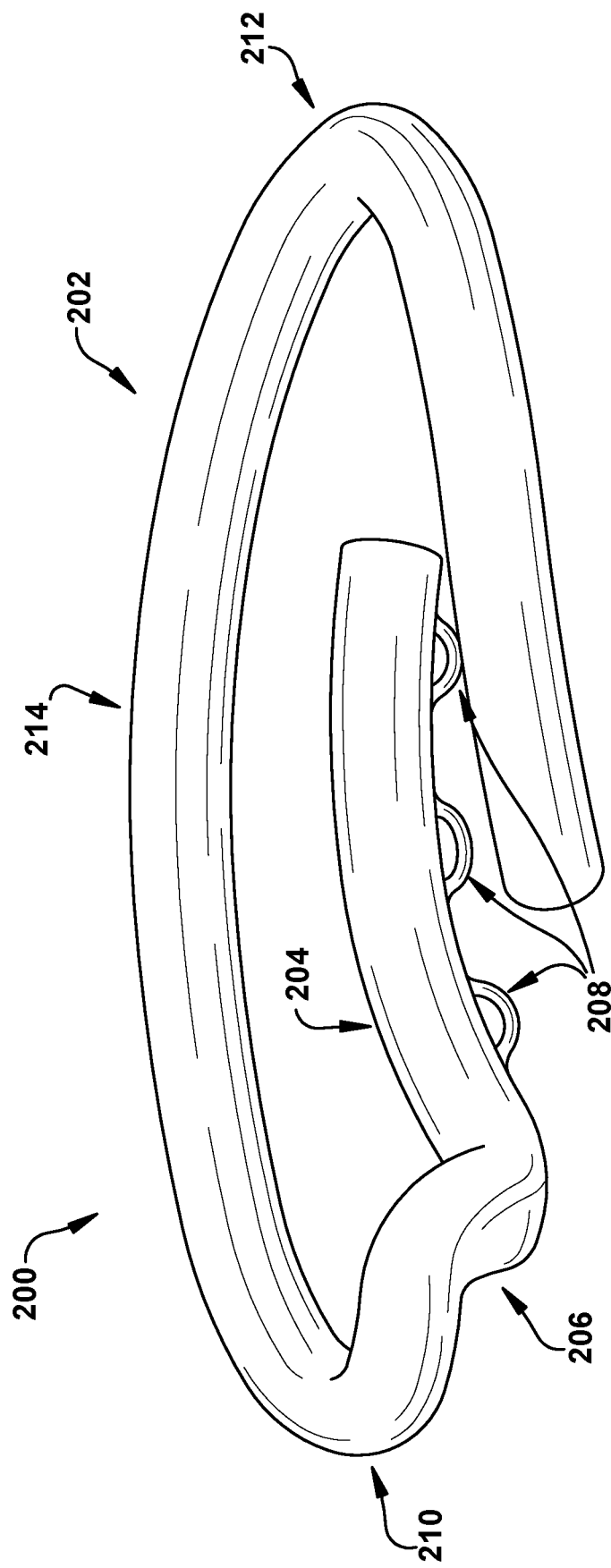
FIG. 21 is a perspective view of the apparatus shown in FIG. 20.
Figure 22:
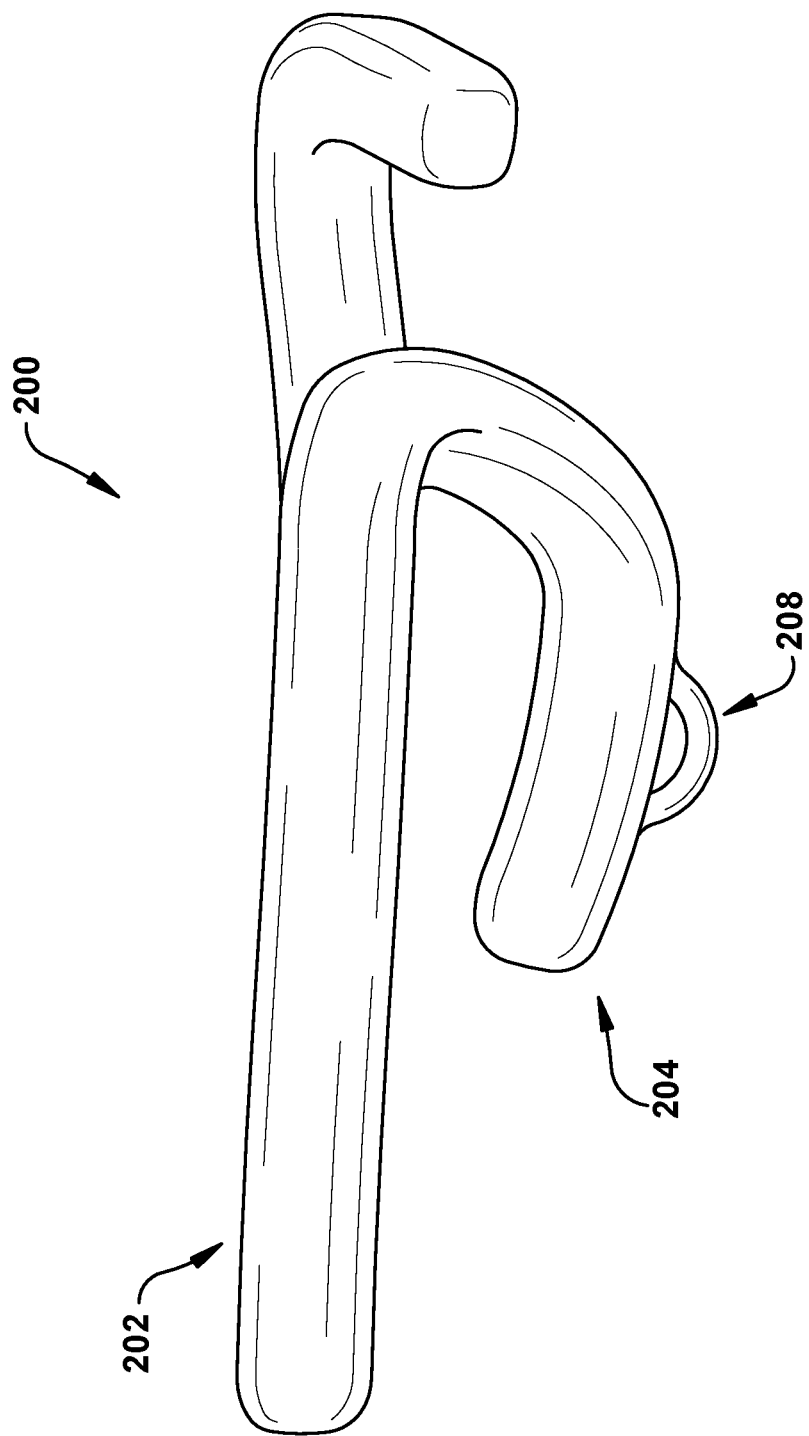
FIG. 22 is a another side view of the apparatus in FIG. 20.

Another aspect of the present disclosure is illustrated in FIGS. 18A-C. The apparatus $10_h$ shown in FIGS. 18A-C is identically constructed as the apparatus $10_g$ shown in FIGS. 14A-C, except as described below. In FIGS. 18A-C, structures that are identical as structures in FIGS. 14A-C use the same reference numbers, whereas structures that are similar but not identical carry the suffix "h". It should be appreciated that the apparatus $10_h$ can be constructed from any of the materials described above, and that the apparatus can include a layer 68 of biocompatible material and/or a therapeutic agent(s), as also described above.

The apparatus $10_h$ can comprise a substantially annular support member $40_g$ and at least one infra-annular tri-structure support member 200 securely connected thereto. The substantially annular support member $40_g$ can have a 3D shape that corresponds to the 3D shape of the tricuspid annulus 150 (FIG. 15). The substantially annular support member $40_g$ can define a longitudinal axis LA (as shown in FIG. 14C) and include an anterior end portion $50_g$, a posterior end portion $48_g$, and oppositely disposed first and second intermediate portions $44_g$ and $46_g$ extending between the anterior and posterior end portions. The anterior end portion $50_g$ and the posterior end portion $48_g$ are dimensioned for attachment to anterior and posterior portions of the tricuspid annulus 150 (FIG. 15), respectively. Although the substantially annular support member $40_g$ is shown as having a C-shaped or partial ring configuration, it will be appreciated that the substantially annular support member can have other configurations, such a completely annular ring configuration.

The infra-annular tri-structure support member 200 is dimensioned, shaped, and configured to extend below the anterosuperior, posterior, and septal leaflets 156, 158, and 160 and across or behind at least one subvalvular structure when the apparatus $10_h$ is implanted on or about the tricuspid annulus 150. The infra-annular tri-structure leaflet support member 200 is securely and directly connected to the substantially annular support member $40_g$ at a first location 202. As shown in FIG. 6A, for example, the infra-annular tri-structure leaflet support member 200 is securely and directly connected to the first intermediate portion $44_g$. Although not shown, it will be appreciated that the infra-annular tri-structure support member 200 can alternatively be securely and directly connected to the second intermediate portion $46_g$.

The infra-annular tri-structure support member 200 comprises a hook-shaped engaging portion $182_h$ that is integrally and directly connected to the substantially annular support member $40_g$ via a neck portion 164. The engaging portion $182_h$ further comprises a first engaging portion $184_h$, a second engaging portion $186_h$, and a bend portion $188_h$ extending between the first and second engaging portions. Each of the first and second engaging portions $184_h$ and $186_h$ has a continuous, arc-shaped (or arcuate) configuration configured to extend across or behind at least one subvalvular structure. The first and second engaging portions $184_h$ and $186_h$ can have concave and convex shapes (respectively) relative to the anterior end portion $50_g$ of the substantially annular support member $40_g$.

The first engaging portion $184_h$ is configured to extend across or behind at least one subvalvular structure, such as: an inferior aspect of the posterior leaflet 158, such as an inferior free edge (not shown) of the posterior leaflet; chordae tendineae 152 associated with the posterior leaflet; one or more papillary muscles 154 associated with the tendineae chordae of the posterior leaflet; and combinations thereof. Additionally, the second engaging portion $186_h$ is configured to extend across or behind at least one subvalvular structure, such as: an inferior aspect of the anterosuperior leaflet 156, such as an inferior free edge (not shown) of the anterosuperior leaflet; chordae tendineae 152 associated with the anterosuperior leaflet; one or more papillary muscles 154 associated with the chordae tendineae of the anterosuperior leaflet; an inferior aspect of the septal leaflet 160, such as an inferior free edge (not shown) of the septal leaflet; chordae tendineae associated with the septal leaflet; one or more papillary muscles associated with the chordae tendineae of the septal leaflet; and combinations thereof. In one example of the present disclosure, the second engaging portion $186_h$ is configured to extend across or behind a subvalvular structure associated with (or comprising) the anterosuperior and septal leaflets 156 and 160.

The first and second engaging portions $184_h$ and $186_h$ can be located in the same lateral plane (i.e., a plane that extends below and parallel or substantially parallel to the longitudinal axis LA) or, alternatively, offset from one another relative to a central axis CA (not shown in FIGS. 18A-C). In this manner, the first and second engaging portions $184_h$ and $186_h$ can be positioned to contact the same or different corresponding subvalvular structures. Where the first and second engaging portions $184_h$ and $186_h$ are offset from one another, for example, the first engaging portion can be configured to extend across or behind an inferior aspect of the posterior leaflet 158 (e.g., an inferior free edge of the posterior leaflet), and the second engaging portion can be configured to extend across or behind chordae tendineae 152 associated with the anterosuperior and septal leaflets 156 and 160.

Alternative configurations of the infra-annular posterior and inferior support member 180 are illustrated in FIGS. 6B-C. As shown in FIG. 6B, the engaging portion 182 of the infra-annular posterior and anterior support member 180 can have a bifurcated configuration comprising spaced apart first and second engaging members 190 and 192. The first and second engaging members 190 and 192 can be spaced apart, and axially offset from one another (relative to a central axis CA), by a distance D1. Generally, the distance D1 can be varied depending upon mitral valve anatomy, the particular valvular insufficiency from which a subject is suffering, as well as other factors. In particular, the distance D1 can be varied to facilitate contact between the first and second engaging members 190 and 192 and one or more subvalvular structures. Each of the first and second engaging members 190 and 192 includes first and second engaging portions 184 and 186, as described above.

As shown in FIG. 6C, the engaging portion 182 of the infra-annular posterior and anterior support member 180 can alternatively have an arcuate, loop-shaped configuration that includes an aperture 134 extending therethrough. The loop-shaped engaging portion 182 can comprise first and second engaging members 190 and 192 that join at a common arcuate bend 194. The first and second engaging members 190 and 192 can be spaced apart, and axially offset from one another (relative to a central axis CA), by a distance D1. Generally, the distance D1 can be varied depending upon mitral valve anatomy, the particular valvular insufficiency from which a subject is suffering, as well as other factors.

It will be appreciated that the apparatus $10_d$ can additionally or optionally include other features as the apparatus 10 shown in FIGS. 1A-B and described above. For example, the apparatus $10_d$ can include: an adjustable mechanism 54; a layer 68 of biocompatible material; at least one marker 70 to facilitate attachment of the apparatus to the mitral annulus 18; and/or one or a combination of therapeutic agents.

Another aspect of the present disclosure is illustrated in FIGS. 19A-27. The apparatus 200 shown in FIGS. 19A-27 can be identically or similarly constructed as the apparatus 10, $10_a$, $10_b$, $10_c$, $10_d$, and $10_h$ shown in FIGS. 1A-18C, except where described below. It should be appreciated that the apparatus 200 shown in FIGS. 19A-27 can be constructed from any of the materials described above, and that the apparatus can include a layer 68 of biocompatible material and/or a therapeutic agent(s) (also described above).

Despite advances in understanding the pathophysiology of ischemic mitral regurgitation as well as advances in surgical technique and perioperative care, surgical treatment of ischemic mitral regurgitation is associated with mortality rates as high as 20% in some series. Observational studies in both experimental animals and clinical patients reveal that the mechanisms of ischemic mitral regurgitation are varied. Carpentier's classification of leaflet motion reveals two plausible mechanisms. In patients with Carpentier's type I dysfunction, leaflet motion is unrestricted and ischemic mitral regurgitation occurs on the basis of annular dilation, with resultant failure of leaflet coaptation. This is ordinarily treated adequately by ring annuloplasty. In the case of Carpentier's type IIIb dysfunction, there is tethering of A3 and P3 segments to the anterior and posterior leaflets, respectively. This results from posterior displacement of the posterior papillary muscle and subjacent left ventricle as a product of myocardial infarction.

This mechanism is poorly treated by simple mitral annuloplasty as abundant clinical experience has shown. Ring annuloplasty fails to restore adequate leaflet coaptation as the leaflet edges remain tethered below the annular level. Adequate treatment will only result if the leaflet edges can be allowed to return to the annular level. In addition, the combination of annular dilation as well as leaflet tethering may be at play with individual patients. These patients are also inadequately treated by ring annuloplasty alone. These latter two mechanisms are likely the mechanisms responsible for reports of up to 20% residual and/or progressive mitral regurgitation after annuloplasty alone.

To address these and other shortcomings, another aspect of the present disclosure can include the apparatus 200 shown in FIGS. 19A-22 and described below. In some instances, the apparatus 200 can include a substantially annular support member 202, at least one infra-annular support member 204 securely connected to the substantially annular support member at a first location 206, and at least one anchoring element 208 associated with the at least one infra-annular support member. The substantially annular support member 202 can have at least a first intermediate portion 210, a second intermediate portion 212, and a posterior end portion 214 extending between the first and second intermediate portions. The posterior end portion 214 can be dimensioned for attachment to a posterior portion of the annulus of a diseased heart valve. The at least one infra-annular support member 204 can be dimensioned to extend below at least one of the posterior and anterior valve leaflets and across or behind at least one subvalvular structure.

In other instances, the apparatus 200 can include a substantially annular support member 202, a first infra-annular support member 204' securely connected to the substantially annular support member at a first location 206, a second infra-annular support member 204" securely connected to the substantially annular support member at a second location 216, and at least one anchoring element 208 associated with one or both of the first and second infra-annular support members. The substantially annular support member 202 can have at least a first intermediate portion 210, a second intermediate portion 212, and a posterior end portion 214 extending between the first and second intermediate portions. The posterior end portion 214 is dimensioned for attachment to a posterior portion of the annulus of a diseased heart valve. The first and second infra-annular support members 204' and 204" are dimensioned to extend below at least one of the posterior and anterior valve leaflets and across or behind at least one subvalvular structure. An apparatus 200 having first and second infra-annular support members 204' and 204" is shown in FIG. 19B.

The at least one anchoring element 208 can be configured to securely receive a prosthetic chordae tendineae 218 (FIG. 23) for attachment to a papillary muscle 220. Examples of prosthetic chordae tendineae 218 that can be securely received by an anchoring element 208 are disclosed in U.S. Patent Publication No. 2011/0288635 A1 to Miller et al., U.S. Patent Publication No. 2003/0105519 A1 to Fasol et al., and U.S. Patent Publication No. 2006/0259135 A1 to Navia et al. The anchoring element 208 can be directly or indirectly associated with an infra-annular support member 204. By "directly associated", it is meant that the anchoring element 208 is physically attached to at least a surface 222 (FIG. 20) that forms the infra-annular support member 204 without any intervening elements or structures between the surface and the anchoring element. By "indirectly associated", it is meant that the anchoring element 208 is physically attached to the infra-annular support member 204, albeit with one or more intervening elements or structures extending between the surface 222 and the anchoring element. It will be appreciated that the infra-annular support member 204 can include only one or two, three, or more anchoring elements 208.

Figure 23:
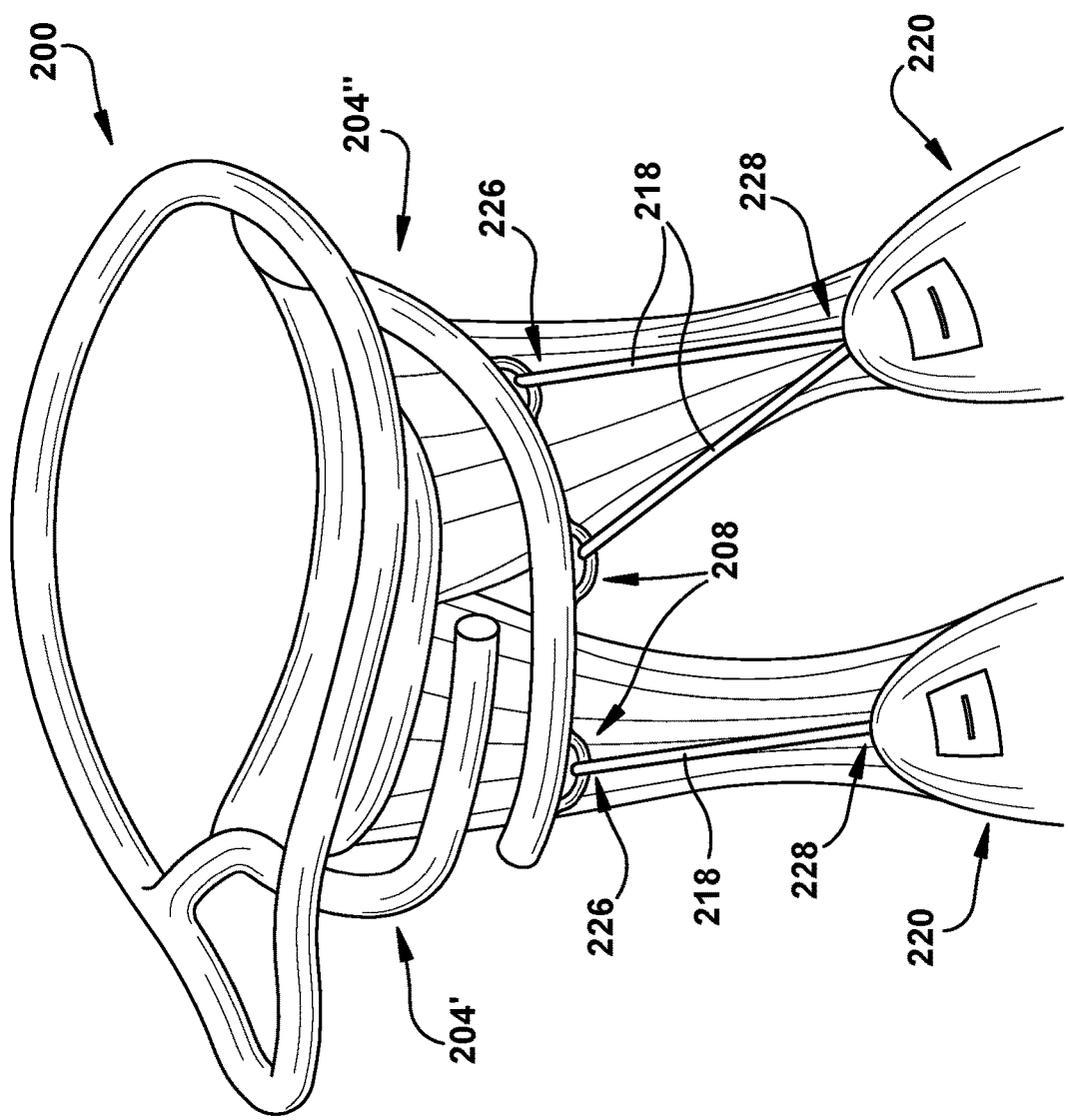
FIG. 23 is a schematic illustration showing an alternative configuration of the apparatus in FIGS. 19A-B implanted in a heart ventricle.
Figure 24:
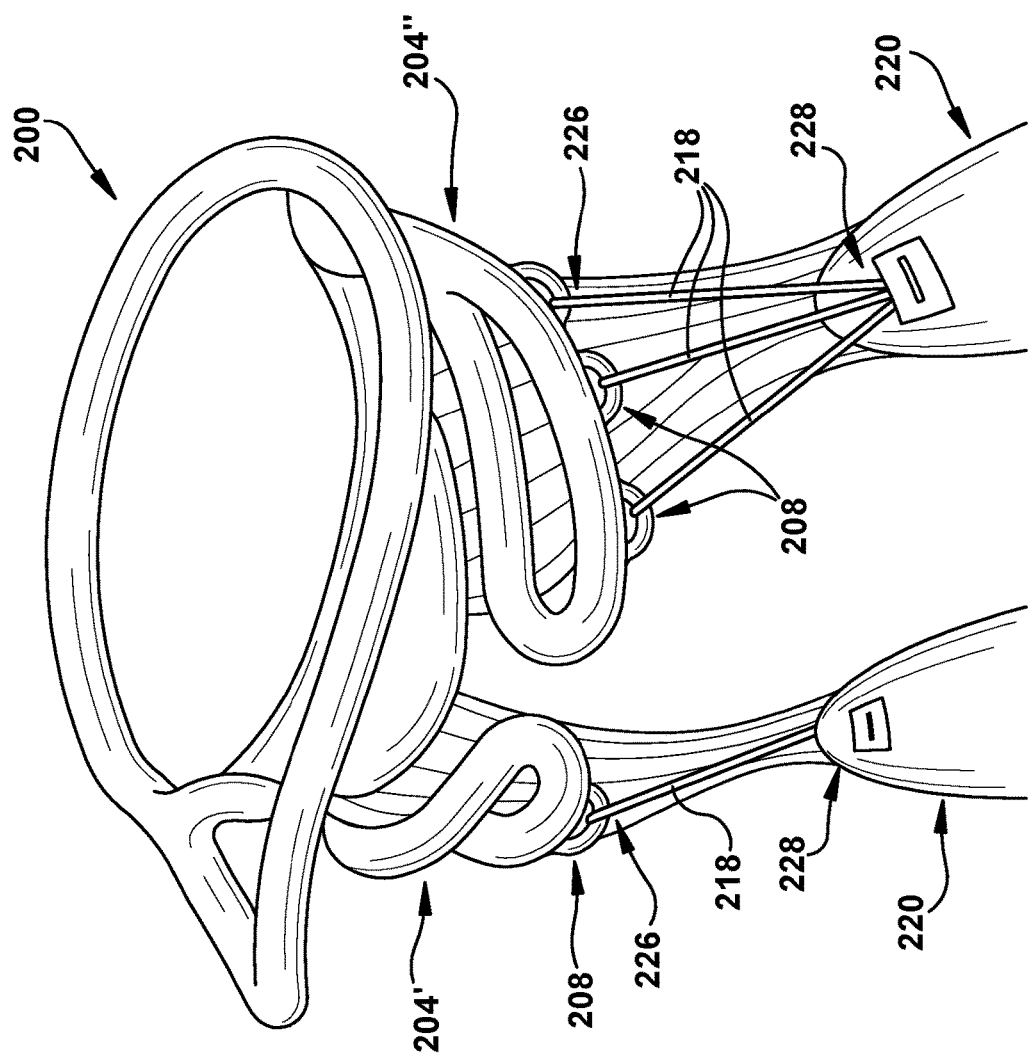
FIG. 24 is a schematic illustration showing another alternative configuration of the apparatus in FIGS. 19A-B implanted in a heart ventricle.
Figure 25:
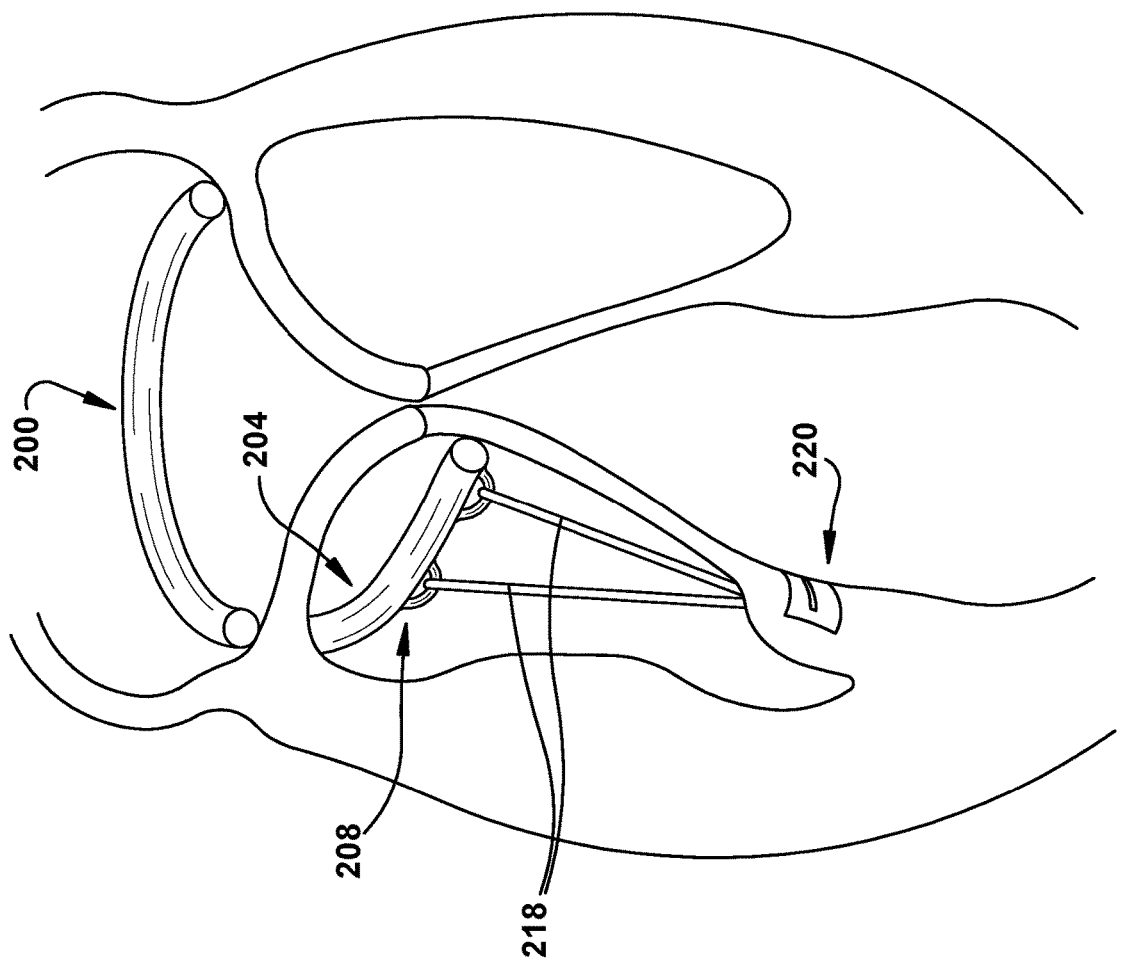
FIG. 25 is a cross-sectional view showing the apparatus in FIG. 19A implanted in a heart ventricle.
Figure 26B:
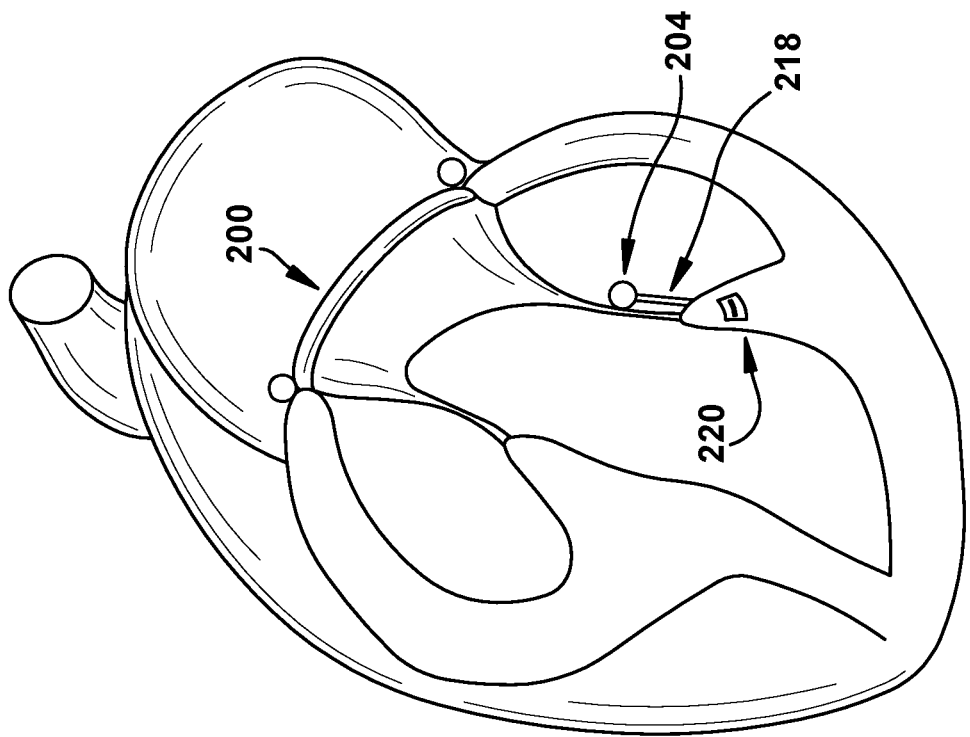
FIGS. 26A-B shows a regurgitant heart valve (left) being treated with the apparatus in FIG. 19B.
Figure 26A:
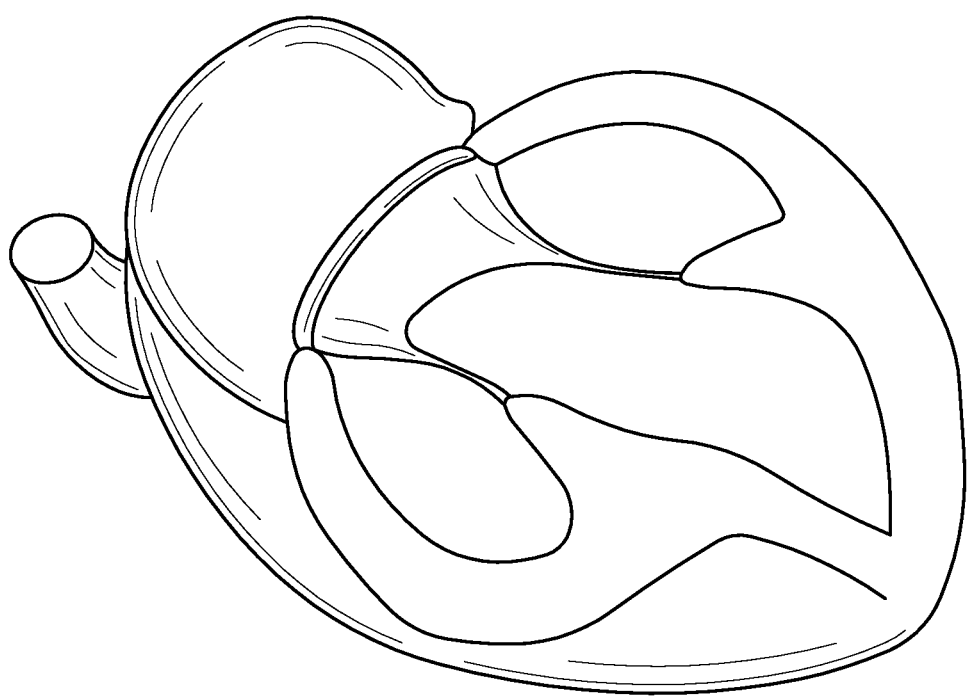
Figure 27B:
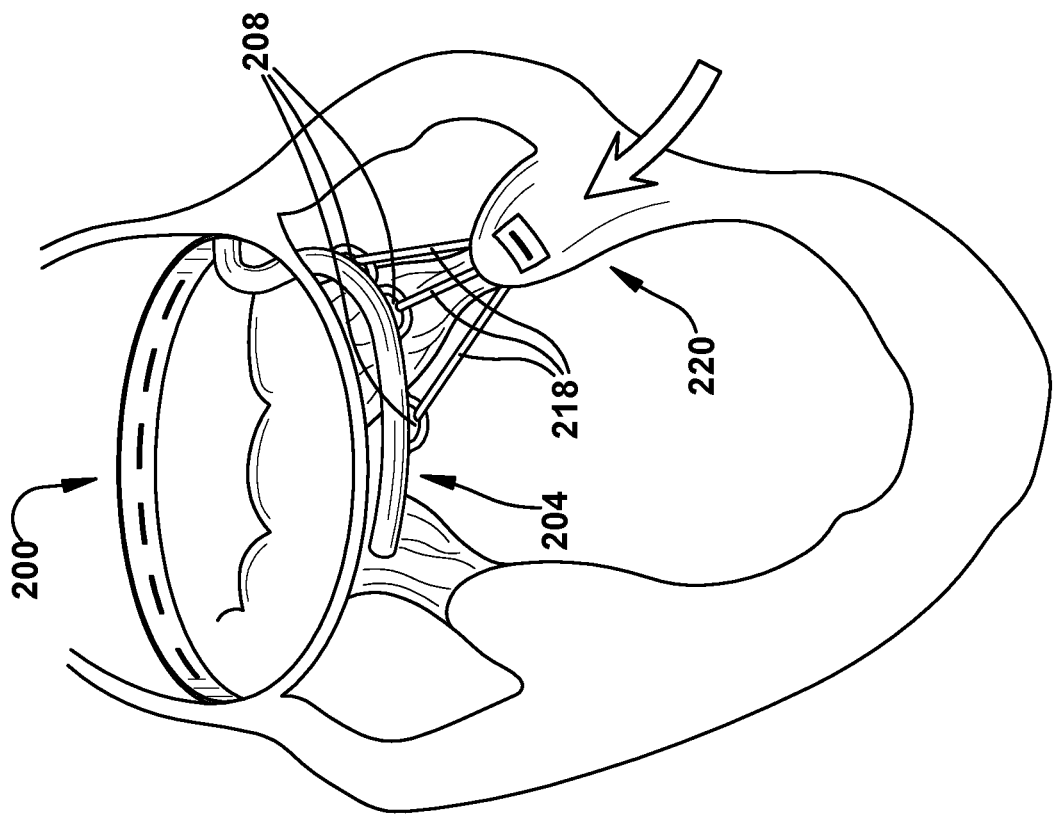
FIG. 27A-B shows a regurgitant heart valve FIG. 27A being treated with an alternative configuration of the apparatus in FIG. 19B.
Figure 27A:
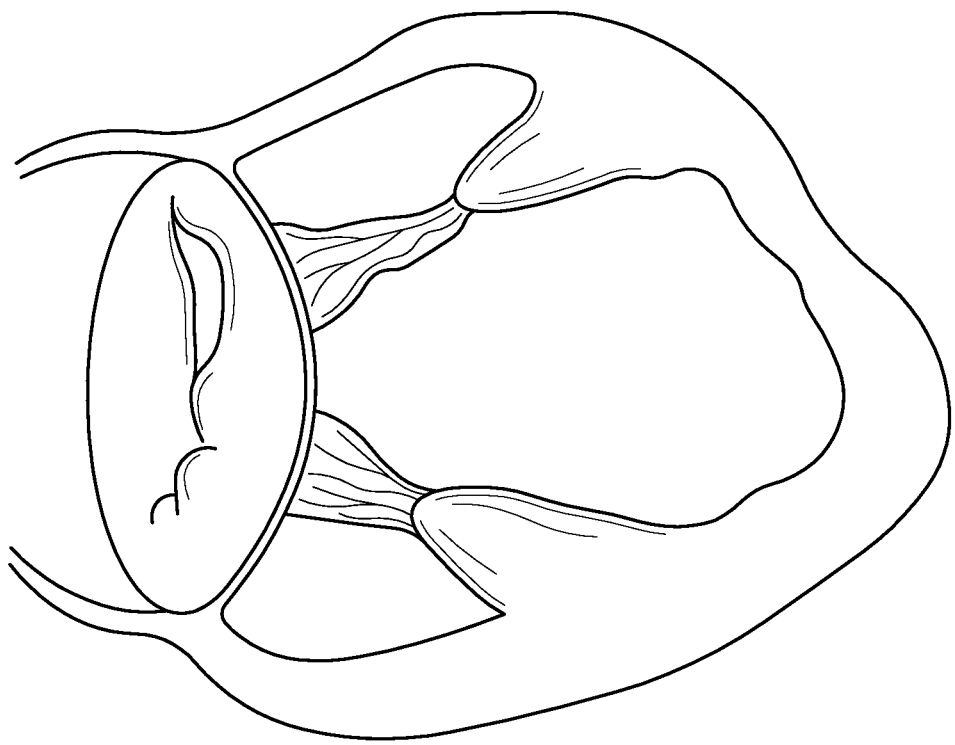

The anchoring element 208 can comprise any structure, component, member, or combination thereof that is configured to securely receive a prosthetic chordae tendineae 218 for attachment to a papillary muscle 220 (FIGS. 23-25). As shown in FIGS. 19A-B, for example, the anchoring element 208 can have a U-shaped or semi-circular shape that forms an aperture 224 when connected to or associated with the infra-annular support member 204. In this instance, the aperture 224 can be configured to receive a portion of a prosthetic chordae tendineae 218 therethrough. It will be appreciated that the anchoring element 208 can have a variety of other shapes and configurations, so long as the anchoring element is configured to securely receive a prosthetic chordae tendineae 218 for attachment to a papillary muscle 220. For example, the anchoring element 208 can be V-shaped. Alternatively, the anchoring element 208 can include a snap, clip, or magnetic member capable of securely receiving the prosthetic chordae tendineae 218. Where multiple anchoring elements 208 are present (e.g., on a single infra-annular support member 204), each of the anchoring elements can be physically spaced apart from one another (e.g., radially or axially spaced apart in a parallel or in-series configuration, respectively). The anchoring element 208 can be integrally formed with the infra-annular support member 204 (e.g., formed from the same material) or separately attached thereto (e.g., using an adhesive). The material used to form the anchoring element 208 can be the same as, or different from, the material used to form the infra-annular support member 204.

Advantageously, the anchoring elements 208 provide a mechanism for stabilizing the papillary muscles 220 upon implantation of the apparatus 200, which prevents late apical migration of the subvalvular apparatus. This mechanism is not present with existing annuloplasty rings, which only remodel the valve annulus and do not exert a therapeutic effect on the papillary muscles and migration of the subvalvular apparatus. Additionally, this mechanism is not present with conventional artificial chordae, which fail to provide valve annulus remodeling.

Implantation of the apparatus 200 is illustrated in FIGS. 26A-27B. Proximal and distal ends 226 and 228 of the prosthetic chordae tendineae 218 can be attached to the anchoring element 208 and the head of the papillary muscle 220, respectively. The distal end 228 of the prosthetic chordae tendineae 218 can be attached to the head of the papillary muscle 220 using a standard technique. All or only a portion of the native chordae can be removed from the patient. Alternatively, the native chordae may remain in the patient along with the implanted prosthetic chordae tendineae 218. Advantageously, attachment of the prosthetic chordae tendineae 218 pulls or moves the papillary muscles 220 in a medial direction. Medial movement of the papillary muscles 220 can improve cardiac function by creating a reverse remodeling of a posterior left ventricular wall, improving valve leaflet coaptation, and reducing tension across the native chordae. When implanted, the apparatus 200 can also stabilize the position of the papillary muscles 220 and prevent late apical migration of the subvavular apparatus, which is of benefit in these generally unhealthy patients. Thus, in some instances, the apparatus 200 can be employed to treat a subject suffering from Carpentier's type I dysfunction or Carpentier's type IIIb dysfunction. In a patient suffering from Carpentier's type IIIb dysfunction, for example, implantation of the apparatus 200 may be especially therapeutic since such patients suffer from tethering of A3 and P3 segments to the anterior and posterior leaflets, respectively, and the apparatus advantageously eliminates the possibility of leaflet tethering below the annular level while also remodeling the dysfunctional valve at the annular level.

From the above description of the disclosure, those skilled in the art will perceive improvements, changes and modifications. Such improvements, changes, and modifications are within the skill of one having ordinary skill the art. All patents, patent applications, and publication cited herein are incorporated by reference in their entirety.

The following is claimed:

1. A method for treating regurgitation of blood flow through a diseased heart valve of a subject, the diseased heart valve including an annulus, an anterior valve leaflet, a posterior valve leaflet and a subvalvular structure, said method comprising the steps of:

providing an apparatus comprising:
  a substantially annular support member having at least a first intermediate portion, a second intermediate portion and a posterior portion extending between the first and second intermediate portions;
  at least one infra-annular support member integral with the substantially annular support member; and
  at least one anchoring element associated with the at least one infra-annular support member;

attaching the substantially annular support member to the annulus of the diseased heart valve so that the at least one infra-annular support member extends below at least one of the posterior and anterior valve leaflets and or across at least one subvalvular structure; and attaching a proximal end of a prosthetic chordae tendineae to the at least one anchoring element at a location above a papillary muscle and attaching a distal end of the prosthetic chordae tendineae to the papillary muscle, so that the papillary muscle is caused to move medially; and preventing or substantially reduce regurgitation of blood flow through the diseased heart valve.

2. The method of claim 1, wherein said providing step further includes providing at least one anchoring element having a semi-circular shape.

3. The method of claim 1, wherein said providing step further comprises providing at least one anchoring element that is indirectly or directly associated with a surface of the at least one infra-annular support member so that an aperture is formed between the surface and a portion of the at least one anchoring element.

4. The method of claim 1, wherein attachment of the prosthetic chordae tendineae between the papillary muscle and the at least one anchor element stabilizes the position of the papillary muscles and prevents late apical migration of the subvalvular apparatus.

5. The method of claim 1, wherein the subject is suffering from Carpentier's type I dysfunction.

6. The method of claim 1, wherein the subject is suffering from Carpentier's type IIIb dysfunction.

7. The method of claim 1, wherein attaching the substantially annular support member to the annulus of the diseased heart valve so that the at least one infra-annular support member extends below at least one of the posterior and anterior valve leaflets and behind at least one subvalvular structure.

* * * * *